US009267107B2

(12) United States Patent
Garner et al.

(10) Patent No.: US 9,267,107 B2
(45) Date of Patent: Feb. 23, 2016

(54) PROCESS AND COMPOSITION FOR MANUFACTURE OF A MICROBIAL-BASED PRODUCT

(71) Applicant: MICROBIOS, INC., Houston, TX (US)

(72) Inventors: Matthew Ryan Garner, Amarillo, TX (US); Joseph Flint, Ithica, NY (US)

(73) Assignee: MICROBIOS, INC., Houston, TX (US)

( * ) Notice: Subject to any disclaimer, the term of this patent is extended or adjusted under 35 U.S.C. 154(b) by 0 days.

(21) Appl. No.: 13/898,370

(22) Filed: May 20, 2013

(65) Prior Publication Data

US 2013/0244308 A1    Sep. 19, 2013

Related U.S. Application Data

(63) Continuation of application No. 12/976,490, filed on Dec. 22, 2010, now Pat. No. 8,445,226, which is a continuation-in-part of application No. 12/772,137, filed on Apr. 30, 2010, now Pat. No. 7,888,062.

(60) Provisional application No. 61/300,301, filed on Feb. 1, 2010.

(51) Int. Cl.
| | |
|---|---|
| *C12N 1/00* | (2006.01) |
| *C12N 1/20* | (2006.01) |
| *C12P 1/00* | (2006.01) |
| *A61K 35/74* | (2015.01) |

(52) U.S. Cl.
CPC .. *C12N 1/20* (2013.01); *A61K 35/74* (2013.01)

(58) Field of Classification Search
CPC ....................................................... C12N 1/20
See application file for complete search history.

(56) References Cited

U.S. PATENT DOCUMENTS

| | | |
|---|---|---|
| 3,897,307 A | 7/1975 | Porubcan et al. |
| 4,112,942 A | 9/1978 | Scaife |
| 4,205,132 A | 5/1980 | Sandine et al. |
| 4,208,907 A | 6/1980 | Townsend et al. |
| 4,749,125 A | 6/1988 | Escallon et al. |
| 5,179,020 A | 1/1993 | Herman et al. |
| 5,529,793 A | 6/1996 | Garner et al. |
| 5,534,271 A | 7/1996 | Ware et al. |
| 5,641,209 A | 6/1997 | Kushi et al. |
| 5,652,194 A | 7/1997 | Dyer et al. |
| 6,033,691 A | 3/2000 | Craverno |
| 6,051,552 A | 4/2000 | Reid et al. |
| 6,140,355 A | 10/2000 | Egidio et al. |
| 6,258,374 B1 | 7/2001 | Friess et al. |
| 6,368,591 B1 | 4/2002 | Chen et al. |
| 6,455,063 B1 | 9/2002 | Rehberger et al. |
| 6,455,271 B1 | 9/2002 | Little, II et al. |
| 6,468,526 B2 | 10/2002 | Chrisope |
| 6,558,043 B2 | 5/2003 | Beghini et al. |
| 6,797,266 B2 | 9/2004 | Naidu |
| 6,872,357 B1 | 3/2005 | Bronshtein et al. |
| 6,887,489 B2 | 5/2005 | Rehberger et al. |
| 7,063,836 B2 | 6/2006 | Garner et al. |
| 7,291,326 B2 | 11/2007 | Ware et al. |
| 7,291,327 B2 | 11/2007 | Garner et al. |
| 7,323,166 B2 | 1/2008 | Brashears et al. |
| 7,608,700 B2 | 10/2009 | Klaenhammer et al. |
| 7,858,336 B1 | 12/2010 | Garner et al. |
| 7,888,062 B1 | 2/2011 | Garner et al. |
| 8,445,226 B2 | 5/2013 | Garner et al. |
| 2001/0014322 A1 | 8/2001 | Chen et al. |
| 2002/0037341 A1 | 3/2002 | Heo et al. |
| 2004/0043012 A1* | 3/2004 | Brashears ................... 424/93.45 |
| 2004/0063175 A1* | 4/2004 | Abraham et al. ............ 435/69.1 |
| 2004/0223956 A1 | 11/2004 | Naidu et al. |
| 2006/0269998 A1 | 11/2006 | Buck et al. |
| 2007/0254353 A1 | 11/2007 | Stavnsbjerg et al. |
| 2010/0074994 A1 | 3/2010 | Harel et al. |

FOREIGN PATENT DOCUMENTS

| | | |
|---|---|---|
| EP | 0259739 | 3/1988 |
| WO | 9201388 | 2/1992 |
| WO | 2005060937 | 7/2005 |
| WO | 2006032542 | 3/2006 |

OTHER PUBLICATIONS

Baldwin and Allison, Journal of Animal Science; National Animal Disease Center 57: (Suppl. 2) 461-477, 1993.
Bernard, Brashears et al., Journal of Food Protection, Isolation, selection, and characterization of lactic acid bacteria for a competitive exclusion product to reduce shedding of *Escherichia coli* O157:H7 in cattle. 66(3):355-363, 2003.
Bozoglu, T. F.; Ozilgen, M.; Bakir, U. Survival kinetics of lactic acid starter cultures during and after freeze-drying. Enzyme Microb. Technol. 1987, 9:531-537.
Brashears et al., Survival During Frozen and Subsequent Refrigerated Storage of Lactobacillus acidophilus Cells as Influenced by the Growth Phase. J Dairy Sci, Nov. 1995, vol. 78, No. 11, pp. 232-2335.
Callewaert et al., Bacteriocin Production with Lactobacillus amylovorus DCE 471 Is Improved and Stabilized by Fed-Batch Fermentation. Appl Environ Microbiol., Feb. 2000, vol. 66, No. 2, pp. 606-613.
Champagne, C. P.; Gardner, N. J. Effect of process parameters on the production and drying of Leuconostoc mesenteroides cultures. J. Ind. Microbiol. Biotechnol.; Jan. 25, 2002, vol. 28, pp. 291-296.
Corcoran, B. M.; Ross, R. P.; Fitzgerald, G. F.; Stanton, C. Comparative survival of probiotic lactobacilli spray-dried in the presence of prebiotic substances. J. Appl. Microbiol.; 2004, vol. 96, pp. 1024-1039. (Article accepted: Dec. 26, 2003).

(Continued)

*Primary Examiner* — Albert Navarro
(74) *Attorney, Agent, or Firm* — Novak Druce Connolly Bove + Quigg LLP

(57) ABSTRACT

Processes to produce microorganisms that can be incorporated into a microbial-based product that results in high viable cell yields and shelf-stable products are disclosed. These microbial-based products are useful for inhibiting pathogenic growth and as a food additive. A preferred microorganism is a lactic acid producing bacteria. In one embodiment, the process comprises inoculating a *lactobacillus* fermentation medium with lactic acid producing bacterial cells, harvesting the lactic acid producing bacterial cells at mid to late log phase, concentrating the lactic acid producing bacterial cells, and preserving the lactic acid producing bacterial cells at a concentration of at least $5\times10^9$ cfu/ml.

32 Claims, 13 Drawing Sheets

(56) References Cited

OTHER PUBLICATIONS

De Giulio et al., Use of alginate and cryo-protective sugars to improve the viability of lactic acid bacteria after freezing and freeze-drying. World Journal of Microbiology & Biotechnology, Jul. 2005, vol. 21, No. 5, pp. 739-746.

Erika Plessis; Leon M.T.Dicks, Evaluation of Random Amplified Polymorphic DNA; vol. 31, 1995, pp. 114-118.

Fu, W. Y.; Etzel, M. R. Spray-drying of *Lactococcus lactis* ssp *lactis* C2 and cellular injury. J. Food Sci. 1995, 60, 195-200.

Fujisawa, Tomohiko; International Journal of Systematic Bacteriology, Taxonomic Study of the Lactobacillus acidphilus group with recognition of *Lactobacillus gallinarum* sp. nov. and *Lactobacillus johnonii* sp. Jul. 1992, p. 487-491.

Gibbs et al., Int. J. Food Sci. Nutr., Encapsulation in the food industry: a review; 50: 213-224, 1999.

Hans, Helig et al., Applied and Environmental Microbiology; Molecular Diversity of *Lactobacillus* spp. and other lactic acid bacteria in the Human intestine as determined 68:114-123, 2002. by specific aplification.

Imam et al., Adhesion of Lactobacillus amylovorus to Insoluble and Derivatized Cornstarch Granules. Appl Environ Microbiol, Apr. 1991, vol. 57, No. 4, pp. 1128-1133.

Jeffrey Folmer et al., Animal Science Department—Intervention Strategies for Reduction of *E. coli* O157:H7 in Feedlot Steers. 2003.

Joseph, Flint and Esther, Angert, Journal of Microbiological Methods, Devlopment of a strain-specific assay for detection of viable *Lactobacillus* sp. HOFG1. 61:235-243, 2005.

Jun. 6, 2005 GRAS Notification by Nutrition Physiology Corporation, available at http://www.accessdata.fda.gov/scripts/fcn/gras_notices/grn_171.pdf.

Kaila Kailasapathy; Microencapsulation of pro biotic bacteria: Technology and potential application; Curr. Issues Intest. Microbiol. (2002) 3; 39-48.

Linders, L. J. M.; Kets, E. P. W.; de Bont, J. A. M.; van't, R. K. Combined influence of growth and drying conditions on the activity of dried Lactobacillus plantarum. Biotechnol. Prog. 1998, 14: 537-539.

Mary, P., Ochin, D., Tailliez, R., 1986. Growth status of Rhizobia in relation to their tolerance to low water activities and desiccation stresses. Soil Biology and Biochemistry 18: 179-184.

Mauriello et al., J. Food Prot., ; Spray-Drying of bacteriocin-producing lactic acid bacteria ; 62: 773-777, 1999.

Morgan CA, Herman N, White PA, Vesey G. 2006. Preservation of micro-organisms by drying; a review. J Microbiol Methods 66: 183-93.

O'Riordan et al., J. Appl. Microbiol., ; Evaluation of microencapsulation of bifidobacterium strain with starch as an approach to prolonging viability during storage. 91:1059-1066, 2001.

Pat Casey et al.; A Five Strain Probiotic Combination Reduces Pathogen shedding and alleviates disease signs in pigs challenged with *Salmonella enterica* serover typhimurium; Applied and Environmental Microbiology; p. 1858-1863; vol. 76, No. 6.

Pyoung, II Kim er al.; Probiotic properties of Lactobacillus and Bifidobacterium strains isolated from 2007—pp. 1103-1111.

Roberfroid, M.B., Am. J. of Clin. Nutr. 71: ; Prebiotics and probiotics: are they functional foods1682S-1687S, 2001.

Santivarangkna, Chalat, U. Kulozik, and P. Foerst. 2007. Alternative drying processes for the industrial preservation of lactic acid started cultures. Biotechnol Prog 23: 302-315.

Stevens; Prevalence of O157 on Steers with various dose of LA 51. vol. 70, No. 5; 2007; pp. 1252-1255.

Teixeira, P.C., Castro, M.H., Malcata, F.X., Kirby, R.M., 1995. Survival of *Lactobacillus delbruckii* ssp. *bulgaricus* following spray drying. Journal of Dairy Science 78: 1025-1031.

Tsen et al., Survival of freeze-dried Lactobacillus acidophilus immobilized in k-carrageenan gel. J. Gen. Appl. Microbiol., Aug. 2002, vol. 48, No. 4, pp. 237-241.

Zárate et al., Viability and biological properties of probiotic vaginal lactobacilli after lyophilization and refrigerated storage into gelatin capsules. Process Biochemistry, Aug. 2006, vol. 41, No. 8, pp. 1779-1785.

* cited by examiner

Left Y Axis: Culture Optical Density (OD600)

Right Y Axis: Viable Cell Concentration (CFU/ml)

Left Y Axis: Culture Optical Density (OD600)

Right Y Axis: Viable Cell Concentration (CFU/ml)

Left Y Axis: Culture Optical Density (OD600)

Right Y Axis: Viable Cell Concentration (CFU/ml)

Left Y Axis: Culture Optical Density (OD600)
Right Y Axis: Viable Cell Concentration (CFU/ml)

Left Y Axis: Culture Optical Density (OD600)

Right Y Axis: Viable Cell Concentration (CFU/ml)

PROCESS AND COMPOSITION FOR MANUFACTURE OF A MICROBIAL-BASED PRODUCT

This application is a continuation of U.S. patent application Ser. No. 12/976,490 filed on Dec. 22, 2010, which is a continuation in part application of U.S. patent application Ser. No. 12/772,137, now U.S. Pat. No. 7,888,062, filed on Apr. 30, 2010, which claims priority to United States provisional patent application 61/300,301, filed on Feb. 1, 2010, where all of the aforementioned applications and patents are incorporated by reference in their entirety herein without disclaimer.

The sequence listing, containing the file named 8154_018_NPUS00_ST25.txt which comprises the DNA sequences of the gene expression elements of the present disclosure, is 3 KB, was created on Apr. 30, 2010, and is hereby incorporated by reference in its entirety.

BACKGROUND

1. Field

The present disclosure relates to methods and compositions for culturing bacteria. More specifically, the disclosure relates to methods for culturing lactic acid producing microorganisms and formulations for using such microorganisms in the inhibition of pathogenic growth.

2. Description of the Related Art

Beneficial bacteria colonize the intestinal tracts of mammals and can promote the well being of the host. The consumption of exogenous bacteria, often referred to as probiotics, can elicit beneficial effects upon a host. In humans, these probiotic bacteria have been shown to reduce the severity and duration of rotaviral-induced diarrhea, alleviate lactose intolerance, and enhance gastrointestinal immune function (Roberfroid 2000).

Traditionally, food sources such as yogurt have been considered probiotic-carriers providing these health-promoting benefits. It is believed that the consumption of foods rich in probiotic bacteria, including lactic acid bacteria and bifidobacteria, leads to colonization of the human gastrointestinal tract of humans (Roberfroid 2000). The addition of probiotic microorganisms to animal feed can improve animal efficiency and health. Specific examples include increased weight gain-to-feed intake ratio (feed efficiency), improved average daily weight gain, improved milk yield, and improved milk composition by dairy cows as described by U.S. Pat. Nos. 5,529,793 and 5,534,271 issued to Garner and Ware. The administration of probiotic organisms can also reduce the incidence of pathogenic organisms in cattle, as reported by U.S. Pat. No. 7,063,836 issued to Garner and Ware.

Researchers have demonstrated that the consumption of probiotics by animals used in food production can improve the efficiency of animal production. Propionic acid is important in ruminal and intestinal fermentations and is a precursor to blood glucose synthesis (Baldwin 1983). Several examples are available that demonstrate the positive impact of feeding propionic acid-producing organisms to cattle. For example, U.S. Pat. Nos. 5,529,793 and 5,534,271, issued to Garner and Ware, along with U.S. Pat. Nos. 6,455,063 and 6,887,489, issued to Rehberger et al., teach of the beneficial effects that propionic acid-producing bacteria have upon cattle growth. Lactic acid bacteria (LAB) can inhibit pathogens in various food sources. Brashears et al., 2003. Lactic acid producing and lactate utilizing bacteria may also be helpful in inhibiting pathogenic growth in animals and improving the production of dairy products. U.S. Pat. No. 7,063,836. Lactic acid producing and lactate utilizing bacteria are beneficial for the utilization of feedstuffs by ruminants (U.S. Pat. Nos. 5,529,793 and 5,534,271) and have been fed to cattle to improve animal performance. Brashears et al., 2003.

*Lactobacillus* is the most prevalently administered probiotic bacteria. Flint and Angert 2005. *Lactobacillus* is a genus of more than 25 species of gram-positive, catalase-negative, non-sporulating, rod-shaped organisms. Heilig et al., 2002. *Lactobacillus* ferment carbohydrates to form lactic acid. U.S. Pat. No. 7,323,166. They are generally anaerobic, non-motile, and do not reduce nitrate. U.S. Pat. No. 7,323,166. *Lactobacillus* are often used in the manufacture of food products including dairy products and other fermented foods. Heilig et al., 2002; U.S. Pat. No. 7,323,166. These organisms inhabit various locations including the gastrointestinal tracts of animals and intact and rotting plant material. Heilig et al., 2002; U.S. Pat. No. 7,323,166. *Lactobacillus* strains appear to be present in the gastrointestinal tract of approximately 70% of humans that consume a Western-like diet. Heilig et al., 2002. The number of *Lactobacillus* cells in neonates is approximately 105 colony forming units (CFU) per gram CFU/g of feces. Heilig et al., 2002. The amount in infants of one month and older is higher, ranging from $10^6$ to $10^8$ CFU/g of feces. Heilig et al., 2002.

For use as a probiotic, a LAB needs to be able remain viable during processing and storage protocols such as centrifugation, filtration, fermentation, freeze drying or lyophilization in which the LAB may be subjected to freezing, high pressure, and high temperature. U.S. Pat. No. 7,323,166.

Various factors affect the viability of bacteria. Cells are preferably harvested while actively growing in either the logarithmic or early stationary phase with a density of about $10^8$/ml. U.S. Pat. No. 7,323,166. The preservation medium should contain a cryoprotectant such as skim milk, sucrose, serum, inositol, or dextran. U.S. Pat. No. 7,323,166. The preferred cryoprotectant may vary based on the cells to be lyophilized. U.S. Pat. No. 7,323,166.

Probiotics may work by competitive exclusion in which live microbial cultures act antagonistically on specific organisms to cause a decrease in the numbers of that organism. U.S. Pat. No. 7,323,166. Mechanisms of competitive exclusion include production of antibacterial agents (bacteriocins) and metabolites (organic acids and hydrogen peroxide), competition for nutrients, and competition for adhesion sites on the gut epithelial surface. U.S. Pat. No. 7,323,166.

Any substance that is intentionally added to food is considered a food additive and must reviewed and approved by the FDA unless the substance is generally recognized as be in safe. The use of a food substance may be GRAS either through scientific procedures or through experience based on common use in food if the substance was used in food before 1958. (The Federal Food, Drug, and Cosmetic Act (the Act) sections 201(s) and 409 and the FDA's implementing regulations in 21 CFR 170.3 and 21 CFR 170.30; see www.fda.gov/Food/FoodIngredientsPackaging/GenerallyRecognizedasSafeGRAS/default.htm.).

The FDA Office of Premarket Approval lists microorganisms that are Generally Recognized as Safe (GRAS) as food additives. Food additives derived from microorganisms that are classified as Generally Recognized as Safe are listed in 21 CFR 170. The FDA has stated that it has no questions regarding the conclusion that a LAB mixture consisting of *L. acidophilus* (NP35, NP51), *L. lactis* (NP7), and *P. acidilactici* (NP3), is GRAS under the intended conditions of use. www.fda.gov/Food/FoodIngredientsPackaging/GenerallyRecognizedasSafeGRAS/GRASListing s/ucm154589.htm and www.fda.gov/Food/FoodIngredientsPackaging/GenerallyRecognizedasSafeGRAS/GRASListings/ucm154102.htm.

Growing conditions for *Lactobacillus acidophilus* are included in the Jun. 6, 2005 GRAS Notification by Nutrition Physiology Corporation. Jun. 6, 2005 GRAS Notification by Nutrition Physiology Corporation available at www.accessdata.fda.gov/scripts/fcn/gras_notices/grn_171.pdf. Bacteria, including M35, were cultured in NPC-1 media at a temperature range between 35° C. and 42° C. Glucose and lactate were added depending upon the organism. The bacteria were cultured until late stationary phase. The bacteria were concentrated by filtration through a 0.2 micrometer filter system and freeze dried. The freeze dried product was ground into a homogenous powder and stored at −80° C. The powder was mixed with a carrier, the viable cell count determined, and the product was packaged for shipment.

Various strains of LAB were isolated from healthy cattle by plating fecal material on LBS agar and MRS agar plates and placing isolated colonies in MRS broth repeatedly. U.S. Pat. No. 7,323,166.

The application of microorganisms to feed-stuffs is gaining world-wide popularity. Certain direct-fed microbials (DFM) mode of action require cells to be viable to be beneficial to a host. Many DFM products available rapidly lose viable cells and often contain insufficient viable cell concentrations to elicit a positive impact upon the host. Thus, there is need for more efficient methods to produce bacteria that are able to retain a high level of viability and stability during the fermentation and preservation processes.

Corcoran et al. found that *Lactobacillus rhamnosus* had a greater level of survivability after freeze-drying when the cells were harvested in stationary phase. Cells harvested during log phase demonstrated a 14% survival, while cells harvested in stationary phase showed a 50% survival rate. Correspondingly, the stability of the freeze-dried organisms was also dependent upon the stage of growth harvested. Cells harvested during log phase showed lower levels of stability at incubation temperatures of 4° C., 15° C., and 37° C. than cells harvested during lag or stationary phases.

Mary et al., 1986, found similar results to Corcoran et al., 2004, when evaluating *Rhizobium meliloti*. Cells harvested during stationary phase showed greater levels of survivability than cells harvested from early-, mid-, or late-log phases.

Fu and Etzel, 1995, evaluated the survival of *Lactococcus lactis* using different parameters during spray drying of the culture. They reported harvesting the cells in early-stationary phase but did not comment on why they chose that time point or whether they had previously evaluated different times in the growth to harvest the cells.

Teixeira et al., 1995, state that *Lactobacillus* harvested during log phase are more sensitive to treatments such as spray drying. They demonstrated that *Lactobacillus bulgaricus* cells harvested during stationary phase had greater levels of survival during spray drying than cells harvested during log growth.

Linders et al., 1998, evaluated the influence of growth and drying conditions upon production of dried *Lactobacillus plantarum*. They described harvesting the cells 4 hours into stationary phase which resulted in cells with a higher drying tolerance than cells harvested during the log phase of growth.

With regards to stability of different sized cells during preservation, Bozoglu et al., 1987, reported that smaller cells that are closer to spherical in shape, like *Streptococcus*, are more resistant to freeze-drying than longer, rod shape cells like *Lactobacillus*.

Champagne and Gardner reported that the concentration of the fermentable carbon source affected viability of lyophilized *Leuconostoc mesenteroides*. Cells were grown in either 110 mM (19.8 g/L) or 220 mM (39.6 g/L) glucose in MRS. Cells grown in 110 mM glucose reached $3.6 \times 10^9$ cells/ml while cells grown with 220 mM glucose reached $7.0 \times 10^9$ cells/ml. Although the cells grown with 220 mM glucose achieved greater cells yields, the resulting freeze-dried cultures contained $4.7 \times 10^{10}$ cfu/g for cells grown in 110 mM glucose and $3.6 \times 10^{10}$ cfu/g for cells grown with 220 mM glucose.

Production of microorganisms is a costly process. Modifications in production that increase cellular yield and retain cell viability can have a dramatic impact upon the profitability of DFM administration. Therefore, further advancement in fermentation technologies are actively sought and needed to maintain a high level of product stability, consumer confidence, and increased profitability for the direct fed microbial industry.

SUMMARY

The present disclosure describes a new process for the production of certain probiotic bacteria.

In certain embodiments of the disclosure, the methods herein related to a method of manufacturing a composition comprising probiotic bacteria by inoculating a fermentation medium and harvesting the probiotic bacteria at a certain time point based on the bacterial growth curve when the cells are at a particular concentration.

In certain embodiments of the disclosure relates to concentrating the harvested probiotic bacteria.

In certain embodiments, the disclosure relates to preserving the probiotic bacteria. In certain embodiments wherein preservation is contemplated, the preservation may be by encapsulation, by refrigeration, by lyophilization, by freezing or some combination thereof wherein the cells are at a certain concentration.

In particular embodiments, the bacteria can be any live probiotic bacteria or bacterial cells or in certain instances simply called cells. For example, the bacteria can be *Bacillus subtilis, Bifidobacterium adolescentis, Bifidobacterium animalis, Bifidobacterium bifidum, Bifidobacterium infantis, Bifidobacterium longum, Bifidobacterium thermophilum, Lactobacillus acidophilus, Lactobacillus agilis, Lactobacillus alactosus, Lactobacillus alimentarius, Lactobacillus amylophilus, Lactobacillus amylovorans, Lactobacillus amylovorus, Lactobacillus animalis, Lactobacillus batatas, Lactobacillus bavaricus, Lactobacillus bifermentans, Lactobacillus bifidus, Lactobacillus brevis, Lactobacillus buchnerii, Lactobacillus bulgaricus, Lactobacillus catenaforme, Lactobacillus casei, Lactobacillus cellobiosus, Lactobacillus collinoides, Lactobacillus confusus, Lactobacillus coprophilus, Lactobacillus coryniformis, Lactobacillus corynoides, Lactobacillus crispatus, Lactobacillus curvatus, Lactobacillus delbrueckii, Lactobacillus desidiosus, Lactobacillus divergens, Lactobacillus enterii, Lactobacillus farciminis, Lactobacillus fermentum, Lactobacillus frigidus, Lactobacillus fructivorans, Lactobacillus fructosus, Lactobacillus gasseri, Lactobacillus halotolerans, Lactobacillus helveticus, Lactobacillus heterohiochii, Lactobacillus hilgardii, Lactobacillus hordniae, Lactobacillus inulinus, Lactobacillus jensenii, Lactobacillus jugurti, Lactobacillus kandleri, Lactobacillus kejir, Lactobacillus lactis, Lactobacillus leichmannii, Lactobacillus lindneri, Lactobacillus malefermentans, Lactobacillus mali, Lactobacillus maltaromicus, Lactobacillus minor, Lactobacillus minutus, Lactobacillus mobilis, Lac-* tobacillus murinus, *Lactobacillus pentosus, Lactobacillus plantarum, Lactobacillus pseudoplantarum, Lactobacillus reuteri, Lactobacillus rhamnosus, Lactobacillus rogosae, Lactobacillus tolerans, Lactobacillus torquens, Lactobacillus ruminis, Lactobacillus sake, Lactobacillus salivarius, Lactobacillus sanfrancisco, Lactobacillus sharpeae, Lactobacillus trichodes, Lactobacillus vaccinostercus, Lactobacillus viridescens, Lactobacillus vitulinus, Lactobacillus xylosus, Lactobacillus yamanashiensis, Lactobacillus zeae, Pediococcus acidlactici, Pediococcus pentosaceus, Streptococcus cremoris, Streptococcus diacetylactis, Streptococcus faecium, Streptococcus intermedius, Streptococcus lactis, Streptococcus thermophilus, Propionibacterium freudenreichii, Enterococcus faecium, Propionibacterium acidipropionici* and combinations thereof. Furthermore, a lactic acid-producing microorganism can be a strain of *Lactobacillus* spp., such as the MRL1, M35, LA45, L411, NPC747, NPC750, D3, and L7 strains. In one embodiment, the lactic acid producing bacterium is *Lactobacillus amylovorus*, which is also known as M35, *Lactobacillus crispatus* M35, *Lactobacillus acidophilus* M35, NP35 (NP-35), NPC750 (NP-750) and ATCC PTA-5249 (submitted to American Type Culture Collection, Manassas, Va. on May 25, 2005).

In certain embodiments wherein harvesting at a particular bacterial phase of growth is contemplated, the growth may be early log, mid-log, late log or early stationary phase or somewhere in between early log and early stationary phase. In particular embodiments, the harvesting is between mid log and late log phase of growth.

The concentration of the live cells at the time of harvesting may be at a concentration of $1\times10^6$ to $1\times10^{12}$ cells/ml or greater. In certain embodiments, the cells are harvested at a concentration at least or greater than or equal to $1\times10^9$ cells/ml. In certain embodiments, the cells are harvested at a concentration of at least or greater than or equal to $7.5\times10^8$ cells/ml.

In certain embodiments wherein the live probiotic bacteria are harvested, the composition comprising the probiotic bacteria may be concentrated. In certain embodiments, the concentration is by centrifugation or ultrafiltration, in other embodiments the concentration is by sedimentation. In certain embodiments wherein the live cells are concentrated, the cells are concentrated to a live cell count of at least or greater than or equal to $7.5\times10^8$ cells/ml. In preferred embodiments the cells are concentrated to a live cell count of at least or greater than or equal to $5\times10^9$ cells/ml.

In embodiments wherein the composition of live cells is preserved, the preserving may result in a dry composition or powder through preservation by lyophilization, or spray drying. In such embodiments, the cell or probiotic bacteria density may be within the range of $1\times10^8$ colony forming units (cfu)/g to $1\times10^{12}$ cfu/g. In certain embodiments, the density is at least or greater than or equal to $1\times10^{10}$ cfu/g.

In embodiments wherein the composition is preserved by freezing, cell or probiotic density may be within the range of $1\times10^8$ colony forming units per ml to $1\times10^{10}$ cfu/ml. In embodiments wherein the composition is preserved by freezing, the density is at least or greater than $5\times10^9$ cfu/g.

In embodiments wherein the composition is preserved by refrigeration, cell or probiotic density may be within the range of $1\times10^8$ colony forming units per ml to $1\times10^{10}$ cfu/ml. In embodiments wherein the composition is preserved by refrigeration, the density is at least or greater or equal to $5\times10^9$ cfu/g.

In embodiments of the disclosure, one cfu may equal one live cell.

Certain embodiments contemplate a composition of live cells produced by harvesting at a particular bacterial phase of growth, the growth may be early log, mid-log, late log or early stationary phase or somewhere in between early log and early stationary phase. In particular embodiments, the harvesting is between mid log and late log phase of growth. Still further, the composition of live cells may at the time of harvesting may be at a concentration of $1\times10^6$ to $1\times10^{12}$ cells/ml or greater. In certain embodiments, the composition of live cells is a composition wherein the cells are harvested at a concentration at least or greater than or equal to $1\times10^9$ cells/ml. In certain embodiments, the cells are harvested at a concentration of at least or greater than or equal to $7.5\times10^8$ cells/ml.

In certain embodiments, the disclosure contemplates that a composition of live cells are incorporated into a direct fed microbial product or DFM. It is further contemplated that the DFM may be administered to any animal. In certain embodiments, the animal may be a ruminant animal. In certain embodiments, DFM may be administered to poultry. In certain embodiments, the DFM may be administered to swine. In certain embodiments, the DFM may be administered to a companion animal.

In certain embodiments, the composition of live cells is incorporated into water for animals, such as water for drinking or for rinsing of an animal holding area such as a hen house or cattle stall or for nebulizing to allow interaction with an animals respiratory tract. In certain embodiments, the composition of live cells may be incorporated into water from cells that were first lyophilized, refrigerated, frozen or encapsulated. In certain embodiments the composition of live cells is applied to food preparation surfaces. Food preparation surfaces may include kitchen counters, sinks, utensils, appliance exteriors or appliance interiors. In certain embodiments, the composition of live cells is applied to food preparation areas by electrostatic spray. In other embodiments, the composition of live cells is applied to food preparation areas by nebulization. In other embodiments, the composition of live cells is applied to food preparation surfaces as a liquid. In certain embodiments, the liquid containing the composition of live cells is brushed or wiped or sprayed onto the food preparation surface. In embodiments wherein lyophilized compositions are contemplated, the lyophilized composition may be sprayed or shaken from a container or dusted or brushed onto a food preparation area.

In certain embodiments, the composition of live cells is applied to fruits, vegetables or grains. In some embodiments, the composition of live cells is applied to fruits, vegetables or grains by nebulization or liquid spray. In other embodiments, the composition of live cells is applied to fruits, vegetables or grains as a liquid by wiping or brushing the liquid onto the fruits, vegetables or grains. In embodiments wherein lyophilized compositions are contemplated, the lyophilized composition may be sprayed or shaken from a container or dusted or brushed onto fruits, vegetables or grains.

In certain embodiments, the composition of live cells is applied to meat, either before or after cooking. In some embodiments, the composition of live cells is applied to meat by nebulization or liquid spray. In other embodiments, the composition of live cells is applied to meat as a liquid by wiping or brushing the liquid onto the meat. In embodiments wherein lyophilized compositions are contemplated, the lyophilized composition may be sprayed or shaken from a container or dusted or brushed onto meat.

Consistent with long standing patent law, the words "a" and "an" denote "one or more," when used in the text or claims of this specification in conjunction with the word "comprising" or where the context of the usage suggests that, from either a grammatical or scientific standpoint, these words should so denote.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

Figure 1:
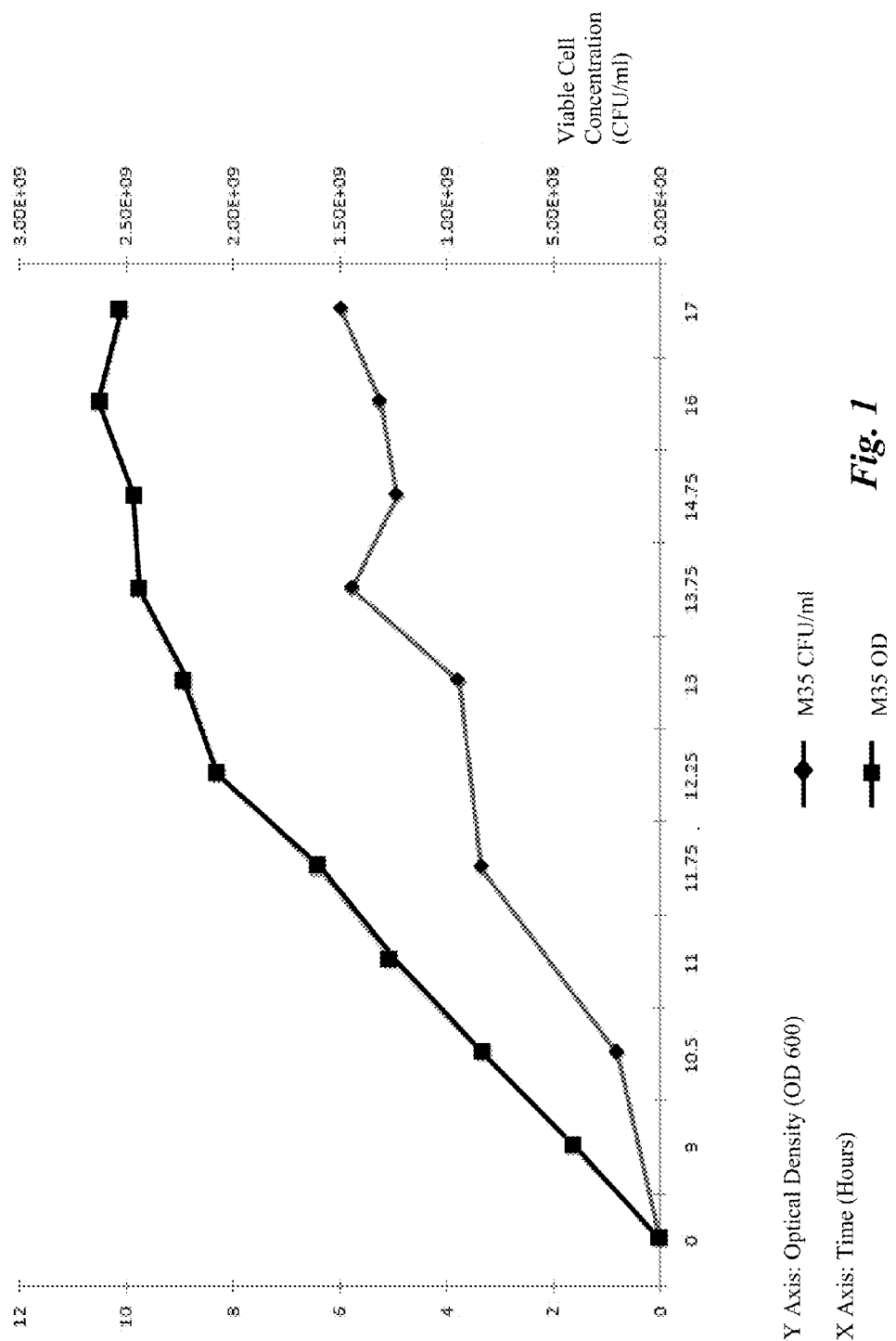
FIG. 1. Graph showing *L. amylovorus* M35 culture optical density and viable cell concentration under fermentation conditions.

DETAILED DESCRIPTION OF THE ILLUSTRATIVE EMBODIMENTS a. Terminology

In this specification and the claims that follow, reference will be made to a number of terms which may be considered to have the following meanings:

Throughout the specification and claims, the word "comprise" and variations of the word, such as "comprising" and "comprises," means "including but not limited to," and is not intended to exclude, for example, other additives, components, integers, or steps.

By "reduce" or other forms of the word, such as "reducing" or "reduction," in certain instances may mean lowering of an event or characteristic (e.g., microorganism growth or survival). It is understood that this is typically in relation to some standard or expected value, in other words it is relative, but that it is not always necessary for the standard or relative value to be referred to. For example, "reduces the population of bacteria" means lowering the amount of bacteria relative to a standard or a control.

By "treat" or other forms of the word, such as "treated" or "treatment," in certain instances may mean to administer a composition or to perform a method in order to reduce, prevent, inhibit, break-down, or eliminate a particular characteristic or event (e.g., microorganism growth or survival).

As used herein, the term "viable cell" in certain instances may refer to a microorganism that is alive and capable of regeneration and/or propagation, while in a vegetative, frozen, preserved, or reconstituted state.

As used herein, the term "viable cell yield" or "viable cell concentration" in certain instances may refer to the number of viable cells in a liquid culture, concentrated, or preserved state per a unit of measure, such as liter, milliliter, kilogram, gram or milligram.

As used herein, the term "cell preservation" in certain instances may refer to a process that takes a vegetative cell and preserves it in a metabolically inert state or low metabolic state compared to the organisms normal metabolic state that retains viability over time. As used herein, the term "product" in certain instances may refer to a microbial composition that can be blended with other components and contains specified concentration of viable cells that can be sold and used.

As used herein, the terms "microorganism" or "microbe" in certain instances may refer to an organism of microscopic size, to a single-celled organism, and/or to any virus particle. Our definition of microorganism includes Bacteria, Archaea, single-celled Eukaryotes (protozoa, fungi, and ciliates), and viral agents. The term "microbial" in certain instances, may be used herein to describe processes or compositions of microorganisms, thus a "microbial-based product" may be a composition that includes microorganisms, cellular components of the microorganisms, and/or metabolites produced by the microorganisms. Microorganisms can exist in various states and occur in vegetative, dormant, or spore states. Microorganisms can also occur as either motile or non-motile, and may be found as planktonic cells (unattached), substrate affixed cells, cells within colonies, or cells within a biofilm.

As used herein, the term "probiotic" in certain instances may refer to one or more live microorganisms that confer beneficial effects on a host organism. Benefits derived from the establishment of probiotic microorganisms within the digestive tract include reduction of pathogen load, improved microbial fermentation patterns, improved nutrient absorption, improved immune function, aided digestion and relief of symptoms of irritable bowel disease and colitis.

As used herein, the term "gastrointestinal tract" in certain instances may refer to the complete system of organs and regions that are involved with ingestion, digestion, and excretion of food and liquids. This system generally consists of, but not limited to, the mouth, esophagus, stomach and or rumen, intestines (both small and large), cecum (plural ceca), fermentation sacs, and the anus.

As used herein, "pathogen" in certain instances may refer to any microorganism that produces a harmful effect and/or disease state in a human or animal host.

As used herein, the term "fermentation" in certain instances may refer to a metabolic process performed by an organism that converts one substrate to another in which the cell is able to obtain cellular energy, such as when an organism utilizes glucose and converts it to lactic acid or propionic acid. Many of the end-substrates formed in fermentation processes are volatile fatty acids.

As used herein, the phrase "volatile fatty acids" in certain instances may refer to short-chain fatty acids containing six or fewer carbon atoms and at least one carboxyl group. Some examples of VFAs include, but are not limited to: lactic acid, acetic acid, propionic acid, butyric acid, isobutyric acid, valeric acid, and isovaleric acid, which are products of microbial fermentation within the digestive tracts of animals. Volatile fatty acids can be absorbed through the intestines of animals and used as an energy or carbon source. Microbes produce VFAs based on available substrates and also rely upon VFAs for energy and carbon sources.

As used herein, "lactic acid" in certain instances may refer to a byproduct of glucose fermentation resulting in a three-carbon acid with the chemical formula $C_3H_6O_3$. This includes, but is not limited to, lactic acid derived from specific strains of bacteria or lactic acid derived from other types of organisms. Lactic acid can be microbialstatic, microbialcidal, bacteriostatic, bacteriocidal or bacteriolytic; these concepts are known to skilled persons. "Lactic-acid producing" refers to any organism that generates lactic acid.

b. Introduction

A method of producing a bacterial strain under closely monitored and controlled growth conditions is disclosed herein. The conditions are controlled to encourage luxurious growth and encourage maximal viable cell recoveries in downstream processes. The fermented microorganism can be harvested at a predetermined time or stage of growth. Preferably, the microorganism is harvested in early log-phase, mid log-phase, late log-phase, or early stationary phase. Preferably the calls are harvested at a time that the cells are not under considerable stress and have an average cellular size or smaller.

A process in which a microorganism is grown in a medium with a known composition is described herein. The growth medium has known amounts of available nitrogen and carbon sources. These nutrient sources can be modified at one time point or throughout the entire fermentation process. In this process, a microorganism or microorganism may be exposed to known stressors. The time, duration, and parameters of each stressor are controlled. Such parameters include exposure of the cells to certain acid concentrations, medium pH and temperature. The fermentation operator can modify these conditions or they can be allowed to generate as a result from the normal fermentation processes of the microorganism. These parameters can be modified to enhance the growth and/or survivability of the microorganism.

Beneficial bacteria can be used to inhibit pathogenic growth by treating waste products, food and food preparation areas in addition to being added to human food sources and animal feed. It is important that these bacterial compositions have adequate cell viability.

There are a number of environmental stresses that can have a dramatic impact upon microorganism growth, survival and viability. For instance, the concentration of acid present in the growth medium can adversely affect a bacterial culture. The concentration of acids influences the pH of a given culture, which may have a profound impact on microbial metabolism. The presence of too low a pH or too great a concentration of acids can in certain instances lead to poor cell growth and eventual cell death. Likewise, salinity is an important parameter for microorganism growth, survival and viability. Salinity concentrations outside of the tolerable range of a bacterial culture can also result in poor growth and poor cellular morphology. Temperature is another factor to consider in the culturing of microorganisms. All microorganisms have an optimal growth temperature. Temperatures that are above or below an optimal level may result in altered microbial metabolism and altered gene expression. For example high or low temperatures may induce bacteria in cultures to go into a state of shock and express genes responsible for cell maintenance under such stressful conditions.

In addition to pH, saline and temperature, bacterial cultures require a number of nutrients for proper growth. Depletion of the required nutrients typically results in cell starvation, poor growth, instability and eventual death. For instance, depletion of nitrogen such as from amino acids or proteins results in cells in culture expressing stress related genes which in turn result in wasted energy, poor cell morphology and stability and eventual cell death Likewise, the incorporation of too much nutrition has adverse effects upon microbial growth and stability. For instance, the addition of too much sugar carbohydrate as a carbon source results in cellular alteration of gene expression, which in turn may result in poor growth, wasted energy, nutrient waste and poor stability.

While maximum possible growth rate of a microorganism is a primary goal of the bacterial fermentation process in many applications, a process control method may be used when it is desired to maintain a growth rate that is lower than the maximum or in cases where excess substrate may be metabolized to toxic or undesired byproducts. Thus, a method for better control of the fermentation environment is needed. In short, a central goal in fermentation process engineering is to optimize a process for producing viable microorganisms by controlling growth, metabolism and toxic or undesired byproducts. In this way, the microorganism yield can be improved or optimized for a process or a phase of the process and the batch-to-batch consistency can be improved.

Figure 4:
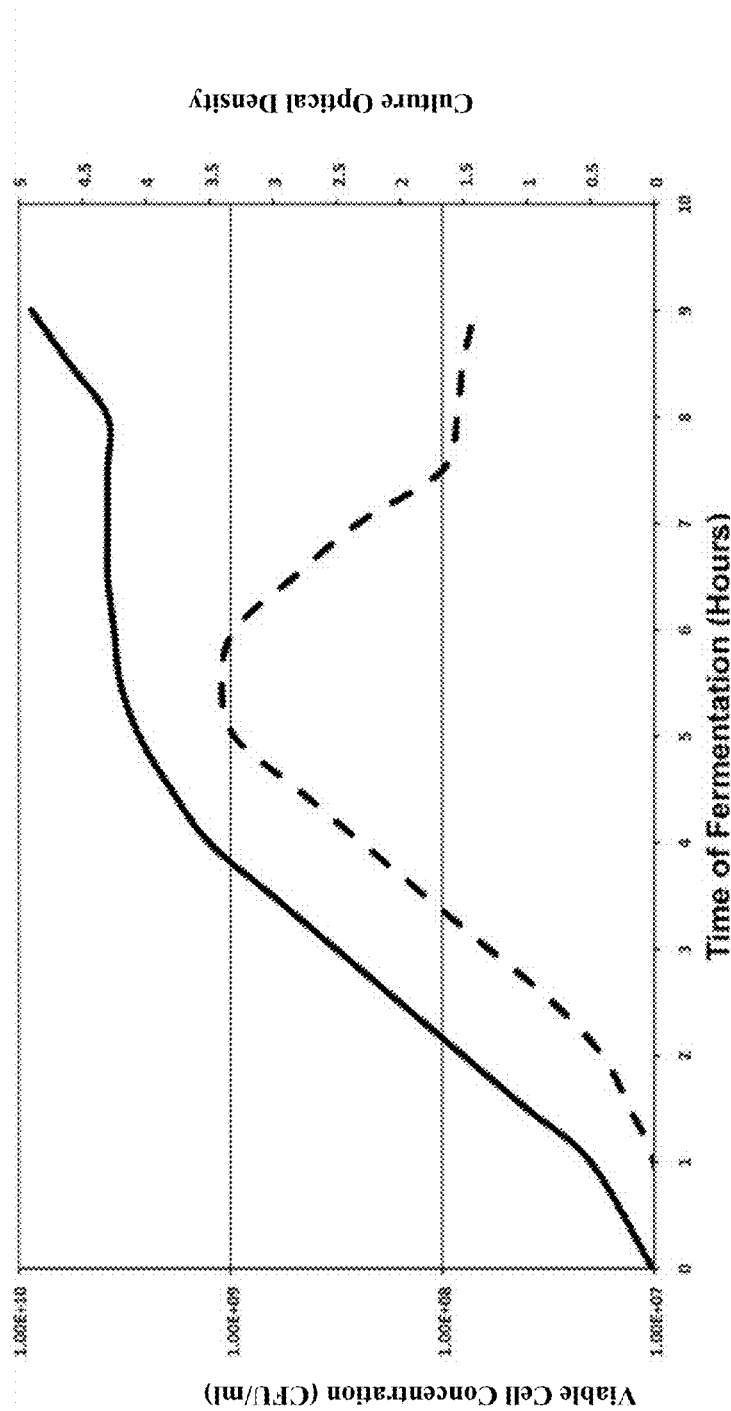
FIG. 4. Graph demonstrating relationship between culture optical density and viable cells during growth, not specifically indicative of the bacterial species or strains mentioned herein.

The goal of many fermentation runs is to obtain the highest quantity of viable cells possible. Two exemplary parameters that may be used to monitor microorganism growth during fermentation are the related measurements of culture optical density (OD) and viable cell concentration. In many instances, bacterial cell walls absorb light wavelengths at 600 nm (OD600). Consequently, one can use a spectrophotometer and measure the absorbance that the culture has at 600 nm. An increase in absorbance can be correlated in many instances to the concentration of cells in the culture. However, optical density is not a direct measurement of cell viability. FIG. 4. Increases in bacterial material do no accurately reflect viable cells. Upon entering stationary phase, cell growth slows and cells die. This becomes more rampant as metabolites increase in the surrounding medium. The contrast between optical density and viable cellular yield is due to dead cells. As cellular death is induced in the late stages of fermentation, the dead cells remain mostly intact because lysogenic enzymes have become inactive that stage of fermentation. Other cells are continuing to reproduce at a slow rate. Therefore the number of viable cells may be less than the number of cells that would be predicted by the optical density alone. Cell viability can be determined by serial dilution of the culture and plating onto a solid growth medium. As used herein, the term "viable cell" refers to a microorganism that is alive and capable of regeneration and/or propagation while in a vegetative, frozen, preserved or reconstituted state. As used herein, the term "viable cell yield" or "viable cell concentration" refers to the number of viable cells in a liquid culture, concentrated, or in a preserved state per unit of measure.

Factors such as toxic by-products, energy spilling, cell death, changes in cell morphology (e.g., cell elongation), and salinity can confound optimal bacterial growth during production. For example, microorganisms are capable of producing by-products that may be inhibitory to their own growth, and/or may be toxic to other cell populations. For instance, lactobacilli during fermentative metabolism generate lactic acid as a by-product, which is extremely toxic in high concentrations. Accumulation of these acids within the fermentation medium leads to decreased growth rates and limits the cellular yields obtained during a fermentation run. The detrimental effects imposed by lactic acid production may be partially alleviated through the addition of a base. Sodium hydroxide is a commonly used strong basic compound used to neutralize media since it is inexpensive and readily soluble in water. However, other bases such as ammonium hydroxide, potassium hydroxide, and ammonia can also be used. Other pH buffering compounds can be used including calcium carbonate, sodium carbonate, sodium bicarbonate, carbonate salts, and other organic materials.

Another factor limiting cellular yields during fermentation is known as "energy spilling". This phenomenon has been described for many bacteria, including lactic acid bacteria. Energy spilling refers to the process whereby cells acquire nutrients from the growth medium and utilize them for metabolic processes, yet do not increase in size or propagate. Energy spilling can occur upon exposure to antibiotics or during starvation due to an amino acid deficiency. The nutrients are utilized for the generation of cellular energy, but limiting nutrients require the cell to convert the energy into other compounds, thus wasting potential energy.

Another mechanism responsible for the contrast between culture optical density and viable cellular yield is cellular death. As mentioned above, the accumulation of metabolic byproducts inhibits cellular growth and induces cellular death in late stages of fermentation. However, these cells remain mostly intact because normal lysogenic enzymes also become inactive at these late stages of fermentation. Some cells do still continue to reproduce, albeit at a slow rate. As these cells divide and others die, resulting in an increase in culture optical density, yet yield static level of viable cells.

Bacteria can also change their morphology, especially when exposed to stressful conditions such as low pH, high salinity, or high levels of by-products. As mentioned above, during fermentation conditions high levels of by-products are produced and accumulated in the growth medium. These levels lead to an increase of cellular surface area, sometimes through elongation of cells. Sodium hydroxide is added to the growth medium to reduce the effects of acid accumulation by neutralizing the pH. While the hydroxide ion interacts with the acid in the medium, the sodium ion remains free in solution increasing the salinity of the medium. This results in further cellular stress and leads to an increase in cellular surface area. Cell elongation increases the optical density of a culture without directly increasing cell viability. This causes a false assessment of the viability of a bacterial culture and non-optimal harvesting of cells during a fermentation run.

c. Cultured Bacteria of the Present Disclosure

Certain aspects of the disclosure include a method of producing microorganisms. Preferably, the microorganism or microorganisms are one or more species or strains of bacteria. Preferably, the one or more species or strains of bacteria are lactic acid producing bacteria. Lactic acid producing bacteria include, but are not limited to, *Bacillus subtilis, Bifidobacterium adolescentis, Bifidobacterium animalis, Bifidobacterium bifidum, Bifidobacterium infantis, Bifidobacterium longum, Bifidobacterium thermophilum, Lactobacillus acidophilus, Lactobacillus agilis, Lactobacillus alactosus, Lactobacillus alimentarius, Lactobacillus amylophilus, Lactobacillus amylovorans, Lactobacillus amylovorus, Lactobacillus animalis, Lactobacillus batatas, Lactobacillus bavaricus, Lactobacillus bifermentans, Lactobacillus bifidus, Lactobacillus brevis, Lactobacillus buchnerii, Lactobacillus bulgaricus, Lactobacillus catenaforme, Lactobacillus casei, Lactobacillus cellobiosus, Lactobacillus collinoides, Lactobacillus confusus, Lactobacillus coprophilus, Lactobacillus coryniformis, Lactobacillus corynoides, Lactobacillus crispatus, Lactobacillus curvatus, Lactobacillus delbrueckii, Lactobacillus desidiosus, Lactobacillus divergens, Lactobacillus enterii, Lactobacillus farciminis, Lactobacillus fermentum, Lactobacillus frigidus, Lactobacillus fructivorans, Lactobacillus fructosus, Lactobacillus gasseri, Lactobacillus halotolerans, Lactobacillus helveticus, Lactobacillus heterohiochii, Lactobacillus hilgardii, Lactobacillus hordniae, Lactobacillus inulinus, Lactobacillus jensenii, Lactobacillus jugurti, Lactobacillus kandleri, Lactobacillus kefir, Lactobacillus lactis, Lactobacillus leichmannii, Lactobacillus lindneri, Lactobacillus malefermentans, Lactobacillus mali, Lactobacillus maltaromicus, Lactobacillus minor, Lactobacillus minutus, Lactobacillus mobilis, Lactobacillus murinus, Lactobacillus pentosus, Lactobacillus plantarum, Lactobacillus pseudoplantarum, Lactobacillus reuteri, Lactobacillus rhamnosus, Lactobacillus rogosae, Lactobacillus tolerans, Lactobacillus torquens, Lactobacillus ruminis, Lactobacillus sake, Lactobacillus salivarius, Lactobacillus sanfrancisco, Lactobacillus sharpeae, Lactobacillus trichodes, Lactobacillus vaccinostercus, Lactobacillus viridescens, Lactobacillus vitulinus, Lactobacillus xylosus, Lactobacillus yamanashiensis, Lactobacillus zeae, Pediococcus acidlactici, Pediococcus pentosaceus, Streptococcus cremoris, Streptococcus diacetylactis, Streptococcus faecium, Streptococcus intermedius, Streptococcus lactis, Streptococcus thermophilus, Propionibacterium freudenreichii, Enterococcus faecium, Propionibacterium acidipropionici* and combinations thereof. Furthermore, a lactic acid-producing microorganism can be a strain of *Lactobacillus* spp., such as the MRL1, M35, LA45, L411, NPC747, NPC750, D3, and L7 strains. In one embodiment, the lactic acid producing bacterium is *Lactobacillus amylovorus*. In another embodiment, the *Lactobacillus amylovorus* strain is the M35 strain. In other embodiments, the lactic acid producing bacterium is *Lactobacillus reuteri, Lactobacillus agilis, Lactobacillus murinus*, or *Lactobacillus animalis*.

Any substance that is intentionally added to food is considered a food additive and must reviewed and approved by the FDA unless the substance is generally recognized as be in safe. The use of a food substance may be GRAS implementing regulations in 21 CFR 170.3 and 21 CFR 170.30; see either through scientific procedures or through experience based on common use in food if the substance was used in food before 1958. (The Federal Food, Drug, and Cosmetic Act (the Act) sections 201(s) and 409 and the FDA's www-.fda.gov/Food/FoodIngredientsPackaging/GenerallyRecognizedasSafeGRAS/default.htm.).

*Lactobacillus amylovorus* M35 has also been referred to as *Lactobacillus crispatus* M35, *Lactobacillus acidophilus* M35, NP35 (NP-35), NPC750 (NP-750), and ATCC PTA-5249. The 16S rRNA gene sequence of *Lactobacillus amylovorus* M35 is found in SEQ ID NO.: 1. M35 has been referred to as *L. acidophilus* by the API system and *L. crispatus* by 16S rRNA analysis. Brashears et al. 2003. The API system is a phenotypic characterization based upon the carbohydrate fermentation profile for the particular strain and the 16S rRNA analysis is a genotypic characterization based upon comparison of the 16S rRNA sequence with sequences in GenBank. Brashears et al. 2003. The homology of M35 to *L. crispatus* was disclosed as 98%. Brashears et al. 2003. However, the homology of M35 to *L. amylovorus* is 99.79%.

The FDA Office of Premarket Approval lists microorganisms that are Generally Recognized as Safe (GRAS) as food additives. Food additives derived from microorganisms that are classified as Generally Recognized as Safe are listed in 21 CFR 170. The FDA has no questions regarding the conclusion that a LAB mixture consisting of *L. acidophilus* (NP35, NP51), *L. lactis* (NP7), and *P. acidilactici* (NP3), is GRAS under the intended conditions of use. www.fda.gov/Food/FoodIngredientsPackaging/GenerallyRecognizedas-SafeGRAS/GRASListing s/ucm154589.htm and www-.fda.gov/Food/FoodIngredientsPackaging/GenerallyRecognizedasSafeGRAS/GRASListing s/ucm154102.htm. Growing conditions for *Lactobacillus acidophilus* are included in the Jun. 6, 2005 GRAS Notification by Nutrition Physiology Corporation. Bacteria, including M35, were cultured in NPC-1 media at a temperature range between 35° C. and 42° C. Glucose and lactate were added depending upon the organism. The bacteria were cultured until late stationary phase. The bacteria were concentrated by filtration through a 0.2 micrometer filter system and freeze dried. Jun. 6, 2005 GRAS Notification by Nutrition Physiology Corporation available at www.accessdata.fda.gov/scripts/fcn/gras_notices/grn_171.pdf.

d. Cell Culture Systems

In any cell culture system, there is a characteristic growth pattern following inoculation that includes a lag phase, an accelerated growth phase, an exponential or "log" phase, a negative growth acceleration phase and a plateau or stationary phase. The log and plateau phases give vital information about the cell line, the population doubling time during log growth, the growth rate, and the maximum cell density achieved in plateau. In the log phase, as growth continues, the cells reach their maximum rate of cell division. Numbers of cells increase in log relationship to time. During this period of most active multiplication, the logarithms of the numbers of cells counted at short intervals, plotted against time, produce a straight line. By making one count at a specified time and a second count after an interval during the log phase of growth and knowing the number of elapsed time units, one can calculate the total number of cell divisions or doublings, and both the growth rate and generation time. Within a few hours or days after the commencement of the log phase, the rate of cell division begins to decline and some of the cells begin to die. This is reflected on the growth curve by a gradual flattening out of the line. Eventually the rate of cells dying is essentially equal to the rate of cells dividing, and the total viable population remains the same for a period of time. This is known as the stationary or plateau phase and is represented on the growth curve as a flattening out of the line where the slope approaches zero. A period of negative growth, where the culture can no longer support additional growth, follows stationary phase. Remaining viable cells die off and the slope of the growth curve becomes negative. This is known as late stationary or the death phase.

Measurement of the population doubling time can be used to quantify the response of the cells to different inhibitory or stimulatory culture conditions such as variations in nutrient concentration or pH. Measurement of the population during this time also provides a good monitor of the culture during serial passage and enables the calculation of cell yields and the dilution factor required at subculture.

For most growth curves plotted on semi-log scales, the log phase of growth can be approximately represented by a linear increase in the slope of the line over time. That is, at any short interval between two points on the line of the logarithmic phase of the curve, the log of cell number is increasing in a linear fashion relative to time. Thus mid log phase can be approximately defined as the point or interval within the log phase in which the cells are dividing at their maximal rate, and the increase in logs of cell number is linear with respect to time. Late log phase can be defined as approximately the point or interval of time in which the rate of cell division has slowed, and the log of number of cells is no longer increasing in a linear fashion with respect to time. When looking at a growth curve, this area would be represented by gradual falling or flattening of the slope of the line. At early stationary phase, the rate of cell growth is decreasing and getting nearer the rate of cell death, and thus the slope of the line on the growth curve is even less than that at late log phase. At mid-stationary phase, the rate of cell growth is approximately equal to the rate of cell division and thus the line on the growth curve is relatively flat and has a slope approaching zero. It will be understood that the skilled artisan can formulate growth curves for any such cell line and identify the aforementioned regions on the curve.

e. Reactors and Processes for Suspension

In certain embodiments, large scale suspension culture of bacteria may be undertaken in a bioreactor. Instrumentation and controls for a bioreactor allow a person of skill in the art to control agitation, temperature, dissolved oxygen levels, pH, turbidity, capacitance, and nutrient levels. Two examples of suspension culture reactor designs widely used in the industry due to their simplicity and robustness of operation are a stirred reactor and an airlift reactor. Cells are grown in a stainless steel tank with a height-to-diameter ratio of 1:1 to 3:1. The culture is usually mixed with one or more agitators, based on bladed disks or marine propeller patterns. Agitator systems offering less shear forces than blades have been described. Agitation may be driven either directly or indirectly by magnetically coupled drives. Indirect drives reduce the risk of microbial contamination through seals on stirrer shafts.

The airlift reactor is also suitable for microbial culture and relies on a gas stream to both mix and oxygenate the culture. The gas stream enters a riser section of the reactor and drives circulation. Gas disengages at the culture surface, causing denser liquid free of gas bubbles to travel downward in the downcomer section of the reactor. The main advantage of this design is the simplicity and lack of need for mechanical mixing. Typically, the height-to-diameter ratio is 10:1.

Most large-scale suspension cultures are operated as batch or fed-batch processes because they are the most straightforward to operate and scale up. However, continuous processes based on chemostat or perfusion principles may also be contemplated.

A batch process is a closed system in which a typical growth profile is seen. A lag phase is followed by exponential, stationary and decline phases. In such a system, the environment is continuously changing as nutrients are depleted and metabolites accumulate. This makes analysis of factors influencing cell growth and productivity, and hence optimization of the process, a complex task. Productivity of a batch process may be increased by controlled feeding of key nutrients to prolong the growth cycle. Such a fed-batch process is still a closed system because cells, products and waste products are not removed.

In what is still a closed system, perfusion of fresh medium through the culture can be achieved by retaining the cells with a variety of devices (e.g. fine mesh spin filter, hollow fiber or flat plate membrane filters, settling tubes). Spin filter cultures can produce cell densities of approximately $5 \times 10^7$ cells/ml. A true open system and the simplest perfusion process is the chemostat in which there is an inflow of medium and an outflow of cells and products. Culture medium is fed to the reactor at a predetermined and constant rate that maintains the dilution rate of the culture at a value less than the maximum specific growth rate of the cells (to prevent washout of the cell mass from the reactor). Culture fluid containing cells and cell products and byproducts is removed at the same rate.

Another general approach to fermentation process control is the use of continuous processes. Growth and metabolism are easily controllable in continuous bioreactors such as the chemostat, the pH-stat, and the RAR-stat. The latter was disclosed by H. Shimamatsu et al., "Process for Continuous Cultivation of Protein-Producing Microorganisms," U.S. Pat. No. 4,021,304 and shown by P. Agrawal, 1989, and is also referred to as an APR-stat (acid production rate). In continuous processes, the volume is constant because fresh medium is added at the same rate that broth (medium plus biomass) is withdrawn. Because of convection (flow through the system), steady state with respect to substrate, nutrient, biomass, and product concentrations, and thus growth and metabolism, is easily attainable. Growth and metabolism are controlled through the substrate and nutrient concentrations in the fresh medium and through the dilution rate for the chemostat, the buffering capacity of the fresh medium for the pH-stat, or the RAR set point for the RAR-stat (in all continuous processes, the growth rate equals the dilution rate at steady state).

A less direct method to control growth and metabolism is to use automated at-line measurements of the substrate concentrations. An example of using this method for glucose and glutamine using liquid chromatography and an adaptive feeding algorithm is described by H. Kurokawa et al., 1994. This method has also been described for glucose using a YSI Model 2000 analyzer and an algorithm for predicting the substrate consumption rate by B. F. Bishop et al., "Process Control System for Fed-Batch Fermentation Using a Computer to Predict Nutrient Consumption," U.S. Pat. No. 5,595, 905.

Another method to control growth and metabolism is to feed the growth-limiting substrate according to an exponential schedule. However, this method is open-loop and does not have feedback, so overfeeding or underfeeding can occur at the beginning of the process if the biomass concentration is not estimated accurately, although eventually a constant growth rate may be reached.

Harvesting the bacteria at the mid log phase results in smaller and rounder bacteria than if the bacteria were harvested at a later phase of growth. Smaller and shorter M35 have a higher survival rate following freeze drying than if they are freeze-dried at a later phase when they are larger and more elongated. The goal of harvesting M35 cells is to have the smallest most circular cell possible. Growing the bacteria using a method that minimizes cell size and minimizes cell volume may result in preserved cells that retain a higher degree of survival.

Pulsing of the carbon source or other limiting nutrient at predetermined amounts restricts bacterial growth and energy expenditure so that the cells remain smaller, and therefore may increase survival during freezing or freeze drying. Additionally, adding a carbon source or other limiting nutrient at a predetermined constant rate can also restrict cellular metabolism and growth, thus resulting in smaller cellular size and improved survival in downstream processing. Additionally, adding a carbon source or other limiting nutrient a predetermined constant rate can also limit the amount of fermentation byproducts that may be toxic to the M35 cell itself and may cause the cell to lyse during the fermentation process and may cause the cell to lose viability during or after freeze drying.

Ultrafiltration is a pressure modified convective process that uses semi-permeable membranes to separate species by molecular size, shape and/or charge. It separates solvents from solutes of various sizes independent of solute molecular size. Ultrafiltration is gentle, efficient and can be used to simultaneously concentrate and desalt solutions. Ultrafiltration membranes generally have two distinct layers: a thin, dense skin and an open structure of progressively larger voids which are largely open to the permeate side of the ultrafilter. Any species capable of passing through the pores of the skin can therefore freely pass through the membrane. For maximum retention of solute, a membrane is selected that has a nominal molecular weight cut-off well below that of the species being retained. In macromolecular concentration, the membrane enriches the content of the desired biological species and provides filtrate cleared of retained substances. Microsolutes are removed convectively with the solvent. As concentration of the retained solute increases, the ultrafiltration rate diminishes.

Other methods of separation of fermentation or culture media from bacteria, such as concentrating bacteria, include centrifugation and sedimentation.

Generally, a sedimentation process occurs by gravity and/or flotation after a sufficient amount of time, generally 2 to 12 hours. Alternatively, more rapid separations of the microorganisms and effluent may be achieved by centrifugation, continuous separation (continuous centrifugation) or other rapid separation methods known in the art. If centrifugation is employed, it is contemplated that the centrifugal force could be any speed that results in viable bacteria after centrifugation. In general, operating parameters may include a spin speed of 1,000-10,000 RPM depending on disc, rotor, or plate size with a centrifugal force of approximately 300-6,000×g, and a spin time of between about 1-60 minutes that varies greatly between centrifuges.

f. Cell Preservation and Formulations

Bacterial formulations used to reduce the incidence of pathogenic microorganisms can be applied to animal waste, food products, food processing areas, food preparation tools, agricultural products, agricultural water (irrigation water, agricultural soils, agricultural crops and the like. The formulations of bacteria described herein can be applied in a powder, liquid, foam, gelled, aerosol or solid form. In liquid formulations, the bacterial formulations may be dispensed from conventional dispensing devices, including pump sprayers, aerosol containers, squirt bottles etc. For application over larger areas, hoses, sprinkler systems or other suitable devices may be used. In the alternative, the formulations can be applied as a dry powder such as lyophilized bacteria or using any of the techniques currently known to a person of skill in the art of waste treatment. The optimal frequency of applications of the bacterial formulations of the present disclosure may depend on the target on which the formulation is to be applied. In certain embodiments of the present disclosure wherein formulations are contemplated, a microorganism is harvested and concentrated using a method that does not markedly decrease the viable cell concentration through centrifugation or filtration. The concentration process may result in viable cell concentrations from $1 \times 10^8$ to $5 \times 10^{12}$ colony forming units per gram (cfu/g) of bacteria or cfu/ml in a growth medium. In more particular embodiments, the concentrations range from $5 \times 10^{10}$ cfu/g to $5 \times 10^{12}$ cfu/g of bacteria or cfu/ml in a growth medium.

In embodiments of the present disclosure wherein formulations are contemplated for preservation, such preservation may include a process of freezing, freeze-drying and/or spray-drying. The preserved bacteria contain a viable cell concentration of $1 \times 10^8$ to $5 \times 10^{12}$ cfu/g. In more particular embodiments, the concentrations range from $5 \times 10^{10}$ cfu/g to $5 \times 10^{13}$ cfu/g of bacteria.

In certain embodiments, the preserved cells can be used in a microbial-based product. The preserved cells can be administered "as-is" without further dilution or modification. Additionally, in certain embodiments, the cells can be mixed with a carrier to dilute the concentration of cells to an appropriate concentration for administration. The carrier can be as simple as one element, or a more complex molecule or mixture of molecules in any proportion in order to act as a suitable carrier. This carrier and composition may, in certain instances, have defined properties such as solubility in water or other mediums. The diluting carrier can be of any composition or combination including but not limited to: lactose, glucose, non-fat dry milk powder, oligosaccharides, glycerol, oil, lecithin, brewer's grains, nut shells, dried plant protein, rice hulls or other materials.

In particular formulations, other chemicals or materials may be used to reduce or absorb moisture and/or oxygen for further protection and preservation of the viable cells. Such chemicals or materials include, but are not limited to: calcium stearate, sodium aluminosilicate, sodium sulfide, sodium carbonate, silica, iron oxides, calcium carbonate, zeolite, bicarbonates, sodium sulfate, silicon dioxide and other silica materials.

g. Preservation Matrices

In certain instances, a bacterial formulation for administration to a subject or a surface or other target can include a preservation matrix, which contains and preserves the bacterial culture. Such a matrix may include a biologically active binding agent, an antioxidant, a polyol, a carbohydrate and a proteinaceous material. For example, the matrix may have a pH of from about 5.0 to about 7.0. Such a preservation matrix may be capable of maintaining at least about $10^6$ viable cells for a period of at least about 12 months in vitro. In other examples, such a matrix maintains at least about $10^7$ viable cells for a period of at least about 12 months in vitro, and more preferably, at least about $10^8$ viable cells for a period of at least about 12 months in vitro. A preservation matrix may be comprised of ingredients to minimize the damaging effects encountered during the preservation process and to provide functional properties. For example when a *Lactobacillus* strain of the present disclosure is added to a preservation matrix for preservation, it is may converted from an actively growing metabolic state to a metabolically inactive state. In formulations of the present disclosure wherein a preservation matrix is contemplated, a biologically acceptable binding agent can be used to both affix the bacterial culture or cultures to an inert carrier during a preservative process and to provide protective effects (i.e., maintains cell viability) throughout preservation and storage of the microbial cells. Preferred biologically acceptable binding agents for use in a preservation matrix include, but are not limited to a water-soluble gum, carboxymethyl cellulose and/or gelatin. A biologically acceptable binding agent typically comprises from about 10% to about 20% by weight of the preservation matrix, and preferably comprises about 14% by weight of the preservation matrix. In one embodiment, a preservation matrix of the present disclosure comprises about 14% gelatin by weight of the preservation matrix.

Antioxidants included in a preservation matrix may be provided to retard oxidative damage to the microbial cells during the preservation and storage process. A particularly preferred antioxidant is sodium ascorbate. An antioxidant typically comprises from about 0.1% to about 1.0% by weight of the preservation matrix, and preferably comprises about 0.5% by weight of the preservation matrix. In one embodiment, a preservation matrix of the present disclosure comprises about 0.5% sodium ascorbate by weight of the preservation matrix.

Polyols (i.e., polyhydric alcohols) included in a preservation matrix may be provided to maintain the native, uncollapsed state of cellular proteins and membranes during the preservation and storage process. In particular, polyols interact with the cell membrane and provide support during the dehydration portion of the preservation process. Preferred polyols include, but are not limited to xylitol, adonitol, glycerol, dulcitol, inositol, mannitol, sorbitol and/or arabitol. A polyol typically comprises from about 1% to about 25% by weight of the preservation matrix, and preferably comprises about 6% by weight of the preservation matrix. In one embodiment, a preservation matrix of the present disclosure comprises about 6% xylitol by weight of the preservation matrix.

Carbohydrates included in a preservation matrix may be provided to maintain the native, uncollapsed state of cellular proteins and membranes during the preservation and storage process. In particular, carbohydrates provide cell wall integrity during the dehydration portion of the preservation process. Preferred carbohydrates include, but are not limited to dextrose, lactose, maltose, sucrose, fructose and/or any other monosaccharide, disaccharide or polysaccharide. A carbohydrate typically comprises from about 0.5% to about 5% by weight of the preservation matrix, and preferably comprises about 2.5% by weight of the preservation matrix. In one embodiment, a preservation matrix of the present disclosure comprises about 2.5% dextrose by weight of the preservation matrix.

A proteinaceous material included in a preservation matrix may provide further protection of the microbial cell during the dehydration portion of the preservation process. Preferred proteinaceous materials include, but are not limited to skim milk and albumin. A proteinaceous material typically comprises from about 0.5% to about 5% by weight of the preservation matrix, and preferably comprises about 1.5% by weight of the preservation matrix. In one embodiment, a preservation matrix of the present disclosure comprises about 1.5% skim milk by weight of the preservation matrix.

One example of a method of preserving microbial cells within a preservation matrix includes coating the cell matrix suspension onto an inert carrier that preferably is a maltodextrin bead. The coated beads can then be dried, preferably by a fluid bed drying method. Fluid bed drying methods are well known in the art. For example, maltodextrin beads may be placed into a fluid bed dryer and dried at 33° C. The air pressure may be set to 1 bar, the cell suspension matrix can then be sprayed onto the beads and the heat is increased to 38° C. The coated beads are then allowed to dry for an additional period of time. The coated maltodextrin beads can be stored as a powder, placed into gelatin capsules, or pressed into tablets.

In other formulations of the present disclosure, the single strains or combinations of strains of bacteria contemplated to be cultured can be formulated as a hard gelatin capsule. Gelatin capsules are commercially available and are well known in the art. In this embodiment, the above preservation method further comprises dispensing the cell suspension matrix to a gelatin capsule, chilling the gelatin capsule until the cell suspension matrix forms a non-fluid matrix and to affix the gel to the interior wall of the gelatin capsule, and desiccating the gelatin capsule in a desiccation chamber. The step of dispensing can be accomplished by any means known in the art, and includes manual, semi-automated and automated mechanisms. The chilling step is performed at from about 4° C. to about 6° C. The step of desiccating the gelatin capsule can include the steps of (i) providing dry air to the desiccation chamber containing less than about 25% moisture, at a temperature from about 24° C. to about 32° C.; and (ii) removing humidified air from the desiccation chamber.

In this formulation of the present disclosure the desiccation process may proceed for about 1 to about 6 hours. The desiccation chamber can include a compressor, at least one hydrocarbon scrubbing filter and a chilled air compressor with or without a desiccant silica gel (or any other suitable desiccant material) column, in series. The air entering the chamber (dry air) preferably contains less than about 25% moisture, and more preferably less than about 15% moisture, and even more preferably less than about 5% moisture, down to as little as zero moisture. The dry air should preferably have a temperature from about 24° C. to about 32° C. This method allows preservation of microbial cells in a controlled environment with room temperature air in a short period of time. Further examples of embodiments of preservation matrices and gelatin capsule formulations may be found in U.S. Pat. No. 6,468,526 which is herein incorporated by reference in its entirety.

h. Microencapsulation

In certain applications, the bacteria cultured with the methods described herein may be placed in a microencapsulation formulation. Such microencapsulation formulations may have applicability for example in administration to subjects via oral, nasal, rectal, vaginal or urethral routes. Spray drying is the most commonly used microencapsulation method in the food industry, is economical and flexible, and produces a good quality product. The process involves the dispersion of the core material into a polymer solution, forming an emulsion or dispersion, followed by homogenisation of the liquid, then atomisation of the mixture into the drying chamber. This leads to evaporation of the solvent (water) and hence the formation of matrix type microcapsules.

For example O'Riordan et al., 2001 reported microencapsulation and spray drying of *Bifidobacterium* cells with a spray inlet temperature of 100° C. and low outlet temperature of 45° C. The cells were reported to be encapsulated satisfactorily to produce micro spheres with gelatinized modified starch as a coating material (O'Riordan et al., 2001). In this study, spray drying was found to be a valuable process for encapsulating *Bifidobacteria*. The process of spray drying is economical, easily scaled up and uses equipment readily available in the food industry (Gibbs et al., 1999). A previous report indicated that survival of probiotic bacteria during spray drying decreased with increasing inlet temperatures (Mauriello et al., 1999).

In one such example of microencapsulation, lyophilized bacteria are suspended in 10 ml of 5% glucose saline solution in a volume so as to obtain a heavy suspension of bacteria which contains approximately $10^9$ organisms per ml, at 0° C. to 4° C. The suspension of bacteria may then be rapidly, but gently, stirred while 0.2-0.4 ml of sodium alginate solution (1.5% weight by volume) is added. The above mixture may then be transferred into a sterile container by using a nitrogen stream through a 14 gauge sheathed needle. The mixture may then be forced through a 30 gauge multi-beveled needle under pressure using a large syringe and nitrogen stream. Very small droplets are generated at the end of the needle, which are then dried by the nitrogen and air stream around the 30 gauge needle, and the droplets are collected in an aqueous solution of 1.3-2% calcium chloride where they gel. Thereafter, they are washed at least three times with 0.08-0.13% 2-(N-cyclohexyl-amino) ethanesulfonic acid (CHES) solution and 1.0-1.5% calcium chloride solution. The gelled droplets or little spheres are further washed with at least a five-fold excess of the 0.1% CHES 1.1% calcium chloride, and normal saline solution. The resultant spheres are then "snap frozen" in liquid nitrogen and then lyophilized. After these steps, the encapsulated organisms can be used in the formulations of the present disclosure. Other examples of microencapsulation can be found for example in U.S. Pat. No. 5,641,209 that is herein incorporated by reference.

i. Freezing

An embodiment of preserving by freezing is to prepare frozen beads or pellets comprising the microorganism. After a suitable fermentation, the liquid is removed from the viable bacteria by a method including but not limited to centrifugation, ultrafiltration, or sedimentation. An additive compound may be added to the bacteria prior to freezing. Suitable additives include but are not limited to, lactose, sucrose, trehalose, maltodextrin, cyclodextrin, spray gum, fish gelatin bloom, and maltitol. In one embodiment, the frozen culture may comprise 0.5% to 13% of an additive compound measured as w/w of the frozen material. These additives may function to increase the melting temperature of the frozen culture above the desired storage temperature. U.S. Publ. Appl. 20070254353. An example of a suitable storage temperature is –46° C.

Suitable additives may also serve as cryoprotective agents to improve the stability of the frozen culture. Cryoprotective agents include, but are not limited to, proteins, protein hydrolysates, carbohydrates, or a compound involved in the biosynthesis of nucleic acids. U.S. Publ. Appl. 20070254353. Proteins or protein hydrolysates include but are not limited to, malt extract, milk powder, whey powder, yeast extract, gluten, collagen, gelatin, elastin, keratin, or albumin. Carbohydrates include but are not limited to pentoses (eg. ribose, xylose), hexoses (e.g. fructose, mannose, sorbose), disaccharides (e.g. sucrose, trehalose, melibiose, lactulose), oligosaccharides (e.g. raffinose), oligofrutoses (e.g. actilight, fribroloses), polysaccharides (e.g. maltodextrins, xanthan gum, pectin, alginate, microcrystalline cellulose, dextran, PEG), and sugar alcohols (sorbitol, manitol). U.S. Publ. Appl. 20070254353.

Preferably, the frozen pellet or bead has a content of viable bacteria of at least $5\times10^9$ colony forming units (CFU) per gram of frozen material. The additive may be mixed with the bacteria after fermentation and frozen by adding the mixture dropwise into liquid $N_2$ forming frozen pellets or granula of the mixture. U.S. Publ. Appl. 20070254353. The material may then be packaged.

j. Foam Formulations

A foam is defined herein as is a composition that is formed by trapping many gas bubbles in a liquid. Methods pertaining to the formulation and administration of foams are set forth in U.S. Pat. No. 4,112,942, U.S. Pat. No. 5,652,194, U.S. Pat. No. 6,140,355, U.S. Pat. No. 6,258,374, and U.S. Pat. No. 6,558,043, each of which is herein specifically incorporated by reference in its entirety.

A typical foam pharmaceutical formulation may, for example, be constructed by introducing a gas into a gel or aqueous pharmaceutical composition such that bubbles of the gas are within the pharmaceutical composition.

One example of preparation of a foam formulation involving the use of a pressurized gas is discussed as follows. In brief, cultured bacteria of the present disclosure (12% w/v) may be mixed with mineral oil by stirring for approximately 30 minutes under a light vacuum to generate a first mixture. A solution of cetyl stearyl alcohol (6% w/v) in mineral oil may be added to the first mixture under the same conditions, to form a final mixture. The final mixture may be subsequently stirred for an additional 10 minutes. The final mixture may then be placed into an appropriate canister and pressurized with a propellant gas. The canister may have a mechanism for dispensing the final mixture, such as, for example a polyethylene valve of the type commonly found in pressurized canisters. This method is only exemplary.

k. Electrostatic Spray

A bacterial formulation of the present disclosure can be applied a surface, such as an animal waste surface, a food processing surface, an agricultural surface etc. using an electrostatic spray apparatus. This apparatus should have a chamber for containing the bacterial formulation and an opening in fluid connection with the chamber through which the bacterial formulation can be dispensed and deposited on a desired surface. The apparatus should allow for electrically charging the bacterial formulation. For example, a conductor can be used to connect the chamber to a voltage power source. One of skill in the art would be aware of other suitable devices that can function as such a conductor.

To apply the bacterial formulation to a surface, the formulation is placed into the chamber of the electrostatic spray apparatus. The bacterial formulation can be pumped into the chamber. When the bacterial formulation is placed into the chamber, it contacts the conductor, such as a high-voltage DC electrode, and becomes charged. Once the bacterial formulation in the chamber is charged, it carries the same charge as the conductor. As a result the formulation and conductor repel each other. This repulsive force discharges the bacterial formulation through the opening of the nozzle to create streams of droplets. Therefore, in the method of the present disclosure, no additional gas source is required for atomization of the coating formulation. Accordingly, a cloud of highly charged, highly uniform-sized droplets can be formed.

Since the droplets that are formed carry a charge, when they are deposited on a grounded surface, they will be guided by their electrostatic attraction to the grounded and hence electrically neutral surface. Since the droplets carry the same electrical charge, they will repel each other. This repulsion causes the droplets arriving at the surface to avoid the areas where other droplets have already been deposited and instead land on areas of the surface that have not been coated. In this way, an inherently uniform coating is formed.

One example of a suitable nozzle apparatus that can be used in the method of the disclosure is an apparatus for electrohydrodynamic spray-coating that is disclosed in U.S. Pat. No. 4,749,125. This apparatus has a metal shim that is placed within the nozzle apparatus to define a plurality of nozzle openings. The metal shim is also connected to a voltage source that allows for the formation of electrically charged droplets of coating formulation.

l. Lyophilization

Dry microorganism cultures may be prepared according to the disclosure, in addition to any constituents present from a fermentation medium, such as metabolic products, the medium may comprise at least one matrix material with or without other stabilizing substances. These materials are preferably selected from inorganic salts or buffers, at least one other compound which is selected from mono-, oligo- and polysaccharides, polyols, polyethers, amino acids, oligo- and polypeptides, milk-derived compounds, organic carboxylic acids, mineral compounds, organic carrier materials such as wheat semolina bran, alginates, DMSO, PVP (polyvinylpyrrolidone), CMC (carboxymethylcellulose), alpha-tocopherol, beta.-carotene and mixtures thereof.

Examples of suitable saccharide carrier components are sucrose, fructose, maltose, dextrose, lactose and maltodextrin. An example of a suitable polyol is glycerol. Examples of suitable amino acids are glutamic acid, aspartic acid and the salts thereof. An example of a suitable peptide carrier is peptone. An example of a milk-derived compound is, in addition to the abovementioned maltodextrin, also sweet whey powder. Suitable organic carboxylic acids are, for example, citric acid, malic acid and L-ascorbic acid. Examples of suitable mineral carriers are montmorillonite and palygorskite.

In certain aspects of the disclosure mixtures of the abovementioned classes of substances may be employed. Mixtures of this type preferably comprise, as main component, a matrix material, such as one of the abovementioned saccharide components or, for example, sweet whey powder, with or without a minor content of at least one further component, such as a buffer component (for example citric acid) or an antioxidant (for example L-ascorbic acid or α.-tocopherol). The addition of further stabilizing constituents, such as sodium glutamate and/or peptone, has likewise proved to be advantageous.

The matrix component is customarily used in carrier compositions usable according to the disclosure in about 5 to 30 times the amount of the other carrier constituents. Examples of particularly suitable carrier combinations are: a) sweet whey powder/citric acid/L-ascorbic acid (weight ratio about 40:1:1). b) maltodextrin/lactose/citric acid/L-ascorbic acid (weight ratio about 20:20:1:1), unsupplemented or supplemented by about 1.5 parts of .beta.-carotene and 0.5 part of .alpha.-tocopherol per part of citric acid. c) maltodextrin/sodium glutamate/L-ascorbic acid (weight ratio about 10:1.5:1). d) lactose/glucose/peptone/citric acid (weight ratio about 6:6:1.2:1).

The carrier substances according to the disclosure can be added to the microorganism suspension either as solid or in dissolved form. However, preferably, a sterile solution of the carrier/carriers is prepared, this is cooled to a temperature of from 4 to 10° C. and this is mixed with the likewise cooled microorganism suspension with gentle stirring. To prepare a homogeneous suspension, the resultant mixture is stirred with further cooling for a period of from about 10 minutes to 1 hour.

The microorganism suspension containing the carrier added in the manner described above can then be dried in various ways. Suitable drying processes are in principle freeze drying, fluidized-bed drying and, preferably, spray-drying. For the purposes of the present disclosure, spray-drying also comprises modified spray-drying processes, such as spray-agglomeration or agglomerating spray-drying. The latter process is also known under the name FSD (fluidized spray-dryer) process.

Freeze-drying for preparing dry microorganism cultures according to the disclosure can be carried out, for example, on the basis of the freeze-drying process described in U.S. Pat. No. 3,897,307. The contents of these publications are hereby incorporated completely by reference.

Another, drying process contemplated for use in the present disclosure is spray-drying. Those methods which can be used according to the disclosure are essentially all spray-drying techniques known in the art. The material to be sprayed can, for example, be dried concurrently or counter-currently; spraying can be carried out by means of a single-component or multiple-component nozzle or by means of an atomizer wheel.

Preference is given according to the disclosure to the use of material to be sprayed having a solids content (after addition of the carrier) of from about 10 to 40, such as from about 10 to 25% by weight.

One particular factor according to the disclosure is the use of preconditioned, i.e. low-moisture, drying air. Preferably, use is made of compressed air having a dew point at about −25° C.

The drying process according to the disclosure may be carried out in such a manner that a very low residual moisture content is present in the dry material. The percentage water content is preferably from about 2 to 3% by weight. This may be achieved by adding a post-drying step subsequently to the spray-drying step. The drying material for this purpose is, for example, post-dried in a fluidized bed, preferably at a temperature in the range of from 15 to 50.degree. C., for a period of, for example, from 15 minutes to 20 hours. Again, preferably, conditioned compressed air or conditioned nitrogen serves as drying gas. However, the post-drying can also be performed by applying a vacuum of from about 1 to 50 mm Hg for a period of from about 15 minutes to 20 hours and at a temperature of from about 15 to 50° C. In this case, preference is given to stirring the drying material, for example, using a paddle agitator.

Instead of the above-described physical post-drying processes, it is also conceivable to add specific desiccants to the dry material obtained from the spray-drying. Examples of suitable desiccants are inorganic salts, such as calcium chloride and sodium carbonate, organic polymers, such as the product obtainable under the trade name Kollidion 90 F, and silicon-dioxide-containing desiccants, such as silica gel, zeolites and desiccants which are obtainable under the trade name Tixosil 38, Sipernat 22 S or Aerosil 200.

The content of viable microorganisms is in the range of from about $5 \times 10^8$ to $1 \times 10^{12}$ cfu/g of dry matter. These preparations are also called according to the disclosure powder concentrates. Since, for individual final applications, lower contents of viable microorganisms are also completely sufficient, powder concentrates of this type can therefore if appropriate be blended to the final count of viable microorganisms by mixing with further inert carrier material.

m. Refrigeration

In certain embodiments, probiotic microorganisms may be refrigerated after harvesting and concentrating. In certain embodiments, after a suitable fermentation, the liquid is removed from the viable bacteria by a method including but not limited to centrifugation, ultrafiltration, or sedimentation. An additive compound may be added to the bacteria prior to refrigeration. Suitable additives include but are not limited to, lactose, sucrose, trehalose, maltodextrin, cyclodextrin, spray gum, fish gelatin bloom, and maltitol. In one embodiment, the refrigerated culture may comprise 0.5% to 13% of an additive compound measured as w/w of the refrigerated material. In certain other embodiments, after a suitable fermentation, only a portion of the fermentation medium is removed from the viable bacteria prior to refrigeration by a method including but not limited to centrifugation, ultrafiltration, or sedimentation. Exemplary temperatures for refrigeration may be in the range from about 1° C. to about 10° C., although in certain embodiments it is contemplated that the refrigeration temperature may be below this range if additives are introduced which would lower the freezing point of the liquid containing the probiotic microorganisms.

Suitable additives may also serve as cryoprotective agents to improve the stability of the refrigerated culture. Cryoprotective agents include, but are not limited to, proteins, protein hydrosolates, carbohydrates, or a compound involved in the biosynthesis of nucleic acids. U.S. Publ. Appl. 20070254353. Proteins or protein hydrolysates include but are not limited to, malt extract, milk powder, whey powder, yeast extract, gluten, collagen, gelatin, elastin, keratin, or albumin. Carbohydrates include but are not limited to pentoses (eg. ribose, xylose), hexoses (e.g. fructose, mannose, sorbose), disaccharides (e.g. sucrose, trehalose, melibiose, lactulose), oligosaccharides (e.g. raffinose), oligofrutoses (e.g. actilight, fribroloses), polysaccharides (e.g. maltodextrins, xanthan gum, pectin, alginate, microcrystalline cellulose, dextran, PEG), and sugar alcohols (sorbitol, manitol). U.S. Publ. Appl. 20070254353.

m. Uses of Formulated Bacterial Products

Formulated Bacterial Products for Consumption

The microbial product, whether diluted or not, can be packaged in a form that is appropriate or convenient for shipment, administration, or storage. For example, the product can be placed into a hermetically sealed pouch of plastic, paper, metalized plastic, or metal (e.g. aluminum), bottle, capsule, plastic bag, or a box. The final viable cell concentrations can vary dramatically in the product. The viable cell concentration can range from $1 \times 10^4$ to $1 \times 10^{13}$ cfu/g of final product, depending upon an appropriate package and effective dose for application.

In certain embodiments of the disclosure, the microbial based product can be formulated as a food or beverage product. Specific food and beverage forms of the composition of the disclosure include, but are not limited to: fermented milks, lactic acid bacteria beverages, fermented vegetable beverages, fermented fruit beverages and fermented soymilk beverages. "Fermented milk" can refer to a pasty or liquid preparation prepared by fermenting milk or a dairy product with lactic acid bacteria or yeasts. Therefore, "fermented milk" can include not only products in beverage form but also products in yogurt form. "Lactic acid bacteria beverage" refers to a beverage prepared by using as a main material a paste or liquid preparation prepared by fermenting milk or a dairy product with lactic acid bacteria or yeasts and diluting it with water.

In certain embodiments of the disclosure, the microbial based product can be formulated to include cell-containing microencapsulated forms, solid food forms (e.g., granules, powders (including freeze-dried powders of fermented milk, etc.), tablets, effervescent tablets, gums, and puddings), and milk products other than the above-mentioned fermented milk and lactic acid bacteria beverages.

In embodiments of the disclosure wherein a microbial based product is formulated as a food, beverage, or pharmaceutical, processing into food or beverage forms and pharmaceutical forms can be carried out in a conventional manner. Carriers for use in the processing into such forms may be any edible carriers, pharmaceutically acceptable excipients and diluents.

The amount of lactic acid bacteria to be incorporated in the composition of the disclosure can be suitably selected so as to achieve a concentration of about $10^7$ to $10^{11}$ cells/100 g composition, for example. Since the composition of the disclosure is designed to contain lactic acid bacteria, conditions such as the application of heat and pressure may not be suitable in the processing of the composition into end products. Therefore, for example, in processing the composition of the disclosure into solid food forms, it is preferable to directly formulate the lactic acid bacteria in the form of lyophilized cells or treat the lyophilized cells with a suitable coating agent and use the coated cells.

In embodiments of the disclosure wherein food or beverage formulations are concerned, representative food and beverage forms include fermented milks, lactic acid bacteria beverages, fermented vegetable beverages, fermented fruit beverages, fermented soymilk beverages, etc. Fermented vegetable beverages, fermented fruit beverages and fermented soymilk beverages are described in detail below. Processing into such a form can be carried out by a procedure comprising culturing lactic acid bacteria in a suitable fermentation material containing nutrients for lactic acid bacteria, such as fluids derived from vegetables or fruits, soymilk (soybean emulsion), etc. to thereby cause fermentation of the material. Vegetables and fruits for use as the fermentation material include cuttings, crushings, grindings, squeezed juices, enzyme-treated products, and dilutions or concentrates thereof. Usable vegetables include, for example, pumpkins, carrots, tomatoes, sweet peppers, celery, spinach, colored sweet potatoes, corn, beats, kale, parsley, cabbages, and broccoli. Usable fruits include, for example, apples, peaches, bananas, strawberries, grapes, water melons, oranges, and mandarins.

Cuttings, crushings, and grindings of vegetables and fruits can be obtained by, for example, a procedure which comprises washing at least one of vegetables and fruits, and where necessary, subjecting it to a blanching treatment, e.g. placing in hot water, and cutting, pulverizing or milling it by means of a crusher, mixer, food processor, pulverizer or the like. Squeezed juices can be prepared by using a filter press, juicer-mixer, or the like. Squeezed juices can also be prepared by filtering millings through a filter cloth or the like. Enzyme-treated products can be prepared by permitting cellulase, pectinase, protopectinase or the like to act upon cuttings, crushings, grindings, or squeezed juices. Dilutions include 1- to 50-fold aqueous dilutions. Concentrates include those concentrated 1- to 100-fold by such means as freeze concentration, concentration under reduced pressure, etc.

Soymilk, which is another specific example of the fermentation material, can be prepared from soybean materials in the conventional manner. Examples of such soymilks include homogenates prepared by immersing skinned soybeans in water, wet-pulverizing the soybeans with a suitable mill such as a colloid mill and homogenizing the pulverizate in the conventional manner, and solutions of water-soluble soy protein in water.

The lactic acid fermentation product thus obtained may be in a curd form (a yogurt-like or pudding-like form) and such a product can be directly ingested as a solid food. Such a lactic acid fermentation product in a curd form can be further homogenized to prepare a desired beverage form. In carrying out homogenization, it is also possible, where necessary, to make appropriate dilutions, add organic acids for pH adjustment, and/or add in suitable amounts various other additives as are typically employed in the manufacture of beverages, such as saccharides, fruit juices, thickeners, surfactants, and flavorings. Preferable additives and their amounts (% by weight based on the weight of the curd-form fermentation product) are, for example, glucose 8% (% by weight, the same applies hereinafter), sucrose 8%, dextrin 8%, citric acid 0.1%, glycerol fatty acid esters 0.2%, and flavorings 0.1%.

Another specific example of the composition of the disclosure in food form is the composition in the form of an effervescent product. This product can be prepared by formulating 10 to 35% (% by weight; the same applies below) of sodium carbonate and/or sodium hydrogencarbonate and 20 to 70% of a neutralizer, as effervescent ingredients, with 0.01 to 50% of lactic acid bacteria (lyophilized cells) of the disclosure. The neutralizer used is an acidic compound capable of neutralizing the sodium carbonate and/or sodium hydrogencarbonate to generate carbon dioxide gas. Representative examples of such compounds are organic acids such as L-tartaric acid, citric acid, fumaric acid and ascorbic acid.

The amount of effervescent ingredients in the effervescent product of the disclosure is such that when this product of the disclosure is dissolved in water, the solution is acidic, particularly an acidity of about pH 3.5-4.6. More particularly, the amount can be selected from the range of 10-35% sodium carbonate and/or sodium hydrogencarbonate and 20-70% neutralizer. In particular, the amount of sodium carbonate may be selected from the range of 11-31%, and preferably 22-26%; and/or sodium hydrogencarbonate from the range of 10-35%, and preferably 20-30%. It is most preferable to use sodium hydrogencarbonate alone, within the range of 20-25%. The amount of the neutralizer is selected from the range of 20-70%, and preferably 30-40%. In particular, it is most preferable to use L-tartaric acid within the range of 20-25% and ascorbic acid within the range of 8-15%.

The effervescent product of the disclosure can contain lactic acid bacteria of the disclosure and effervescent ingredients as essential components and may optionally be supplemented with suitable amounts of various known additives such as excipients, binders, disintegrators, lubricants, thickeners, surfactants, osmoregulators, electrolytes, sweeteners, flavorings, colors, pH regulators, and so forth. Examples of such additives include starches such as wheat starch, potato starch, corn starch, dextrin, etc.; sugars such as sucrose, glucose, fructose, maltose, xylose, lactose, etc.; sugar alcohols such as sorbitol, mannitol, maltitol, xylitol, etc.; glycosides such as coupling sugar, palatinose, etc.; excipients such as calcium phosphate, calcium sulfate, etc.; binders and thickeners such as starches, sugars, gelatin, gum Arabic, dextrin, methylcellulose, poly-vinylpyrrolidone, polyvinyl alcohol, hydroxypropylcellulose, gum xanthan, pectin, gum tragacanth, casein, alginic acid, etc.; lubricants such as leucine, isoleucine, L-valine, sugar esters, hydrogenated oils, stearic acid, magnesium stearate, talc, macrogols, etc.; disintegrators such as crystalline cellulose, carboxymethylcellulose (CMC), carboxymethylcellulose sodium (CMC-Na), carboxymethylcellulose calcium (CMC-Ca), etc.; surfactants such as polyoxyethylene sorbitan fatty acid ester (polysorbate), lecithin, etc.; dipeptides such as aspartame, alitame, etc.; and sweeteners such as stevia, saccharin, etc. Such additives can be suitably selected and used in suitable amounts taking into consideration the relationship of each to the essential components, the nature of the preparation, and the method of production of the preparation among other factors.

In addition, vitamins, particularly cyanocobalamine and ascorbic acid (vitamin C), can be added in suitable amounts to the effervescent product of the disclosure. The amount is not particularly limited, but vitamin C, for instance, is usually added up to 30% at most, and preferably within the range of about 5 to about 25%.

The method of producing the effervescent product of the disclosure may be fundamentally similar to conventional methods for the production of effervescent tablets of this kind. Thus, the product of the disclosure in effervescent tablet form can be prepared by weighing out predetermined amounts of the respective ingredients, mixing them, and processing the whole by, for example, the direct powder compression method or wet or dry granulation-compression method.

The thus obtained product of the disclosure can be converted to a beverage form suitable for oral administration by simply being placed in water and be administered orally.

The composition of the disclosure can be formed into general pharmaceutical products using suitable pharmaceutically acceptable carriers together with, as an essential component, the lactic acid bacteria of the disclosure and put into practical use. Examples of usable pharmaceutically acceptable carriers include various diluents and excipients such as fillers, extenders, binders, humectants, disintegrators, surfactants, lubricants, etc. which are known in the art. Such carriers can be selectively used according to the unit dosage form of the pharmaceutical preparation to be created.

The unit dosage form of the pharmaceutical product can be selected from a variety of dosage forms. Representative forms are tablets, pills, powders, solutions, suspensions, emulsions, granules and capsules.

Tablets can be prepared using as pharmaceutical carriers, for example, excipients such as lactose, sucrose, sodium chloride, glucose, urea, starch, calcium carbonate, kaolin, crystalline cellulose, silicic acid, potassium phosphate, etc.; binders such as water, ethanol, propanol, simple syrup, glucose solutions, starch solutions, gelatin solutions, carboxymethylcellulose, hydroxypropylcellulose, methylcellulose, polyvinylpyrrolidone, etc.; disintegrators such as carboxymethylcellulose sodium, carboxymethylcellulose calcium, low-substituted hydroxypropylcellulose, dry starch, sodium alginate, agar powder, laminaran powder, sodium hydrogen-carbonate, calcium carbonate, etc.; surfactants such as polyoxyethylene sorbitan fatty acid esters, sodium lauryl sulfate, stearic acid monoglyceride, etc.; disintegration inhibitors such as sucrose, stearin, cacao butter, hydrogenated oils, etc.; absorption promoters such as quaternary ammonium salts, sodium lauryl sulfate, etc.; humectants such as glycerol, starch, etc.; adsorbents such as starch, lactose, kaolin, bentonite, colloidal silica, etc.; and lubricants such as purified talc, stearates, boric acid powder, polyethylene glycol, etc.

Furthermore, if necessary, the tablets may be coated with a standard coating material to provide sugar-coated tablets, gelatin-coated tablets, enteric-coated tablets, film-coated tablets, etc., or processed into multi-layered tablets such as double-layered tablets.

Pills can be prepared using as pharmaceutical carriers, for example, excipients such as glucose, lactose, starch, cacao butter, hydrogenated vegetable oils, kaolin, talc, etc.; binders such as gum Arabic powder, gum tragacanth powder, gelatin, ethanol, etc.; and disintegrators such as laminaran, agar, etc.

Furthermore, where necessary, coloring agents, preservatives, aroma chemicals, flavorings, sweeteners, and other medicinal substances can also be incorporated in the pharmaceutical product of the disclosure.

The amount of lactic acid bacteria of the disclosure to be incorporated in the pharmaceutical product of the disclosure is not particularly limited and can be suitably selected from a broad range. The generally recommended proportion is about $10^7$-$10^{12}$ cells/unit dosage form of the pharmaceutical product.

The method of administering the pharmaceutical product is not particularly limited and can be suitably decided according the pharmaceutical product's form, patient's age, sex and other variables, severity of illness, etc. For example, tablets, pills, solutions, suspensions, emulsions, granules, and capsules are administered orally.

The composition of the disclosure is so adapted that, on intake (administration), the lactic acid bacteria of the composition settle in the lower digestive tract as part of the intestinal microflora, whereby the expected effects of lactic acid bacteria such as intestinal regulation and intestinal microflora improvement can be achieved. Accordingly, a particularly preferable pharmaceutical product form is enteric-coated tablets, by which the lactic acid bacteria can be transported to the intestine without being attacked by gastric acid.

The present disclosure can be adjusted to provide beneficial effects to many types of animals, including ruminal fermentors, cecal fermentor and intestinal fermentors. In one preferred embodiment, the product is fed to ruminal fermentors to reduce scours events, improve animal health and animal productivity. Ruminal fermentors that might benefit from the present disclosure include but are not limited to: cattle, sheep, goats, camels, llama, bison, buffalo, deer, wildebeest, antelope, and any other pre-gastric fermentor. In another embodiment, the product is fed to cecal fermentors to reduce scours events, improve animal health and animal productivity. Cecal fermentors that might benefit from the present disclosure include but are not limited to: horses, ponies, elephants, rabbits, hamsters, rats, hyraxes, guinea pigs, and any other post-gastric fermentor that using the cecum as the primary location of fermentative digestion. In another embodiment, product is fed to intestinal fermentors to reduce scours events, improve animal health and animal productivity. Intestinal fermentors that might benefit from said disclosure include but are not limited to: humans, pigs, chickens, and other post-gastric fermentor using the large intestine as the primary location of fermentative digestion.

The present disclosure may provide direct fed microbial products which are derived from probiotic microorganisms that have The amount of microorganism administered to the animal feed can be any amount sufficient to achieve the desired increase in animal efficiency and/or animal health. This amount can be anywhere from 1 to $10^{13}$ organisms per kg of animal feed. For example, amounts of about $10^4$ cfu/gram feed, about $5 \times 10^4$ cfu/gram feed, about $10^5$ cfu/gram feed, about $5 \times 10^5$ cfu/gram feed, or ranges between 1 to $10^{13}$ organisms per kg of animal feed can be used. In some embodiments, the dried biological may be administered to an animal through a variety of means including, but not limited to, being distributed in an aqueous solution and subsequently being applied to animal feed, water source, or directly fed to the animal, or through direct application of the product onto animal feed or direct administration or consumption by the animal.

The animals that may benefit include but are not limited to cattle (beef), pigs, chickens, turkeys, lamb, deer, buffalo, alligator, and snake. The animal can also be a fish or shellfish. Animals raised in aquaculture or caught in the wild include fish and shellfish such as salmon, catfish, trout, tilapia, flounder, haddock, cod, mackerel, tuna, swordfish, shark, squid, clams, scallops, mussels, oysters, abalone, lobster, shrimp, crabs, and crayfish.

Other Applications

In certain embodiments, the formulated bacterial products can be used for the treatment of animal waste effluents. The animal waste may be from animals whose manure is stored in bulk. Common examples include but are not limited to: swine fecal material, chicken fecal material, turkey fecal material, horse fecal material, zoo animal fecal material, cattle fecal material and human fecal material.

In certain embodiments, the formulated bacterial products can be used for the reduction or elimination of pathogens. Examples of pathogens include but are by no means limited to *Escherichia coli, Salmonella* spp., including *Salmonella typhimurium, Salmonella enterica, Salmonella enteritidis, Clostridium botulinum, Staphylococcus aureus, Campylobacter jejuni, Yersinia enterocolitica* and *Yersinia pseudotuberculosis, Listeria monocytogenes, Vibrio cholerae* O1, *Vibrio cholerae* non-O1, *Vibrio parahaemolyticus* and other *Vibrio* spp., *Vibrio vulnificus, Clostridium perfringens, Bacillus cereus, Aeromonas hydrophile, Plesiomonas shigelloides, Shigella* spp., miscellaneous enterics, and *Streptococcus* spp. The disclosure is considered to be useful in preventing the growth of a wide variety of such types of pathogenic organisms.

A wide range of harmful bacterial species can potentially be found in water, on food, on surfaces, and in organic waste material. In particular, contamination of agricultural food products with human pathogenic microorganisms is a cause of major concern not only in developing countries, but also in most developed regions of the world. Specific examples of infectious diseases or conditions of humans which can be caused by pathogenic bacteria include, but are not limited to: staphylococcal infections (caused, for example, by *Staphylococcus aureus, Staphylococcus epidermis*, or *Staphylococcus saprophyticus*), streptococcal infections (caused, for example, by *Streptococcus pyogenes, Streptococcus pneumoniae*, or *Streptococcus agalactiae*), enterococcal infections (caused, for example, by *Enterococcus faecalis*) diphtheria (caused, for example, by *Corynebacterium diptheriae*), anthrax (caused, for example, by *Bacillus anthracis*), listeriosis (caused, for example, by *Listeria monocytogenes*), gangrene (caused, for example, by *Clostridium perfringens*), tetanus (caused, for example, by *Clostridium tetani*), botulism (caused, for example, by *Clostridium botulinum*), toxic enterocolitis (caused, for example, by *Clostridium difficile*), bacterial meningitis (caused, for example, by *Neisseria meningitidis*), bacteremia (caused, for example, by *Neisseria gonorrhoeae*), *E. coli* infections (*colibacilliocis*), including urinary tract infections and intestinal infections, shigellosis (caused, for example, by *Shigella* species), salmonellosis (caused, for example, by *Salmonella* species), *yersinia* infections (caused, for example, by *Yersinia pestis, Yersinia pseudotuberculosis*, or *Yersinia enterocolitica*), cholera (caused, for example, by *Vibrio cholerae*), campylobacteriosis (caused, for example, by *Campylobacter jejuni* or *Campylobacter fetus*), gastritis (caused, for example, by *Helicobacter pylori*), pseudomonas infections (caused, for example, by *Pseudomonas aeruginosa* or *Pseudomonas mallei*), *Haemophilus influenzae* type B (HIB) meningitis, HIB acute epiglottitis, or HIB cellulitis (caused, for example, by *Haemophilus influenzae*), pertussis (caused, for example, by *Bordetella pertussis*), mycoplasma pneumonia (caused, for example, by *Mycoplasma pneumoniae*), nongonococcal urethritis (caused, for example, by *Ureaplasma urealyticum*), legionellosis (caused, for example, by *Legionella pneumophila*), syphillis (caused, for example, by *Treponema pallidum*), leptospirosis (caused, for example, by *Leptospira interrogans*), Lyme borreliosis (caused, for example, by *Borrelia burgdorferi*), tuberculosis (caused, for example, by *Mycobacterium tuberculosis*), leprosy (caused, for example, by *Mycobacterium leprae*), actinomycosis (caused, for example, by *Actinomyces* species), nocardiosis (caused, for example, by *Nocardia* species), chlamydia (caused, for example, by *Chlamydia psittaci, Chlamydia trachomatis*, or *Chlamydia pneumoniae*), Rickettsial diseases, including spotted fever (caused, for example, by *Rickettsia ricketsii*) and Rickettsial pox (caused, for example, by *Rickettsia akari*), typhus (caused, for example, by *Rickettsia prowazekii*), brucellosis (caused, for example, by *Brucella abortus, Brucella melitens*, or *Brucella suis*), and tularemia (caused, for example, by *Francisella tularensis*). Diseases with similar origins and symptoms are also known to affect animals.

In certain other embodiments, the formulated bacterial products can be used in the treatment of agricultural water (irrigation water), agricultural soils and agricultural crops. In still other embodiments, the formulations of cultured bacteria can be applied in the treatment at food processing facilities. In the case of food processing facilities, agricultural waters and soils, the formulations of cultured bacteria can be applied prophylactically or as a sanitizing agent following an exposure.

The product can be used to treat foods including meat and meat products. The meat product can generally be any whole, cut, ground or processed meat product, including, ground beef ("hamburger"), ground turkey, ground chicken, ground pork, beef sausage, pork sausage, chicken sausage, turkey sausage, hot dogs, bologna, salami, cold cuts, game hens, whole chicken, lamb, ham, pork, cube meat, steaks, roasts, fillets, fish, or liver.

Any type of agricultural produce sold in marketplaces, such as those derived from plant or fungi, can be treated by the methods and compositions disclosed herein. Additional types of produce products that can be treated by the disclosed antimicrobial compositions include but are not limited to those derived from leaves, stems, fruit, flowers, seeds, roots, and like components that form the plant, as well as those derived from fungi, including the cap, stem, mycelium and annulus, and like components that form the fungi.

Microbial-based product compositions used to reduce the incidence of pathogenic microorganisms can be applied to agricultural produce as a dry powder (e.g., freeze dried, active bacteria). In addition, the microbial-based product compositions can be sprayed or poured onto the produce in the form of liquid suspensions containing the probiotic bacteria at cell concentrations ranging between $1\text{-}10^{10}$ CFU per ml. As such, the probiotic composition may be dispensed from conventional dispensing devices, including pump sprayers, aerosol containers, squirt bottles, etc. For application over large areas, hoses, sprinkler systems, or other suitable devices may be used to apply the probiotic composition to the target produce. Alternatively, the preparations can be applied as a dry powder or using any other of a variety of techniques known to one of skill in the art of agricultural produce treatment. Finally, any other suitable technique or method may also be used to apply the probiotic composition to the area of concern. The optimal frequency of applications of probiotic compositions and the optimal cell concentration for such compositions depends on the type of agricultural produce, as well as storage methods, whether agitation is employed and the rate of turnover in the storage facility. The specific mode of application of the probiotic composition employed would be predicated on a number of factors that are evaluated on-site.

Any type of agricultural environment, such as soils and field crops, can be treated by the methods and compositions disclosed herein. Additional agricultural environment types that can be treated by the disclosed antimicrobial compositions include but are not limited soil, with including soil used to cultivate plants such as vegetables, roots, beans, mushrooms, fruits, fruit trees, shrubs, herbs, ornamental plants and grasses.

Any type of surface can be treated with the probiotic-containing product. Examples of surfaces that may be treated include of animate surfaces such, as those of animals or plants, and inanimate surface, such as food, buildings, furniture, objects and the like. Specific examples of surfaces that the probiotic composition could be applied to include, but are not limited to the following: meat, grinders, processors, extruders, cutting surfaces, cutting apparatus, blades, seafood, agricultural produce (fruit, vegetables, etc.), nuts, legumes, sprouts, trees, leaves, seeds, bulbs, flowers, animals (livestock and pets), eggs shells, skin, hair, bone, horn, hooves, wool, leather, lawns, fields, soil, floors, walls, countertops, cabinets, toilets, bathtubs, bathrooms (portable and non-portable), sinks, laundry equipment, kitchen appliances (refrigerators, freezers, dishwashers, etc.), heating and refrigeration coils, fans, ceiling fans, heating systems, air conditioning system, ventilation systems, internal and external ducts for ventilation, heating and air conditioning, tabletops, chairs and sofas, desks, luggage, fabrics, clothing, footwear, sports equipment, audio/visual equipment, computers, clocks, boxes (cardboard, wood, etc.), books, paper surfaces, garbage/trash receptacles, building materials, interior and exterior of transportation equipment (automobiles, airplanes, trains, boats, etc.), interior and exterior of spacecraft and other space facilities, trailers, tires, metal, ceramic, tile, linoleum, carpet, wall paper, painted surfaces, plastic, vinyl, polyvinyl chloride (PVC) and the like, plastic, rubber, glass, hose line, plumbing (inside and outside), other application machinery, lighting, heating and cooling filaments, ovens, storage containers, bottles, cans, reception areas, milking parlors, food processing facilities, and the like.

EXAMPLES

The following examples are included to demonstrate preferred embodiments of the disclosure. It should be appreciated by those of skill in the art that the techniques disclosed in the examples which follow represent techniques discovered by the inventors to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit or scope of the disclosure. The following Examples are offered by way of illustration and not by way of limitation.

Example 1

Preparation of Reagents a. Lactobacilli MRS Agar and Broth

Lactobacilli MRS agar and broth are recommended for the use in the isolation of *Lactobacillus* species. Lactobacilli MRS agar and broth are based on the formulations of de Man et al., *J. Appl. Bacteriol.*, 23:130, 1960. Difco™ & BBL™ Manual, 2nd Edition. The agar and broth were demonstrated by de Man et al., to support Lactobacilli growth from oral, fecal dairy and other sources. Lactobacilli MRS Agar and broth contain peptone and dextrose, both of which supply nitrogen, carbon and other elements necessary for growth. Polysorbate 80, acetate, magnesium and manganese provide growth factors for culturing a variety of lactobacilli.

In brief, to generate Lactobacilli MRS Agar, into one liter of distilled water: 10.0 g proteose peptone No. 3, 10.0 g beef extract, 5.0 g yeast extract, 20.0 g dextrose, 1.0 g polysorbate 80, 2.0 g ammonium citrate, 5.0 g sodium acetate, 0.1 g magnesium sulfate, 0.05 g manganese sulfate, 2.0 g dipotassium phosphate and 15.0 g agar. Lactobacilli MRS broth is generated by the same methods without the addition of agar. These materials are readily obtained from Becton Dickinson and Company, Franklin Lakes N.J.

b. Lactobacilli Fermentation Medium

Lactobacilli fermentation medium may be made by adding into 450 ml of distilled water the following ingredients: 4.0 g trypticase, 3.0 g casamino acids, 6.0 g yeast extract, 0.5 g sodium acetate trihydrate, 1.0 g ammonium citrate, 1.0 g potassium phosphate, 1.0 g magnesium sulfate, 0.05 g manganese sulfate and 500 µl polyoxyethylene (20) sorbitan monooleate.

c. LBS (*Lactobacillus* Selection) Medium

LBS medium may be made by adding into 1 L of distilled water the following ingredients: 10.0 g trypticase, 5.0 g yeast extract, 25.0 g sodium acetate hydrate, 20.0 g glucose, 2.0 g ammonium citrate, 6.0 g monopotassium phosphate, 0.575 g magnesium sulfate anhydrous, 0.12 g manganese sulfate monohydrate, 0.034 g ferrous sulfate, and 1 ml polyoxyethylene (20) sorbitan monooleate. LBS agar may be prepared by adding 15 g of agar to 1 L of the LBS medium.

Example 2

*Lactobacillus amylovorus* M35 Fermentation Protocol a. Medium Optimization for Strain M35 Protocol 450 ml of the Lactobacilli fermentation medium was adjusted to a pH of 7.20 with 6M sodium hydroxide and a stir bar was added to the bottle. The medium was autoclaved for 20 minutes at 121° C. After the fermentation medium was cooled, to room temperature, 50 ml of a sterile 30% glucose solution was added aseptically.

The fermentation medium was pre-warmed to 37° C. in a water bath then inoculated with 5 ml of an overnight culture of *Lactobacillus amylovorus* M35 previously grown in MRS broth. The concentration of a typical overnight M35 culture is about $5\times10^8$ CFU/ml of culture. Therefore, $\sim2.5\times10^9$ total cells were inoculated to the vessel. The bottle was sealed and then placed into a water bath at 37° C. The cap on the bottle had two holes in the top, one large enough to allow a pH probe to pass through and one hole large enough to pipette 6M sodium hydroxide. Unless pH measurement or adjustment was needed, the holes were sealed to minimize oxygen entry. Following inoculation, the bottle was placed on a magnetic stir plate and slowly stirred for a few seconds to homogenize the culture. Incubation occurred until the optical density ($\lambda=600$ nm) (OD600) of the culture reached $\sim1.0$. At this time, a sterile pH probe was inserted into the bottle to measure the pH of the culture. Subsequently to measuring the pH, the culture was adjusted to a pH of approximately 7.0 with 6M sodium hydroxide.

At each pH adjustment time point, the viable cell concentration was measured. The measurement was achieved by removing a 545 µl aliquot of the culture and adding it to 5 ml of MRS broth. The culture was serially diluted in a 10× dilution series to $10^{-8}$ dilution and 100 µl aliquots were plated onto MRS agar plates from dilution tubes. The plates were placed into an anaerobic jar with an oxygen remover catalyst. Plates were then placed into a 37° C. incubator and incubated for 48 hours.

Figure 3:
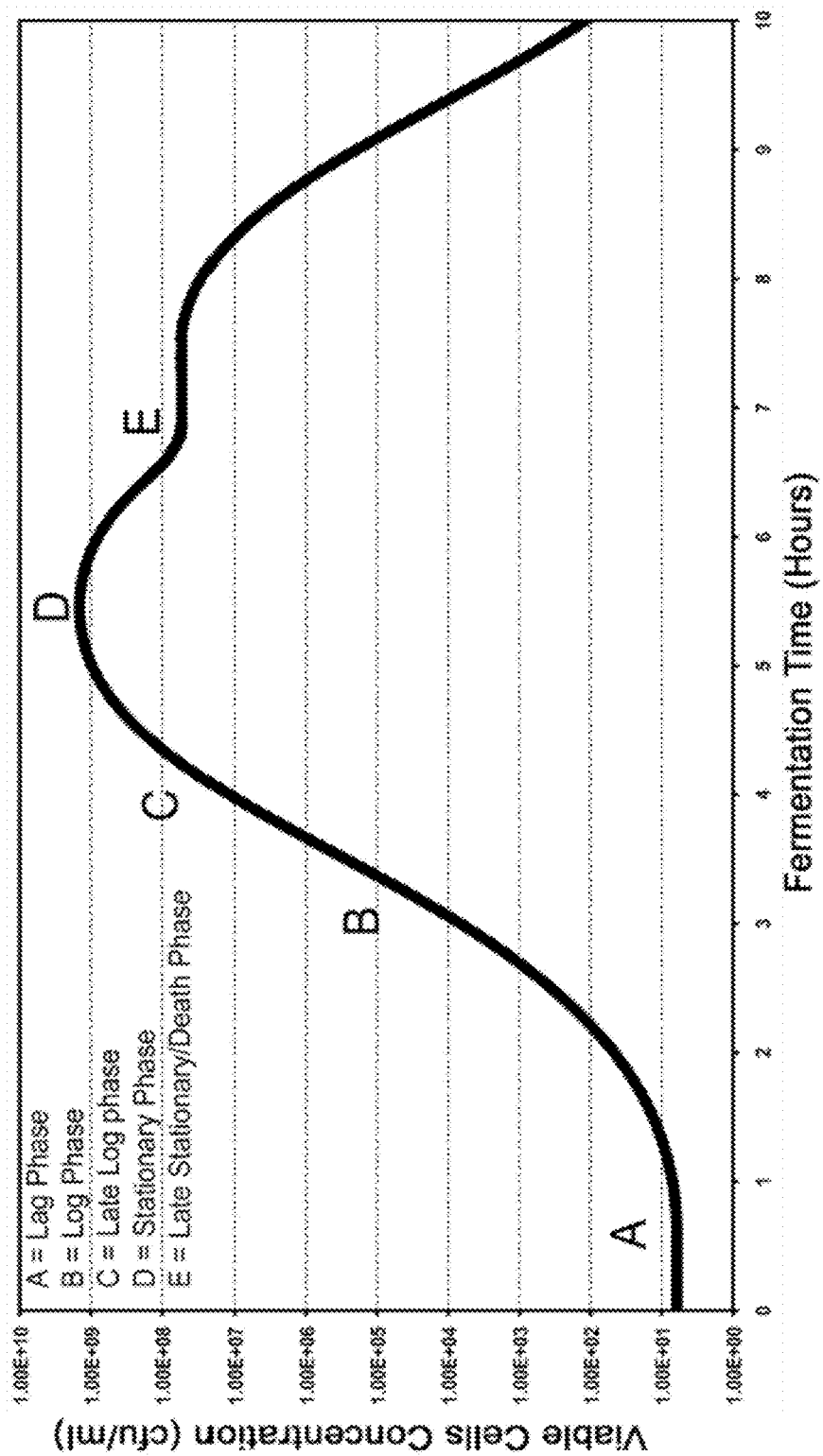
FIG. 3. Graph of typical bacterial growth curve, not specifically indicative of the bacterial species or strains mentioned herein.

Following each 545 µl aliquot removal, the bottle was replaced into the 37° C. water bath and allowed to continue to incubate. The pH probe was left in the bottle to monitor changes of the fermentation medium pH. As the pH of the medium approached 5.5, the bottle was removed from the water bath and culture optical density was measured, a 545 µl aliquot was taken and diluted and plated as described above. These steps were repeated until the culture optical density remained static (stationary phase) or dropped (death phase). FIG. 3.

Figure 2:
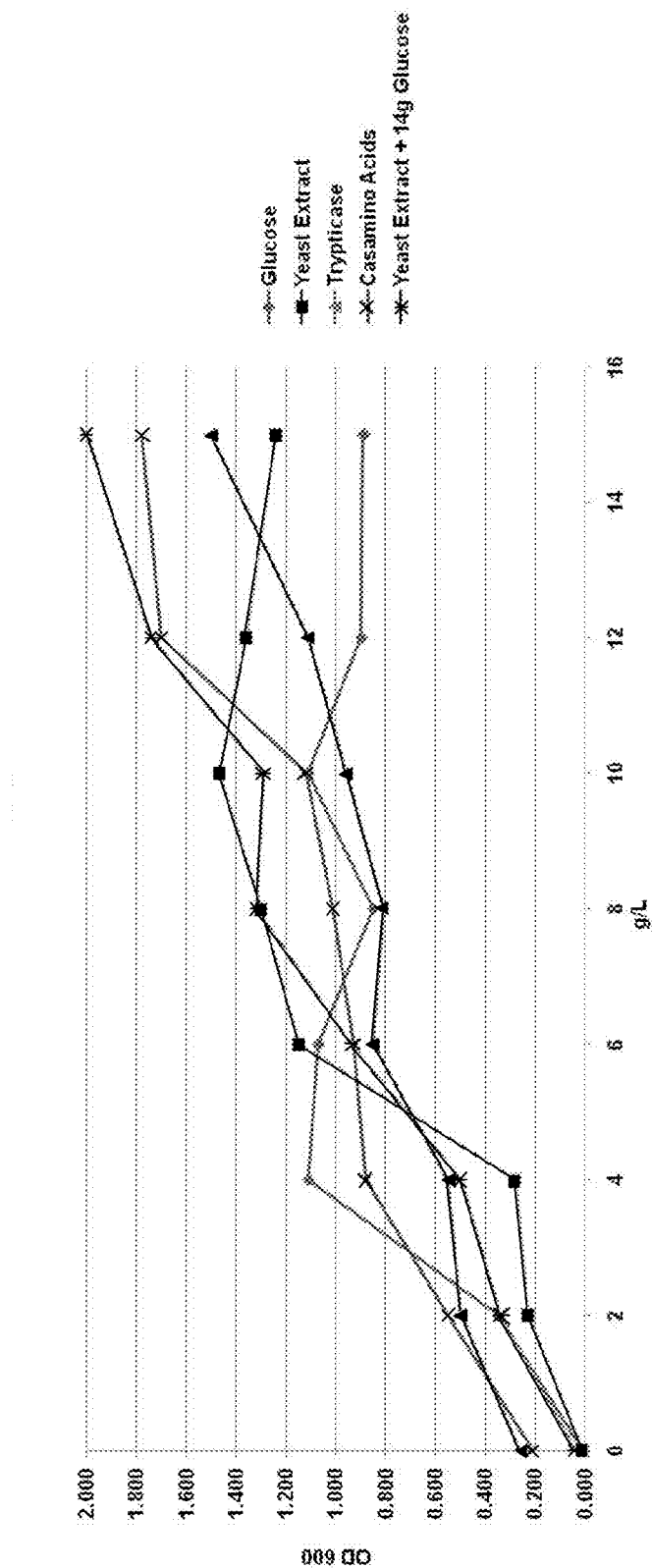
FIG. 2. Graph demonstrating growth of *L. amylovorus* M35 with variable nutrient concentrations for medium optimization.

The following two tables and FIG. 2 reveal optimal growth parameters for M35. Table 1, Table 2, and FIG. 2. This procedure was done to determine the best manner in which to maintain the strain in laboratory settings and to optimally produce the strain for production purposes.

TABLE 1

Culture optical densities with variable nutrient concentrations for medium optimization of strain M35

| Nutrient | g/l Nutrient | | | | | | | |
|---|---|---|---|---|---|---|---|---|
| | 0 | 2 | 4 | 6 | 8 | 10 | 12 | 15 |
| Glucose | 0.010 | 0.350 | 1.110 | 1.070 | 0.850 | 1.110 | 0.900 | 0.890 |
| Yeast Extract | 0.010 | 0.230 | 0.280 | 1.150 | 1.300 | 1.470 | 1.360 | 1.240 |
| Trypticase | 0.260 | 0.500 | 0.550 | 0.850 | 0.810 | 0.960 | 1.110 | 1.500 |
| Casamino Acids | 0.210 | 0.550 | 0.880 | 0.930 | 1.010 | 1.120 | 1.700 | 1.780 |
| Yeast Extract + 14 g glucose | 0.040 | 0.340 | 0.500 | 0.940 | 1.320 | 1.290 | 1.740 | 2.000 |

TABLE 2

Culture final pH values with variable nutrient concentrations for medium optimization for strain M35

| Nutrient | g/l Nutrient | | | | | | | |
|---|---|---|---|---|---|---|---|---|
| | 0 | 2 | 4 | 6 | 8 | 10 | 12 | 15 |
| Glucose | 6.67 | 6.07 | 4.88 | 4.84 | 5.01 | 4.63 | 4.83 | 4.84 |
| Yeast Extract | 6.67 | 6.07 | 6.14 | 4.74 | 4.45 | 4.37 | 4.70 | 4.82 |
| Trypticase | 6.00 | 5.34 | 5.26 | 4.98 | 4.81 | 4.72 | 4.55 | 4.41 |
| Casamino Acids | 5.69 | 5.51 | 4.90 | 4.76 | 4.59 | 4.54 | 4.36 | 4.29 |
| Yeast Extract + 14 g glucose | 6.76 | 6.12 | 5.34 | 4.66 | 4.45 | 4.38 | 4.49 | 4.37 |

The plates containing the aliquots of *Lactobacillus amylovorus* M35 were placed in an anaerobic incubator as described above and colonies were counted for colony forming units (CFU). FIG. 1 and Table 3.

TABLE 3

Growth data from M35 during fermentation conditions

| Runtime | 0:00 | 9:00 | 10:30 | 11:10 | 11:45 | 12:15 | 12:50 | 13:45 | 14:45 | 15:50 | 17:00 | 17:15 |
|---|---|---|---|---|---|---|---|---|---|---|---|---|
| Hours | 0 | 9 | 10.5 | 11 | 11.75 | 12.25 | 13 | 13.75 | 14.75 | 16 | 17 | 17.25 |
| Optical Density | 0 | 1.62 | 3.29 | 5.02 | 6.40 | 8.28 | 8.88 | 9.76 | 9.84 | 11.08 | 10.08 | 9.88 |
| CFU/ml | 0 | | 2.00E+08 | | 8.40E+08 | | 9.40E+08 | 1.44E+09 | 1.23E+09 | 1.31E+09 | 1.49E+09 | |
| CFU/OD | | | 6.08E+07 | | 1.31E+08 | | 1.06E+08 | 1.48E+08 | 1.25E+08 | 1.18E+08 | 1.48E+08 | |
| pH Start | | 5.63 | 5.80 | 5.16 | 6.04 | 5.88 | 5.27 | 5.48 | 6.50 | 7.26 | | |
| pH Finish | | 7.17 | 6.76 | 6.72 | | 6.75 | 6.78 | 6.77 | 7.28 | 7.26 | | |
| 6M NaOH (mls) | 0 | 3 | 3 | 6 | 1 | 3 | 4 | 6 | 2 | 0 | | |
| Total 6M NaOH | 0 | 3 | 6 | 12 | 13 | 16 | 20 | 26 | 28 | 28 | | |
| Cell Mass/ 350 ml (grams) | 18.5 | | | | | | | | | | | | hydroxide. The pH of the medium will be constantly monitored and adjusted to 6.5 with the addition of ammonium hydroxide. The culture will be incubated until optical density of the culture begins to slow, at which time 2 g/L of glucose will be added to the medium. Alternatively a piezoelectric sensor or sensors could be employed for quantitative determination of a *Lactobacillus* species population in media. For example, when the electrodes are immersed in a reaction cell with a bacterial inoculum, the change of frequency can cause a change in the impedance of the microbial metabolism. The sensor may demonstrate the specificity and selectivity for detection of a *Lactobacillus* species in a media. The culture will be further incubated until the growth rate begins to slow. The culture will be pulsed with glucose and incubated two more times and then the cells will be harvested using centrifugation and prepared for preservation. Measuring optical density, piezoelectric measurement or monitoring of the pH of the media may provide a correlation with the amount of glucose that has been consumed. This in turn may indicate how much carbon source should be added to maintain the cells in a carbon source limited state. Alternatively the fermentation is ended based upon when a certain amount of glucose (e.g. 20 g/L glucose) has been added to the fermentation vessel and the pH ceases to decline and base is no longer needed to adjust the pH to 6.5 because all of the glucose has been consumed. In this last example, pilot runs were previously run to confirm the glucose consumption, rate of growth and stage of growth in a pilot scale fermentor. The larger industrial fermentor would be run on the perimeters determined by the pilot scale run.

Example 3

Carbon Source Pulsing

An inoculation culture of 5 L will be grown on fermentation medium supplemented with 6 g/L glucose (or another appropriate carbon source), alternatively the glucose concentration may be even higher, such as 36 g/L. Once the inoculation culture reaches a sufficient viable cell count (e.g. cells have reached mid logarithmic phase) the 5 L inoculation culture is added to a 500 L fermentor. Previously, a sterile 50% glucose solution (or another appropriate carbon source) was added to 500 L of fermentation medium to bring the glucose to a final concentration of 4 g/L. The pH of the fermentation medium will be adjusted to 6.5 with ammonium Example 4

Harvesting

Upon reaching mid logarithmic growth, the cells were harvested through centrifugation. A portion of 350 ml of culture was added to a 500 ml centrifugation bottle and the cap was tightly sealed. The cells were collected by centrifuging the bottle for 20 min at 4000 RPM (1750×g) at 4° C. on a Beckman J2-21M centrifuge equipped with a JA-10 rotor. The supernatant was then removed and the cells suspended in 350 ml PBS and the suspended cells were pelleted again using centrifugation as described above. The cells were then prepared for preservation.

Bacteria harvested according to the present disclosure will tend to be round as opposed to rod shaped. There will be less cellular debris and a higher number of viable cells in the final product than if the bacteria were harvested later than mid-log phase.

Example 5

*Lactobacillus reuteri* Fermentation Protocol 450 ml of the Lactobacilli fermentation medium was adjusted to a pH of 7.20 with 6M sodium hydroxide and a stir bar was added to the bottle. The medium was autoclaved for 20 minutes at 121° C. After the fermentation medium was cooled, to room temperature, 50 ml of a sterile 30% glucose solution was added aseptically.

The fermentation medium was pre-warmed to 37° C. in a water bath then inoculated with 5 ml of an overnight culture of *Lactobacillus reuteri* previously grown in MRS broth. The concentration of a typical overnight culture is $1 \times 10^9$ CFU/ml of culture. Therefore, $\sim 5.0 \times 10^9$ total cells were inoculated to the vessel. The bottle was sealed and then placed into a water bath at 37° C. The cap on the bottle had two holes in the top, one large enough to allow a pH probe to pass through and one hole large enough to pipette 6M sodium hydroxide. Unless pH measurement or adjustment was needed, the holes were sealed to minimize oxygen entry. Following inoculation, the bottle was placed on a magnetic stir plate and slowly stirred for a few seconds to homogenize the culture. Incubation occurred until the optical density ($\lambda$=600 nm) (OD600) of the culture reached ~1.0. At this time, a sterile pH probe was inserted into the bottle to measure the pH of the culture. Subsequently to measuring the pH, the culture was adjusted to a pH of approximately 7.0 with 6M sodium hydroxide.

At each pH adjustment time point, the viable cell concentration was measured. The measurement was achieved by removing a 545 µl aliquot of the culture and adding it to 5 ml of MRS broth. The culture was serially diluted in a 10× dilution series to $10^{-8}$ dilution and 100 µl aliquots were plated onto MRS agar plates from dilution tubes. The plates were placed into an anaerobic jar with an oxygen remover catalyst. Plates were then placed into a 37° C. incubator and incubated for 48 hours.

Following each 545 µl aliquot removal, the bottle was replaced into the 37° C. water bath and allowed to continue to incubate. The pH probe was left in the bottle to monitor changes of the fermentation medium pH. As the pH of the medium approached 5.5, the bottle was removed from the water bath and culture optical density was measured, a 545 µl aliquot was taken and diluted and plated as described above. These steps were repeated until the culture optical density remained static (stationary phase) or dropped (death phase). FIG. 3

Figure 5:
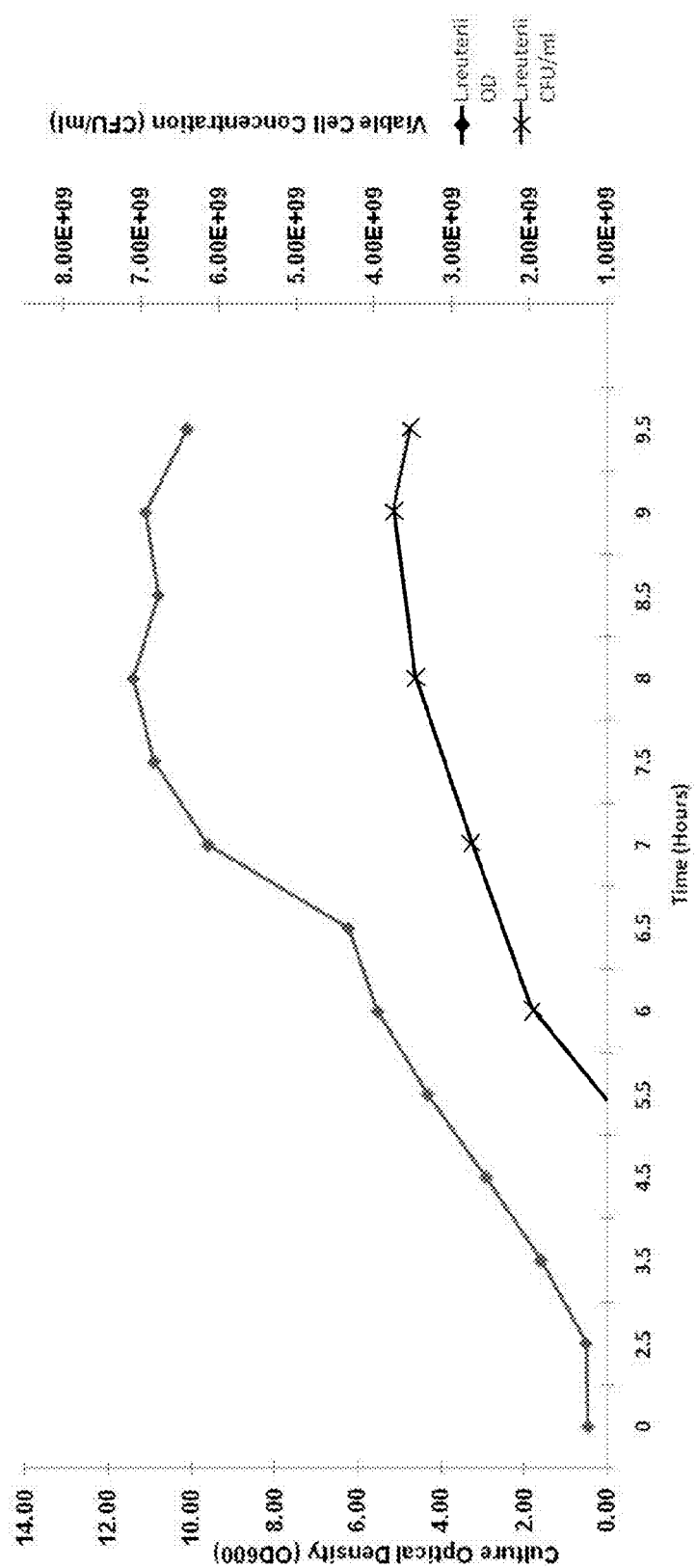
FIG. 5. Graph showing *L. reuteri* culture optical density and viable cell concentration under fermentation conditions.

The plates containing the aliquots of *Lactobacillus reuteri* were placed in an anaerobic incubator as described above and colonies were counted for colony forming units (CFU). FIG. 5 and Table 4.

TABLE 4

Growth Data from *L. reuteri* During Fermentation Conditions

| Time | 10:05 | 12:35 | 1:35 | 2:25 | 3:30 | 4:00 | 4:30 | 5:05 | 5:35 | 6:05 | 6:35 | 7:05 | 7:30 |
|---|---|---|---|---|---|---|---|---|---|---|---|---|---|
| Hours | 0 | 2.5 | 3.5 | 4.5 | 5.5 | 6 | 6.5 | 7 | 7.5 | 8 | 8.5 | 9 | 9.5 |
| OD | 0.46 | 0.50 | 1.60 | 2.91 | 4.32 | 5.52 | 6.22 | 9.60 | 10.90 | 11.40 | 10.80 | 11.10 | 10.10 |
| CFU/ml | | | 3.30E+08 | 4.70E+08 | | 1.95E+09 | | 2.76E+09 | | 3.48E+09 | | 3.75E+09 | 3.55E+09 |
| CFU/OD | 0 | | 2.06E+08 | 1.62E+08 | | 3.53E+08 | | 2.88E+08 | | 3.05E+08 | | 3.38E+08 | 3.51E+08 |
| pH Start | 7.03 | 6.59 | 5.73 | 5.18 | 4.87 | 5.14 | 5.11 | 5.15 | 5.20 | 5.15 | 5.27 | 5.20 | 6.30 |
| pH Start; Finish | — | — | 7.05 | 7.25 | 7.36 | 6.97 | 7.83 | 7.07 | 6.92 | 7.07 | 7.03 | 7.00 | 7.71 |
| ml 12N NaOH added | 0 | 0.0 | 1.0 | 1.5 | 2.0 | 1.5 | 2.0 | 1.7 | 1.5 | 1.8 | 1.7 | 1.7 | 0.8 |
| Total 12N NaOH added | 0 | 0 | 1 | 2.5 | 4.5 | 6 | 8 | 9.7 | 11.2 | 13 | 14.7 | 16.4 | 17.2 |
| Cells Mass/ 350 ml (grams) | 6.29 | | | | | | | | | | | | |

Example 6

*Lactobacillus agilis* Fermentation Protocol 450 ml of the Lactobacilli fermentation medium [from Example 1b] was adjusted to a pH of 7.20 with 6M sodium hydroxide and a stir bar was added to the bottle. The medium was autoclaved for 20 minutes at 121° C. After the fermentation medium was cooled, to room temperature, 50 ml of a sterile 30% glucose solution was added aseptically.

The fermentation medium was pre-warmed to 37° C. in a water bath then inoculated with 5 ml of an overnight culture of *Lactobacillus agilis* previously grown in MRS broth. The concentration of a typical overnight culture is $5 \times 10^8$ CFU/ml of culture. Therefore, $\sim 2.5 \times 10^9$ total cells were inoculated to the vessel. The bottle was sealed and then placed into a water bath at 37° C. The cap on the bottle had two holes in the top, one large enough to allow a pH probe to pass through and one hole large enough to pipette 6M sodium hydroxide. Unless pH measurement or adjustment was needed, the holes were sealed to minimize oxygen entry. Following inoculation, the bottle was placed on a magnetic stir plate and slowly stirred for a few seconds to homogenize the culture. Incubation occurred until the optical density ($\lambda$=600 nm) (OD600) of the culture reached ~1.0. At this time, a sterile pH probe was inserted into the bottle to measure the pH of the culture. Subsequently to measuring the pH, the culture was adjusted to a pH of approximately 7.0 with 6M sodium hydroxide.

At each pH adjustment time point, the viable cell concentration was measured. The measurement was achieved by removing a 545 µl aliquot of the culture and adding it to 5 ml of MRS broth. The culture was serially diluted in a 10× dilution series to $10^{-8}$ dilution and 100 µl aliquots were plated onto MRS agar plates from dilution tubes. The plates were placed into an anaerobic jar with an oxygen remover catalyst. Plates were then placed into a 37° C. incubator and incubated for 48 hours.

Following each 545 µl aliquot removal, the bottle was replaced into the 37° C. water bath and allowed to continue to incubate. The pH probe was left in the bottle to monitor changes of the fermentation medium pH. As the pH of the medium approached 5.5, the bottle was removed from the water bath and culture optical density was measured, a 545 µl aliquot was taken and diluted and plated as described above. These steps were repeated until the culture optical density remained static (stationary phase) or dropped (death phase). FIG. 3.

Figure 6:
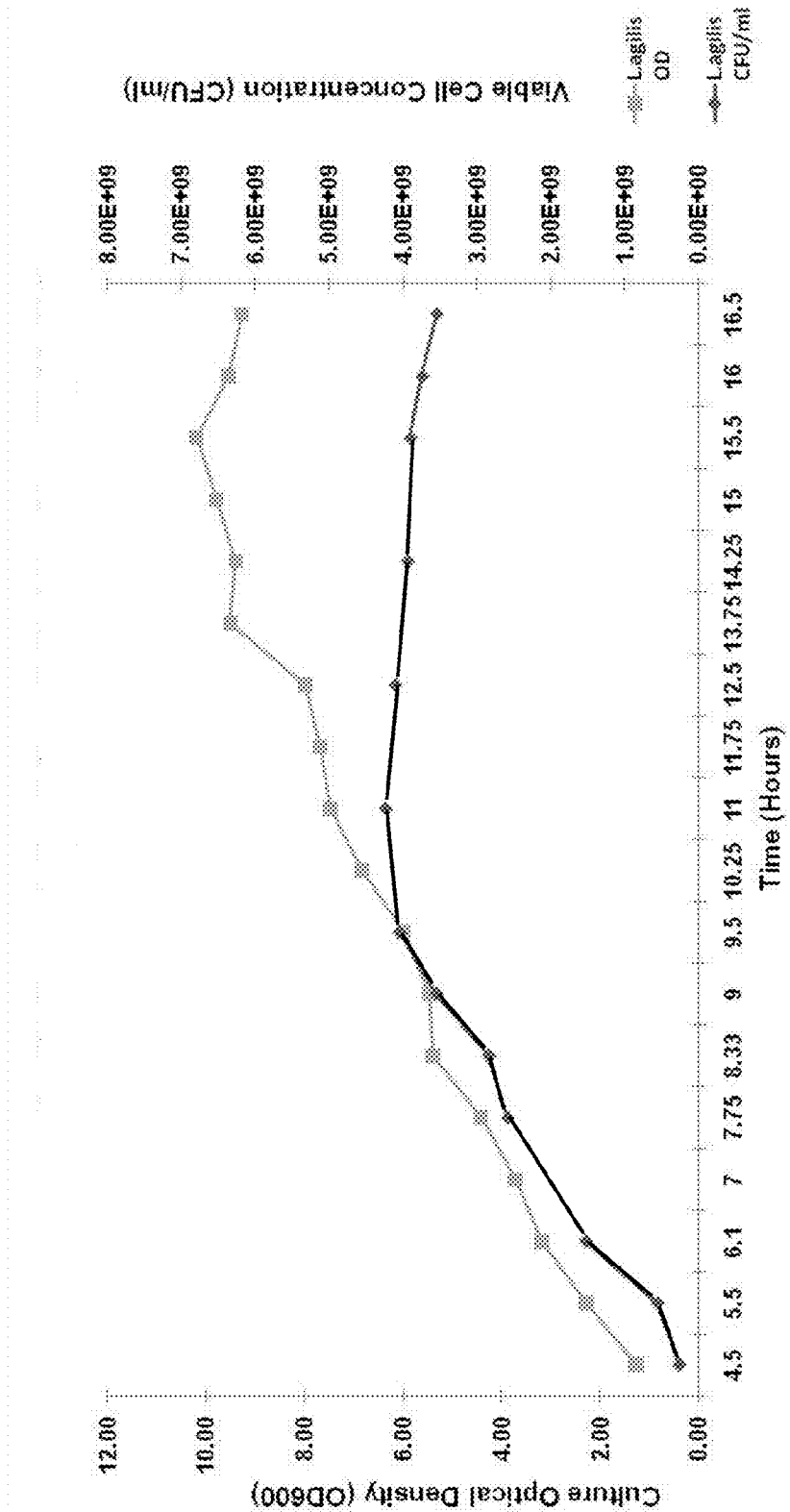
FIG. 6. Graph showing *L. agilis* culture optical density and viable cell concentration under fermentation conditions.

The plates containing the aliquots of *Lactobacillus agilis* were placed in an anaerobic incubator as described above and colonies were counted for colony forming units (CFU). FIG. 6 and Table 5.

hydroxide. Unless pH measurement or adjustment was needed, the holes were sealed to minimize oxygen entry. Following inoculation, the bottle was placed on a magnetic stir plate and slowly stirred for a few seconds to homogenize the culture. Incubation occurred until the optical density ($\lambda$=600 nm) (OD600) of the culture reached ~1.0. At this time, a sterile pH probe was inserted into the bottle to measure the pH of the culture. Subsequently to measuring the pH, the culture was adjusted to a pH of approximately 7.0 with 6M sodium hydroxide.

At each pH adjustment time point, the viable cell concentration was measured. The measurement was achieved by removing a 545 µl aliquot of the culture and adding it to 5 ml of MRS broth. The culture was serially diluted in a 10× dilution series to $10^{-8}$ dilution and 100 µl aliquots were plated onto MRS agar plates from dilution tubes. The plates were

TABLE 5

Growth Data from *L. agilis* During Fermentation Conditions

| Time | 8:30 | 1:05 | 2:00 | 2:50 | 3:30 | 4:15 | 4:50 | 5:30 | 6:00 | 6:45 |
|---|---|---|---|---|---|---|---|---|---|---|
| Hours | 0 | 4.5 | 5.5 | 6.1 | 7 | 7.75 | 8.33 | 9 | 9.5 | 10.25 |
| OD | 0.00 | 1.28 | 2.28 | 3.18 | 3.72 | 4.42 | 5.40 | 5.48 | 6.00 | 6.84 |
| CFU/ml | 0 | 2.70E+08 | 5.70E+08 | 1.54E+09 | | 2.59E+09 | 2.85E+09 | 3.56E+09 | 4.06E+09 | |
| CFU/OD | 0 | 2.11E+08 | 2.50E+08 | 4.84E+08 | | 5.86E+08 | 5.28E+08 | 6.50E+08 | 6.77E+08 | |
| pH Start | | 5.14 | 5.30 | 5.11 | 5.33 | 5.16 | 5.20 | 5.18 | 5.60 | 5.42 |
| pH Start; Finish | | 7.10 | 7.16 | 7.12 | 7.04 | 7.22 | 6.98 | 7.11 | 7.36 | 7.00 |
| ml 6N NaOH added | 0 | 2.2 | 2.0 | 2.6 | 2.0 | 2.6 | 2.4 | 2.6 | 2.0 | 2.2 |
| Total 6N NaOH added | 0 | 2.2 | 4.2 | 6.8 | 8.8 | 11.4 | 13.8 | 16.4 | 18.4 | 20.6 |
| Cells Mass/ 350 ml (g) | 9.08 | | | | | | | | | |

| Time | 7:30 | 8:15 | 9:00 | 10:15 | 10:45 | 11:30 | 12:00 | 12:30 | 1:00 |
|---|---|---|---|---|---|---|---|---|---|
| Hours | 11 | 11.75 | 12.5 | 13.75 | 14.25 | 15 | 15.5 | 16 | 16.5 |
| OD | 7.48 | 7.68 | 8.00 | 9.52 | 9.40 | 9.80 | 10.20 | 9.56 | 9.28 |
| CFU/ml | 4.24E+09 | | 4.11E+09 | | 3.95E+09 | | 3.91E+09 | 3.75E+09 | 3.55E+09 |
| CFU/OD | 5.67E+08 | | 5.14E+08 | | 4.20E+08 | | 3.83E+08 | 3.92E+08 | 3.83E+08 |
| pH Start | 5.36 | 5.31 | 5.35 | 5.33 | 5.48 | 5.32 | 5.56 | 6.68 | 6.97 |
| pH Start; Finish | 7.22 | 7.08 | 7.42 | 7.03 | 7.38 | 7.03 | 7.26 | 7.02 | 6.97 |
| ml 6N NaOH added | 2.6 | 2.8 | 3.0 | 3.0 | 3.0 | 3.40 | 3.00 | 0.40 | 0.00 |
| Total 6N NaOH added | 23.2 | 26 | 29 | 32 | 35 | 38.4 | 41.4 | 41.8 | 41.8 |
| Cells Mass/ 350 ml (g) | | | | | | | | | |

Example 7

*Lactobacillus murinus* Fermentation Protocol 450 ml of the Lactobacilli fermentation medium was adjusted to a pH of 7.20 with 6M sodium hydroxide and a stir bar was added to the bottle. The medium was autoclaved for 20 minutes at 121° C. After the fermentation medium was cooled, to room temperature, 50 ml of a sterile 30% glucose solution was added aseptically.

The fermentation medium was pre-warmed to 37° C. in a water bath then inoculated with 5 ml of an overnight culture of *Lactobacillus murinus* previously grown in MRS broth. The concentration of a typical overnight culture is $1\times10^9$ CFU/ml of culture. Therefore, ~$2.5\times10^9$ total cells were inoculated to the vessel. The bottle was sealed and then placed into a water bath at 37° C. The cap on the bottle had two holes in the top, one large enough to allow a pH probe to pass through and one hole large enough to pipette 6M sodium placed into an anaerobic jar with an oxygen remover catalyst. Plates were then placed into a 37° C. incubator and incubated for 48 hours.

Following each 545 µl aliquot removal, the bottle was replaced into the 37° C. water bath and allowed to continue to incubate. The pH probe was left in the bottle to monitor changes of the fermentation medium pH. As the pH of the medium approached 5.5, the bottle was removed from the water bath and culture optical density was measured, a 545 µl aliquot was taken and diluted and plated as described above. These steps were repeated until the culture optical density remained static (stationary phase) or dropped (death phase). FIG. 3.

Figure 7:
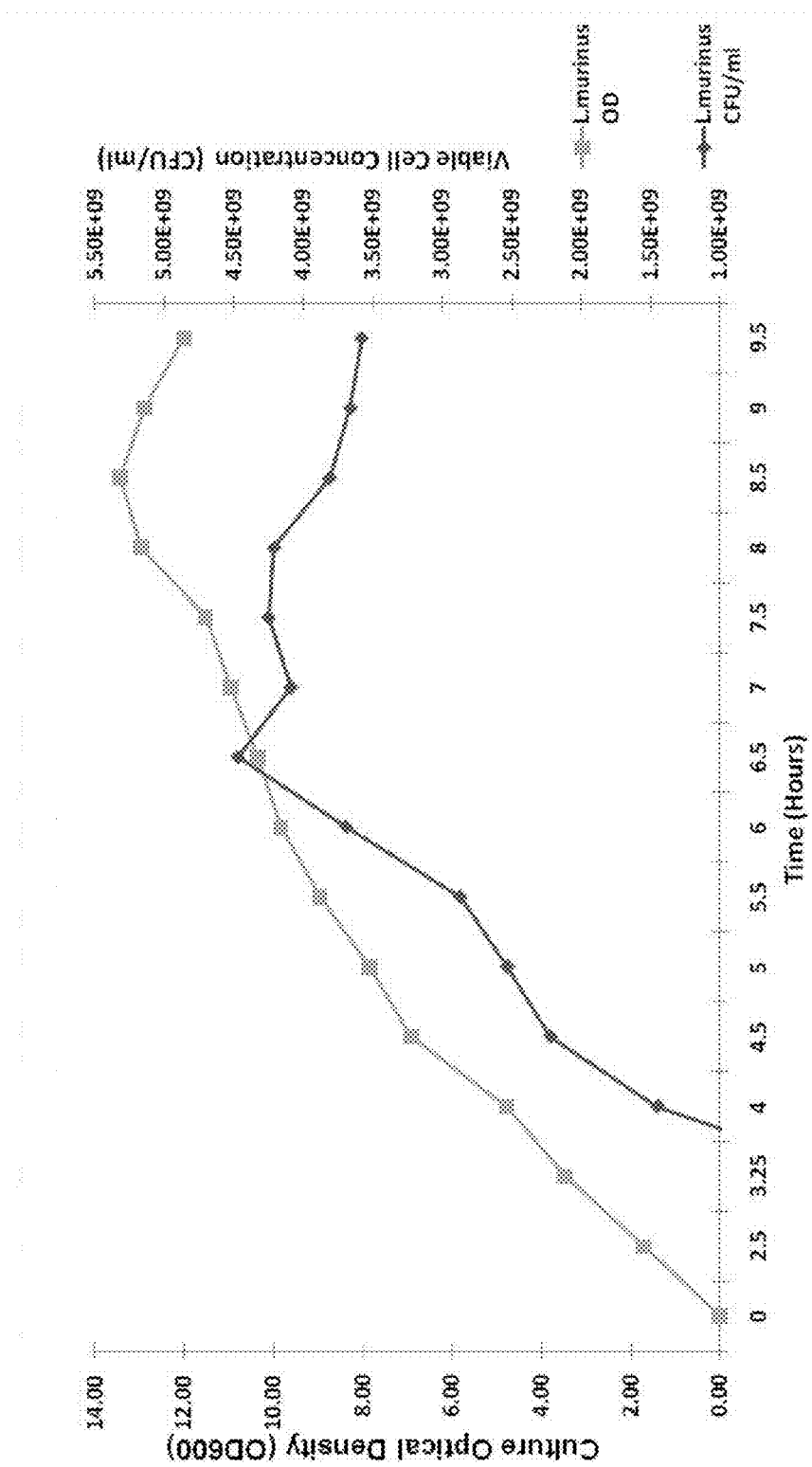
FIG. 7. Graph showing *L. murinus* culture optical density and viable cell concentration under fermentation conditions.

The plates containing the aliquots of *Lactobacillus murinus* were placed in an anaerobic incubator as described above and colonies were counted for colony forming units (CFU). FIG. 7 and Table 6.

TABLE 6

Growth Data from *L. murinus* During Fermentation Conditions

| Time | 8:45 | 11:15 | 12:00 | 12:30 | 1:00 | 1:30 | 1:55 | 2:30 |
|---|---|---|---|---|---|---|---|---|
| Hours | 0 | 2.5 | 3.25 | 4 | 4.5 | 5 | 5.5 | 6 |
| OD | 0.00 | 1.71 | 3.47 | 4.78 | 6.92 | 7.84 | 8.96 | 9.84 |
| CFU/ml | 0 | ND | ND | 1.45E+09 | 2.22E+09 | 2.53E+09 | 2.87E+09 | 3.69E+09 |
| CFU/OD | 0 | | | 3.03E+08 | 3.21E+08 | 3.23E+08 | 3.20E+08 | 3.75E+08 |
| pH Start | | 5.46 | 5.22 | 5.24 | 5.20 | 5.13 | 5.23 | 5.19 |
| pH Start; Finish | | 7.04 | 7.07 | 7.13 | 7.03 | 7.39 | 7.08 | 7.18 |
| ml 6N NaOH added | 0 | 2.5 | 3.0 | 3.0 | 3.3 | 4.0 | 3.5 | 4.0 |
| Total 6N NaOH added | 0 | 2.5 | 5.5 | 8.5 | 11.8 | 15.8 | 19.3 | 23.3 |
| Cell Mass/ 350 ml (grams) | 9.08 | | | | | | | |

| Time | 3:00 | 3:30 | 4:00 | 4:30 | 5:00 | 5:30 | 6:00 |
|---|---|---|---|---|---|---|---|
| Hours | 6.5 | 7 | 7.5 | 8 | 8.5 | 9 | 9.5 |
| OD | 10.36 | 10.96 | 11.52 | 12.96 | 13.44 | 12.88 | 12.00 |
| CFU/ml | 4.47E+09 | 4.09E+09 | 4.25E+09 | 4.21E+09 | 3.81E+09 | 3.66E+09 | 3.58E+09 |
| CFU/OD | 4.31E+08 | 3.73E+08 | 3.69E+08 | 3.25E+08 | 2.83E+08 | 2.84E+08 | 2.98E+08 |
| pH Start | 5.10 | 5.23 | 5.27 | 5.34 | 5.42 | 5.59 | 6.36 |
| pH Start; Finish | 7.01 | 7.03 | 6.99 | 7.08 | 7.08 | 7.00 | 7.04 |
| ml 6N NaOH added | 4.2 | 4.0 | 4.0 | 4.0 | 3.4 | 3.0 | 1.2 |
| Total 6N NaOH added | 27.5 | 31.5 | 35.5 | 39.5 | 42.9 | 45.9 | 47.1 |
| Cell Mass/ 350 ml (grams) | | | | | | | |

Example 8

*Lactobacillus animalis* Fermentation Protocol 450 ml of the Lactobacilli fermentation medium was adjusted to a pH of 7.20 with 6M sodium hydroxide and a stir bar was added to the bottle. The medium was autoclaved for 20 minutes at 121° C. After the fermentation medium was cooled, to room temperature, 50 ml of a sterile 30% glucose solution was added aseptically.

The fermentation medium was pre-warmed to 37° C. in a water bath then inoculated with 5 ml of an overnight culture of *Lactobacillus animalis* previously grown in MRS broth. The concentration of a typical overnight culture is $1 \times 10^9$ CFU/ml of culture. Therefore, ~$5.0 \times 10^9$ total cells were inoculated to the vessel. The bottle was sealed and then placed into a water bath at 37° C. The cap on the bottle had two holes in the top, one large enough to allow a pH probe to pass through and one hole large enough to pipette 6M sodium hydroxide. Unless pH measurement or adjustment was needed, the holes were sealed to minimize oxygen entry. Following inoculation, the bottle was placed on a magnetic stir plate and slowly stirred for a few seconds to homogenize the culture. Incubation occurred until the optical density ($\lambda$=600 nm) (OD600) of the culture reached ~1.0. At this time, a sterile pH probe was inserted into the bottle to measure the pH of the culture. Subsequently to measuring the pH, the culture was adjusted to a pH of approximately 7.0 with 6M sodium hydroxide.

At each pH adjustment time point, the viable cell concentration was measured. The measurement was achieved by removing a 545 µl aliquot of the culture and adding it to 5 ml of MRS broth. The culture was serially diluted in a 10× dilution series to $10^{-8}$ dilution and 100 µl aliquots were plated onto MRS agar plates from dilution tubes. The plates were placed into an anaerobic jar with an oxygen remover catalyst. Plates were then placed into a 37° C. incubator and incubated for 48 hours.

Following each 545 µl aliquot removal, the bottle was replaced into the 37° C. water bath and allowed to continue to incubate. The pH probe was left in the bottle to monitor changes of the fermentation medium pH. As the pH of the medium approached 5.5, the bottle was removed from the water bath and culture optical density was measured, a 545 µl aliquot was taken and diluted and plated as described above. These steps were repeated until the culture optical density remained static (stationary phase) or dropped (death phase). FIG. 3.

Figure 8:
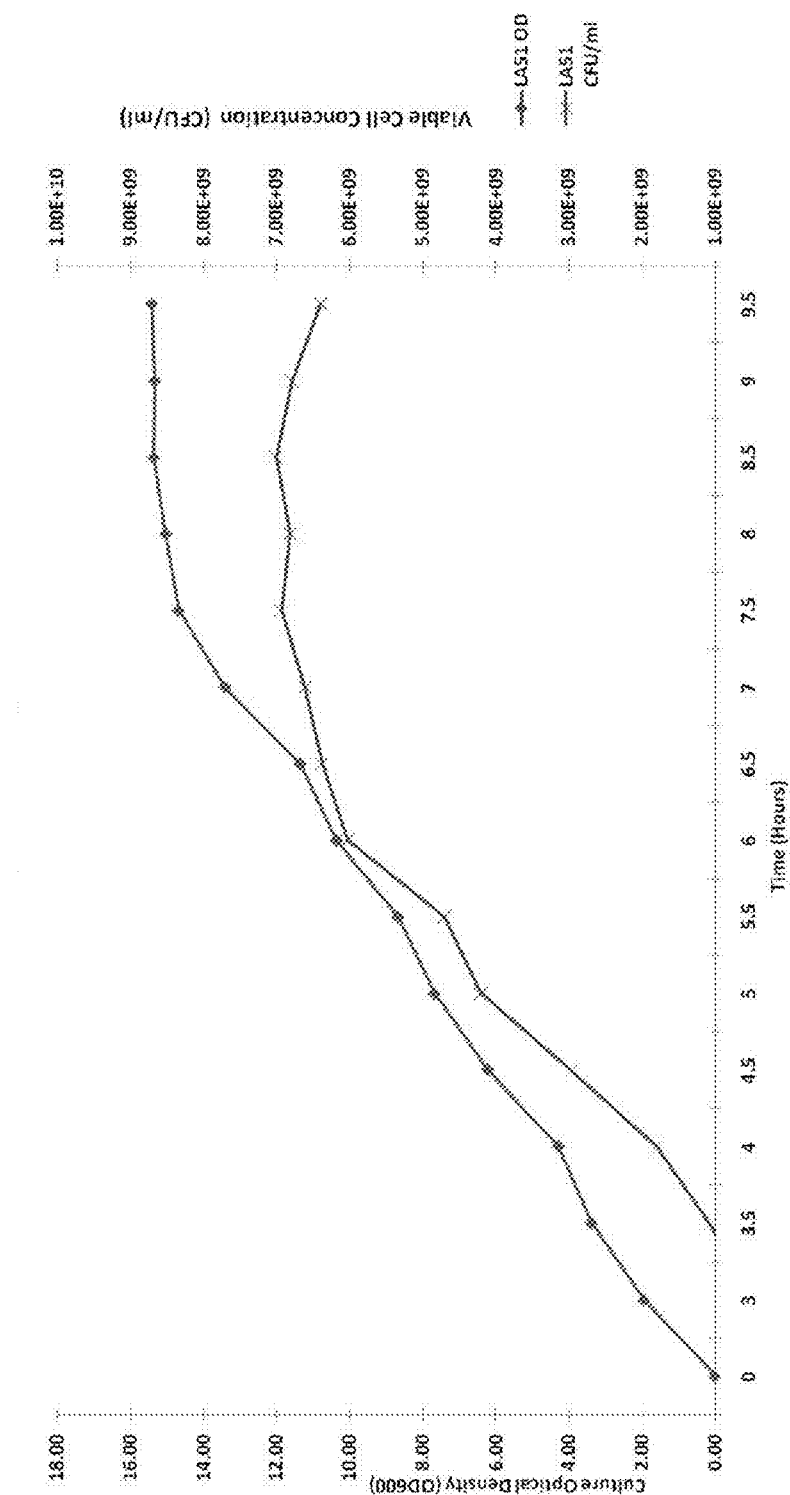
FIG. 8. Graph showing *L. animalis* culture optical density and viable cell concentration under fermentation conditions.

The plates containing the aliquots of *Lactobacillus animalis* were placed in an anaerobic incubator as described above and colonies were counted for colony forming units (CFU). FIG. 8 and Table 7.

TABLE 7

Growth Data from *L. animalis* During Fermentation Conditions

| Time | 8:30 | 11:30 | 12:10 | 12:40 | 1:10 | 1:35 | 2:00 | 2:30 |
|---|---|---|---|---|---|---|---|---|
| Hours | 0 | 3 | 3.5 | 4 | 4.5 | 5 | 5.5 | 6 |
| OD | 0.00 | 1.95 | 3.38 | 4.28 | 6.22 | 7.68 | 8.68 | 10.36 |
| CFU/ml | | 4.80E+08 | 1.08E+09 | 1.80E+09 | 2.97E+09 | 4.21E+09 | 4.71E+09 | 6.03E+09 |
| CFU/OD | | 2.46E+08 | 3.20E+08 | 4.21E+08 | 4.77E+08 | 5.48E+08 | 5.43E+08 | 5.82E+08 |
| pH Start; Finish | | 7.00 | 7.17 | 7.02 | 6.97 | 7.00 | 7.04 | 7.13 |

TABLE 7-continued

Growth Data from *L. animalis* During Fermentation Conditions

| | | | | | | | | |
|---|---|---|---|---|---|---|---|---|
| ml 6N NaOH added | 0 | 2.6 | 3.0 | 3.0 | 3.3 | 3.2 | 3.4 | 4.0 |
| Total 6N NaOH added | 0 | 2.6 | 5.6 | 8.6 | 11.9 | 15.1 | 18.5 | 22.5 |
| Cells Mass/ 350 ml (grams) | 6.20 | | | | | | | |

| | | | | | | | |
|---|---|---|---|---|---|---|---|
| Time | 2:55 | 3:30 | 4:00 | 4:30 | 5:00 | 5:30 | 6:00 |
| Hours | 6.5 | 7 | 7.5 | 8 | 8.5 | 9 | 9.5 |
| OD | 11.36 | 13.40 | 14.68 | 15.04 | 15.36 | 14.44 | 14.16 |
| CFU/ml | 6.38E+09 | 6.61E+09 | 6.93E+09 | 6.82E+09 | 7.01E+09 | 6.79E+09 | 6.40E+09 |
| CFU/OD | 5.62E+08 | 4.93E+08 | 4.72E+08 | 4.53E+08 | 4.56E+08 | 4.70E+08 | 4.52E+08 |
| pH Start; Finish | 7.09 | 7.08 | 7.00 | 7.04 | 7.03 | 7.05 | 7.00 |
| ml 6N NaOH added | 4.0 | 4.4 | 4.2 | 4.0 | 4.0 | 0.5 | 0.1 |
| Total 6N NaOH added | 26.5 | 30.9 | 35.1 | 39.1 | 43.1 | 43.6 | 43.7 |
| Cells Mass/ 350 ml (grams) | | | | | | | |

Example 9

Blending a Microbial Product into a Carrier or Filler

One of skill might also blend the microbial product such as M35 with another carrier or filler to dilute the viable microbial concentration or to facilitate of product application. To blend a microbial product, one will first obtain a lyophilized microbial product having a viable concentration of approximately $5 \times 10^{11}$ CFU per gram. 3.0 grams of the lyophilized microbial, will be mixed with 2,797 grams of a carrier or filler (e.g. lactose, whey powder, sugar) and stirred or shaken thoroughly to create a suspension of microbial product. The resulting product will then have a final viable microbial concentration of $5 \times 10^8$ CFU per gram. This process would be scaled up to any amount of filler. The product would then be suspended in any carrier or filler to any concentration of about $5 \times 10^4$ to about $1 \times 10^{12}$ CFU per gram. The resulting product would then be placed into a bag, bottle, pouch or other container for distribution.

Example 10

*Enterococcus faecium* Fermentation Protocol 450 ml of the Lactobacilli fermentation medium was adjusted to a pH of 7.20 with 6M sodium hydroxide and a stir bar was added to the bottle. The medium was autoclaved for 20 minutes at 121° C. After the fermentation medium was cooled, to room temperature, 50 ml of a sterile 30% glucose solution was added aseptically.

The fermentation medium was pre-warmed to 37° C. in a water bath then inoculated with 5 ml of an overnight culture of *Enterococcus faecium* previously grown in MRS broth. The concentration of a typical overnight culture is $1 \times 10^9$ CFU/ml of culture. Therefore, $\sim 5.0 \times 10^9$ total cells were inoculated to the vessel. The bottle was sealed and then placed into a water bath at 37° C. The cap on the bottle had two holes in the top, one large enough to allow a pH probe to pass through and one hole large enough to pipette 12M sodium hydroxide. Unless pH measurement or adjustment was needed, the holes were sealed to minimize oxygen entry. Following inoculation, the bottle was placed on a magnetic stir plate and slowly stirred for a few seconds to homogenize the culture. Incubation occurred until the optical density ($\lambda=600$ nm) (OD600) of the culture reached $\sim 1.0$. At this time, a sterile pH probe was inserted into the bottle to measure the pH of the culture. Subsequently to measuring the pH, the culture was adjusted to a pH of approximately 7.0 with 12M sodium hydroxide.

At each pH adjustment time point, the viable cell concentration was measured. The measurement was achieved by removing a 545 μl aliquot of the culture and adding it to 5 ml of MRS broth. The culture was serially diluted in a 10× dilution series to $10^{-8}$ dilution and 100 μl aliquots were plated onto MRS agar plates from dilution tubes. The plates were placed into an anaerobic jar with an oxygen remover catalyst. Plates were then placed into a 37° C. incubator and incubated for 48 hours.

Following each 545 μl aliquot removal, the bottle was replaced into the 37° C. water bath and allowed to continue to incubate. The pH probe was left in the bottle to monitor changes of the fermentation medium pH. As the pH of the medium approached 5.5, the bottle was removed from the water bath and culture optical density was measured, a 545 μl aliquot was taken and diluted and plated as described above. These steps were repeated until the culture optical density remained static (stationary phase) or dropped (death phase).

Figure 9:
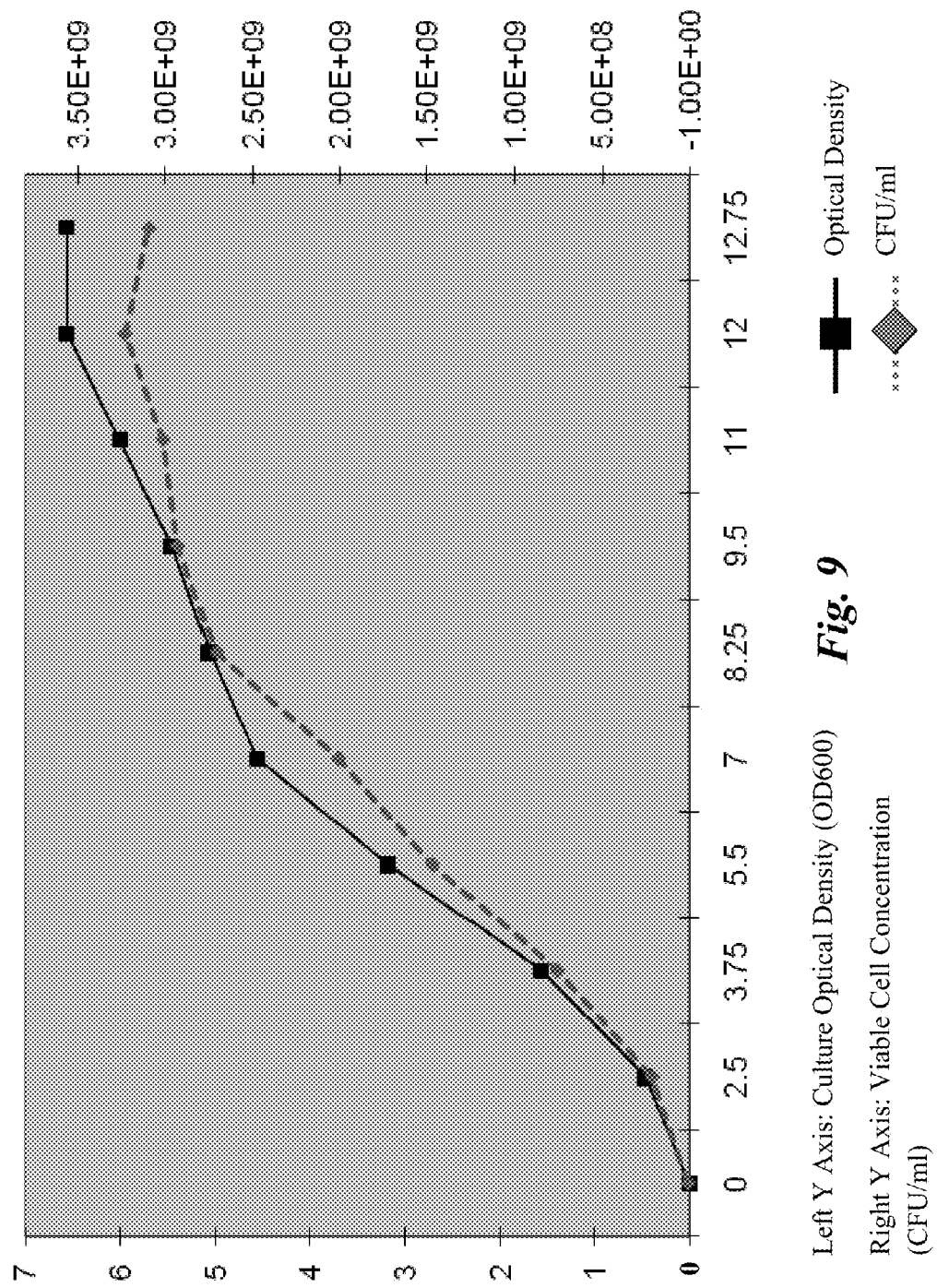
FIG. 9. Graph showing *E. faecium* culture optical density and viable cell concentration under fermentation conditions.

The plates containing the aliquots of *Enterococcus faecium* were placed in an anaerobic incubator as described above and colonies were counted for colony forming units (CFU). FIG. 9 and Table 8.

TABLE 8

Growth Data from *E. faecium* During Fermentation Conditions

| Time | 8:30 | 11:00 | 12:15 | 2:00 | 3:30 | 4:45 | 6:00 | 7:30 | 8:30 | 9:15 |
|---|---|---|---|---|---|---|---|---|---|---|
| Hours | 0 | 2.5 | 3.75 | 5.5 | 7 | 8.25 | 9.5 | 11 | 12 | 12.75 |
| OD | 0 | 0.47 | 1.57 | 3.18 | 4.56 | 5.06 | 5.46 | 6.00 | 6.56 | 6.56 |
| CFU/ml | 9.10E+06 | 2.17E+08 | 7.60E+08 | 1.47E+09 | 2.01E+09 | 2.71E+09 | 2.93E+09 | 2.27E+09 | 3.23E+09 | 3.09E+09 |
| CFU/OD | | 4.62E+08 | 4.84E+08 | 4.62E+08 | 4.41E+08 | 5.36E+08 | 5.37E+08 | 3.78E+08 | 4.92E+09 | 4.71E+08 |

TABLE 8-continued

Growth Data from E. faecium During Fermentation Conditions

| | | | | | | | | | | |
|---|---|---|---|---|---|---|---|---|---|---|
| pH Start | | 6.41 | 5.12 | 5.16 | 5.06 | 5.24 | 5.23 | 5.22 | 5.46 | 5.71 |
| pH Finish | | 6.41 | 7.42 | 6.55 | 6.66 | 6.54 | 6.76 | 6.84 | 6.71 | 7.10 |
| ml 12N NaOH added | 0 | 0 | 1.5 | 1 | 1.25 | 1 | 1.25 | 1.25 | 1 | 1 |
| Total 12N NaOH added | 0 | 0 | 1.5 | 2.5 | 3.75 | 4.75 | 6 | 7.25 | 8.25 | 9.25 |
| Cells Mass/350 ml | 3.82 | | | | | | | | | |
| Cells Mass/1 ml | 0.019 | | | | | | | | | |
| Cells Mass/1 ml | 0.015 | | | | | | | | | |
| Cells Mass/1 ml | 0.022 | | | | | | | | | |
| Cells Mass/1 ml | 0.023 | | | | | | | | | |

Example 10

*Lactobacillus plantarum* Fermentation Protocol 450 ml of the Lactobacilli fermentation medium was adjusted to a pH of 7.20 with 6M sodium hydroxide and a stir bar was added to the bottle. The medium was autoclaved for 20 minutes at 121° C. After the fermentation medium was cooled, to room temperature, 50 ml of a sterile 30% glucose solution was added aseptically.

The fermentation medium was pre-warmed to 37° C. in a water bath then inoculated with 5 ml of an overnight culture of *Lactobacillus plantarum* previously grown in MRS broth. The concentration of a typical overnight culture is $1 \times 10^9$ CFU/ml of culture. Therefore, $\sim 5.0 \times 10^9$ total cells were inoculated to the vessel. The bottle was sealed and then placed into a water bath at 37° C. The cap on the bottle had two holes in the top, one large enough to allow a pH probe to pass through and one hole large enough to pipette 12M sodium hydroxide. Unless pH measurement or adjustment was needed, the holes were sealed to minimize oxygen entry. Following inoculation, the bottle was placed on a magnetic stir plate and slowly stirred for a few seconds to homogenize the culture. Incubation occurred until the optical density ($\lambda$=600 nm) (OD600) of the culture reached ~1.0. At this time, a sterile pH probe was inserted into the bottle to measure the pH of the culture. Subsequently to measuring the pH, the culture was adjusted to a pH of approximately 7.0 with 12M sodium hydroxide.

At each pH adjustment time point, the viable cell concentration was measured. The measurement was achieved by removing a 545 µl aliquot of the culture and adding it to 5 ml of MRS broth. The culture was serially diluted in a 10× dilution series to $10^{-8}$ dilution and 100 µl aliquots were plated onto MRS agar plates from dilution tubes. The plates were placed into an anaerobic jar with an oxygen remover catalyst. Plates were then placed into a 37° C. incubator and incubated for 48 hours.

Following each 545 µl aliquot removal, the bottle was replaced into the 37° C. water bath and allowed to continue to incubate. The pH probe was left in the bottle to monitor changes of the fermentation medium pH. As the pH of the medium approached 5.5, the bottle was removed from the water bath and culture optical density was measured, a 545 µl aliquot was taken and diluted and plated as described above. These steps were repeated until the culture optical density remained static (stationary phase) or dropped (death phase).

Figure 10:
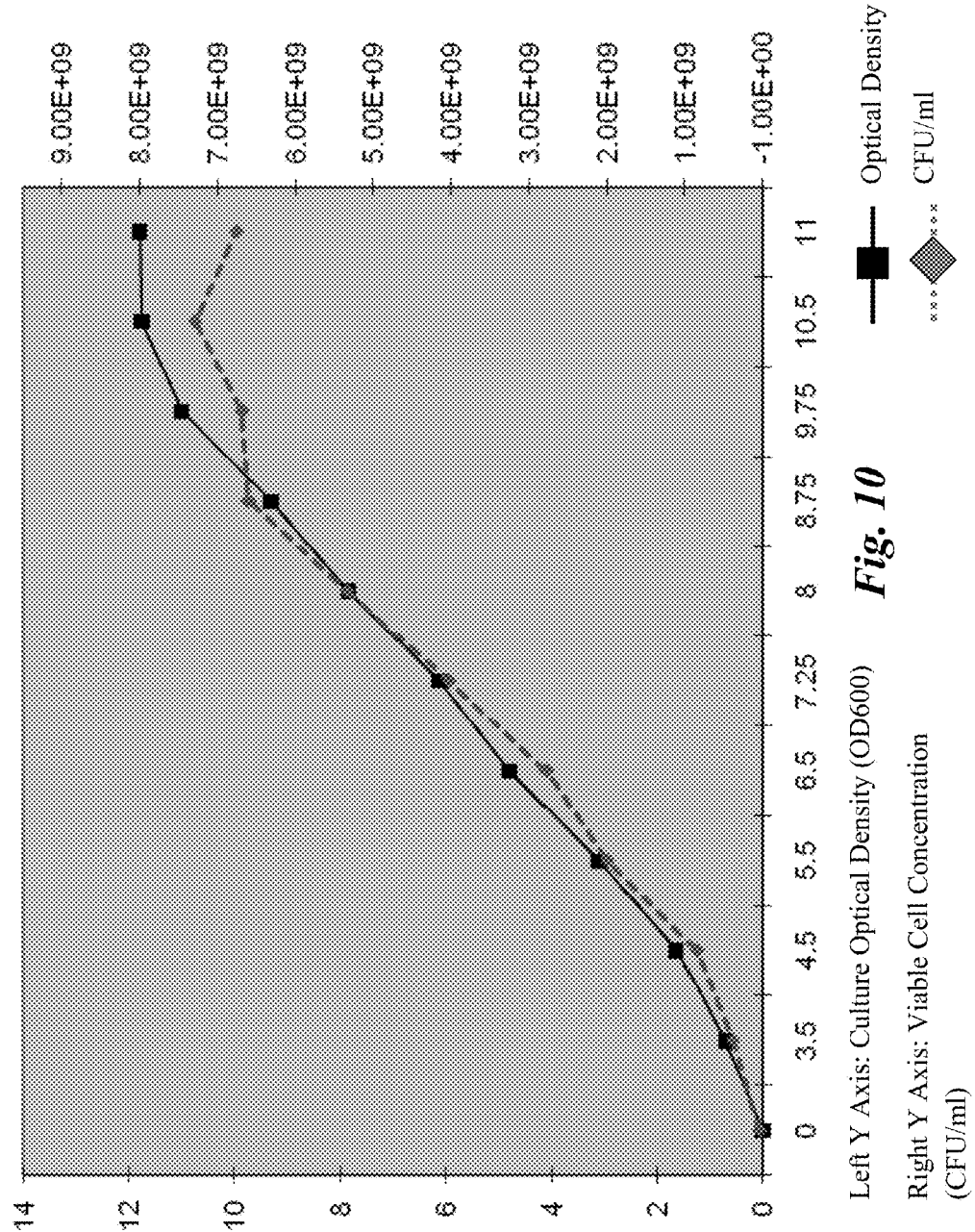
FIG. 10. Graph showing *L. plantarum* culture optical density and viable cell concentration under fermentation conditions.

The plates containing the aliquots of *Lactobacillus plantarum* were placed in an anaerobic incubator as described above and colonies were counted for colony forming units (CFU). FIG. 10 and Table 9.

TABLE 9

Growth Data from L plantarum During Fermentation Conditions

| | | | | | | | | | | | |
|---|---|---|---|---|---|---|---|---|---|---|---|
| Time | 8:00 | 11:30 | 12:30 | 1:30 | 2:30 | 3:15 | 4:00 | 4:45 | 5:45 | 6:30 | 7:00 |
| Hours | 0 | 3.5 | 4.5 | 5.5 | 6.5 | 7.25 | 8 | 8.75 | 9.75 | 10.5 | 11 |
| OD | 0 | 0.71 | 1.63 | 3.11 | 4.78 | 6.12 | 7.84 | 9.32 | 11.00 | 11.76 | 11.80 |
| CFU/ml | 4.40E+07 | 3.88E+08 | 8.50E+08 | 2.00E+09 | 2.78E+09 | 4.03E+09 | 5.34E+09 | 6.61E+09 | 6.68E+09 | 7.29E+09 | 6.75E+09 |
| CFU/OD | | 5.46E+08 | 5.21E+08 | 6.43E+08 | 5.82E+08 | 6.58E+08 | 6.81E+08 | 7.09E+08 | 6.07E+08 | 6.20E+08 | 5.72E+08 |
| pH Start | | 6.26 | 5.46 | 5.23 | 4.96 | 4.85 | 4.90 | 5.07 | 4.96 | 5.40 | 6.14 |
| pH Finish | | 6.26 | 6.86 | 7.00 | 6.95 | 6.37 | 7.24 | 6.62 | 7.09 | 6.89 | 7.03 |
| ml 12N NaOH added | 0 | 0 | 0.75 | 1.5 | 1.5 | 1.5 | 2 | 1.5 | 2 | 1.3 | 0.60 |
| Total 12N NaOH added | 0 | 0 | 0.75 | 2.25 | 3.75 | 5.25 | 7.25 | 8.75 | 10.75 | 12.05 | 12.65 |
| Cells Mass/350 ml | 5.86 | | | | | | | | | | |
| Cells Mass/1 ml | 0.022 | | | | | | | | | | |
| Cells Mass/1 ml | 0.029 | | | | | | | | | | |
| Cells Mass/1 ml | 0.027 | | | | | | | | | | |
| Cells Mass/1 ml | 0.024 | | | | | | | | | | |

Example 11

*Propionibacterium freudenreichii* Fermentation Protocol 450 ml of the Lactobacilli fermentation medium was adjusted to a pH of 7.20 with 6M sodium hydroxide and a stir bar was added to the bottle. The medium was autoclaved for 20 minutes at 121° C. After the fermentation medium was cooled, to room temperature, 50 ml of a sterile 30% glucose solution was added aseptically.

The fermentation medium was pre-warmed to 37° C. in a water bath then inoculated with 5 ml of an overnight culture of *Propionibacterium freudenreichii* previously grown in MRS broth. The concentration of a typical overnight culture is $1\times10^9$ CFU/ml of culture. Therefore, $\sim5.0\times10^9$ total cells were inoculated to the vessel. The bottle was sealed and then placed into a water bath at 37° C. The cap on the bottle had two holes in the top, one large enough to allow a pH probe to pass through and one hole large enough to pipette 6M sodium hydroxide. Unless pH measurement or adjustment was needed, the holes were sealed to minimize oxygen entry. Following inoculation, the bottle was placed on a magnetic stir plate and slowly stirred for a few seconds to homogenize the culture. Incubation occurred until the optical density ($\lambda=600$ nm) (OD600) of the culture reached $\sim1.0$. At this time, a sterile pH probe was inserted into the bottle to measure the pH of the culture. Subsequently to measuring the pH, the culture was adjusted to a pH of approximately 7.0 with 6M sodium hydroxide.

At each pH adjustment time point, the viable cell concentration was measured. The measurement was achieved by removing a 545 µl aliquot of the culture and adding it to 5 ml of MRS broth. The culture was serially diluted in a 10× dilution series to $10^{-8}$ dilution and 100 µl aliquots were plated onto MRS agar plates from dilution tubes. The plates were placed into an anaerobic jar with an oxygen remover catalyst. Plates were then placed into a 37° C. incubator and incubated for 48 hours.

Following each 545 µl aliquot removal, the bottle was replaced into the 37° C. water bath and allowed to continue to incubate. The pH probe was left in the bottle to monitor changes of the fermentation medium pH. As the pH of the medium approached 5.5, the bottle was removed from the water bath and culture optical density was measured, a 545 µl aliquot was taken and diluted and plated onto sodium lactate medium agar plates (per L: 10 g tryptone, 10 g yeast extract, 10 g sodium lactate, 0.25 K$_2$HPO$_4$, 15 g agar; pH 7.2). These steps were repeated until the culture optical density remained static (stationary phase) or dropped (death phase).

Figure 11:
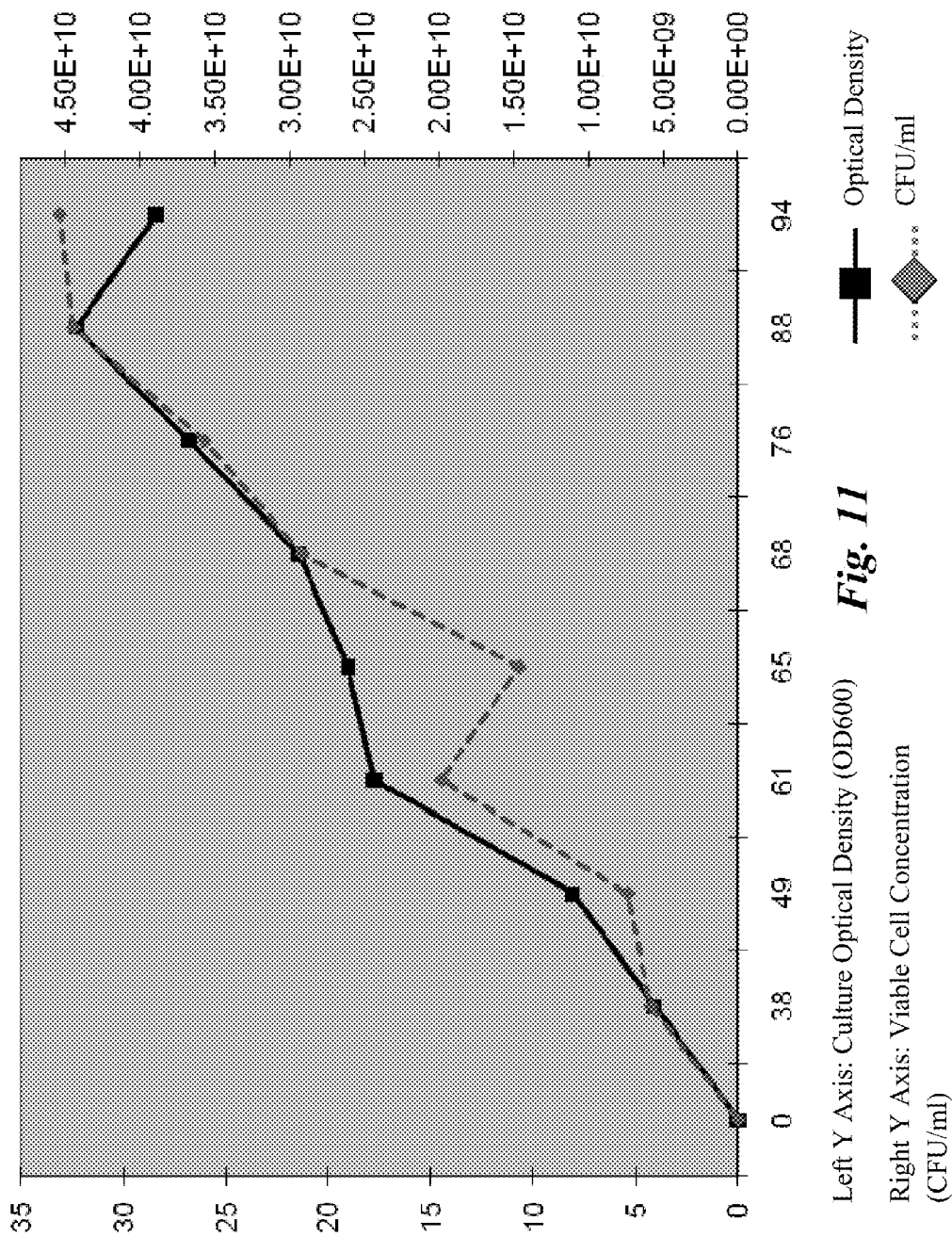
FIG. 11. Graph showing *P. freudenreichii* culture optical density and viable cell concentration under fermentation conditions.

The plates containing the aliquots of *Propionibacterium freudenreichii* were placed in an anaerobic incubator as described above and colonies were counted for colony forming units (CFU). FIG. 11 and Table 10.

TABLE 10

Growth Data from *P. freudenreichii* During Fermentation Conditions

| Time | 19:00 | 9:00 | 20:00 | 8:00 | 12:00 | 15:00 | 23:00 | 11:00 | 15:00 | 17:00 |
|---|---|---|---|---|---|---|---|---|---|---|
| Hours | 0 | 38 | 49 | 61 | 65 | 68 | 76 | 88 | 92 | 94 |
| OD | 0 | 4.08 | 8.08 | 17.76 | 19.02 | 21.44 | 26.80 | 32.32 | | 28.40 |
| CFU/ml | 0 | 5.84E+09 | 7.40E+09 | 1.99E+10 | 1.47E+10 | 2.92E+10 | 3.57E+10 | 4.45E+10 | | 4.54E+10 |
| CFU/OD | | 1.43E+09 | 9.16E+08 | 1.12E+09 | 7.73E+08 | 1.36E+09 | 1.33E+09 | 1.38E+09 | | 1.60E+09 |
| pH Start | | 5.63 | 5.80 | 5.16 | 6.04 | 5.88 | 5.27 | 5.48 | 6.50 | 7.26 |
| pH Finish | | 7.17 | 6.76 | 6.72 | | 6.75 | 6.78 | 6.77 | 7.28 | 7.26 |
| ml 6N NaOH added | 0 | 3 | 3 | 6 | 1 | 3 | 4 | 6 | 2 | 0 |
| Total 6N NaOH added | 0 | 3 | 6 | 12 | 13 | 16 | 20 | 26 | 28 | 28 |
| Cells Mass/350 ml | 18.5 g | | | | | | | | | |
| Cells Mass/1 ml | 0.056 g | | | | | | | | | |
| Cells Mass/1 ml | 0.064 g | | | | | | | | | |

Example 12

*Lactobacillus acidophilus* Fermentation Protocol 450 ml of the Lactobacilli fermentation medium was adjusted to a pH of 7.20 with 6M sodium hydroxide and a stir bar was added to the bottle. The medium was autoclaved for 20 minutes at 121° C. After the fermentation medium was cooled, to room temperature, 50 ml of a sterile 30% glucose solution was added aseptically.

The fermentation medium was pre-warmed to 37° C. in a water bath then inoculated with 5 ml of an overnight culture of *Lactobacillus acidophilus* previously grown in MRS broth. The concentration of a typical overnight culture is $1\times10^9$ CFU/ml of culture. Therefore, $\sim5.0\times10^9$ total cells were inoculated to the vessel. The bottle was sealed and then placed into a water bath at 37° C. The cap on the bottle had two holes in the top, one large enough to allow a pH probe to pass through and one hole large enough to pipette 6M sodium hydroxide. Unless pH measurement or adjustment was needed, the holes were sealed to minimize oxygen entry. Following inoculation, the bottle was placed on a magnetic stir plate and slowly stirred for a few seconds to homogenize the culture. Incubation occurred until the optical density ($\lambda=600$ nm) (OD600) of the culture reached $\sim1.0$. At this time, a sterile pH probe was inserted into the bottle to measure the pH of the culture. Subsequently to measuring the pH, the culture was adjusted to a pH of approximately 7.0 with 6M sodium hydroxide.

At each pH adjustment time point, the viable cell concentration was measured. The measurement was achieved by removing a 545 µl aliquot of the culture and adding it to 5 ml of MRS broth. The culture was serially diluted in a 10× dilution series to $10^{-8}$ dilution and 100 µl aliquots were plated onto MRS agar plates from dilution tubes. The plates were placed into an anaerobic jar with an oxygen remover catalyst. Plates were then placed into a 37° C. incubator and incubated for 48 hours.

Following each 545 µl aliquot removal, the bottle was replaced into the 37° C. water bath and allowed to continue to incubate. The pH probe was left in the bottle to monitor changes of the fermentation medium pH. As the pH of the medium approached 5.5, the bottle was removed from the water bath and culture optical density was measured, a 545 µl aliquot was taken and diluted and plated as described above. These steps were repeated until the culture optical density remained static (stationary phase) or dropped (death phase).

Figure 12:
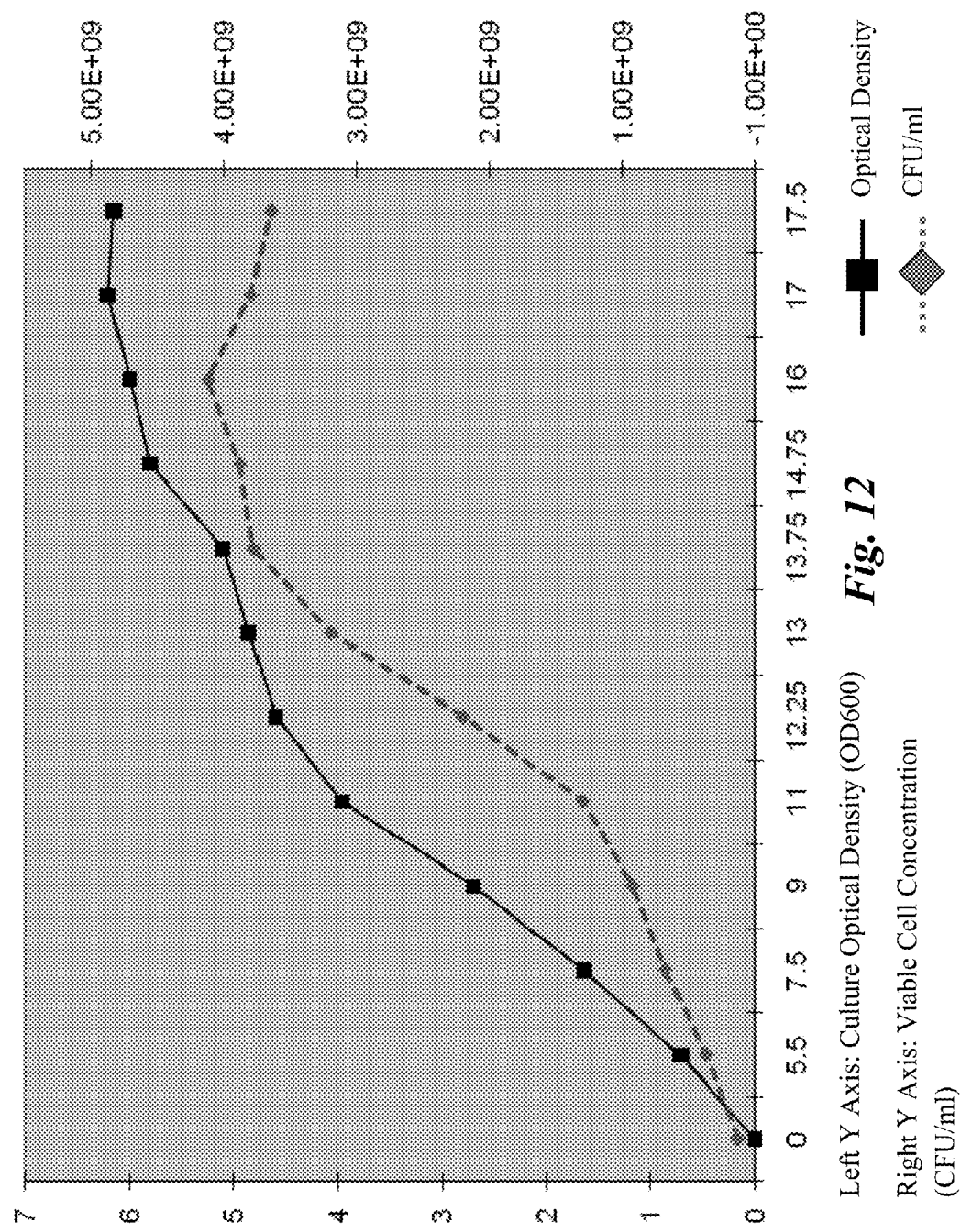
FIG. 12. Graph showing *L. acidophilus* culture optical density and viable cell concentration under fermentation conditions.

The plates containing the aliquots of *Lactobacillus acidophilus* were placed in an anaerobic incubator as described above and colonies were counted for colony forming units (CFU). FIG. 12 and Table 11.

TABLE 11

Growth Data from *L. acidophilus* During Fermentation Conditions

| Time | 6:00 | 11:30 | 1:30 | 3:00 | 5:00 | 6:15 |
|---|---|---|---|---|---|---|
| Hours | 0 | 5.5 | 7.5 | 9 | 11 | 12.25 |
| OD | 0 | 0.71 | 1.40 | 2.70 | 3.96 | 4.60 |
| CFU/ml | 1.30E+08 | 3.67E+08 | 6.71E+08 | 9.20E+08 | 1.30E+09 | 2.20E+09 |
| CFU/OD | | 5.17E+08 | 4.79E+08 | 3.41E+08 | 3.28E+08 | 4.78E+08 |
| pH Start | | 6.33 | 5.26 | 5.15 | 5.08 | 5.25 |
| pH Finish | | 6.33 | 6.86 | 7.12 | 6.95 | 6.88 |
| ml 12N NaOH added | 0 | 0 | 0.75 | 1.50 | 1.50 | 1.50 |
| Total 12N NaOH added | 0 | 0 | 0.75 | 2.25 | 3.75 | 5.25 |
| Cells Mass/350 ml | 3.89 | | | | | |

| Time | 7:00 | 7:45 | 8:45 | 10:00 | 11:00 | 11:30 |
|---|---|---|---|---|---|---|
| Hours | 13 | 13.75 | 14.75 | 16 | 17 | 17.5 |
| OD | 4.85 | 5.10 | 5.80 | 6.00 | 6.20 | 6.15 |
| CFU/ml | 3.20E+09 | 3.78E+09 | 3.88E+09 | 4.12E+09 | 3.80E+09 | 3.65E+09 |
| CFU/OD | 6.60E+08 | 7.41E+08 | 6.69E+08 | 6.87E+08 | 6.13E+08 | 5.93E+08 |
| pH Start | 5.20 | 5.17 | 5.25 | 5.25 | 5.75 | 6.36 |
| pH Finish | 7.25 | 6.78 | 7.08 | 6.89 | 6.75 | 7.15 |
| ml 12N NaOH added | 2.00 | 1.50 | 2.00 | 1.30 | 0.60 | 0.30 |
| Total 12N NaOH added | 7.25 | 8.75 | 10.75 | 12.05 | 12.65 | 12.95 |
| Cells Mass/350 ml | | | | | | |

Example 12

*Propionibacterium acidipropionici* Fermentation Protocol 450 ml of the Lactobacilli fermentation medium was adjusted to a pH of 7.20 with 6M sodium hydroxide and a stir bar was added to the bottle. The medium was autoclaved for 20 minutes at 121° C. After the fermentation medium was cooled, to room temperature, 50 ml of a sterile 30% glucose solution was added aseptically.

The fermentation medium was pre-warmed to 37° C. in a water bath then inoculated with 5 ml of an overnight culture of *Propionibacterium acidipropionici* previously grown in MRS broth. The concentration of a typical overnight culture is 1×10$^9$ CFU/ml of culture. Therefore, ~5.0×10$^9$ total cells were inoculated to the vessel. The bottle was sealed and then placed into a water bath at 37° C. The cap on the bottle had two holes in the top, one large enough to allow a pH probe to pass through and one hole large enough to pipette 6M sodium hydroxide. Unless pH measurement or adjustment was needed, the holes were sealed to minimize oxygen entry. Following inoculation, the bottle was placed on a magnetic stir plate and slowly stirred for a few seconds to homogenize the culture. Incubation occurred until the optical density ($\lambda$=600 nm) (OD600) of the culture reached ~1.0. At this time, a sterile pH probe was inserted into the bottle to measure the pH of the culture. Subsequently to measuring the pH, the culture was adjusted to a pH of approximately 7.0 with 6M sodium hydroxide.

At each pH adjustment time point, the viable cell concentration was measured. The measurement was achieved by removing a 545 µl aliquot of the culture and adding it to 5 ml of MRS broth. The culture was serially diluted in a 10× dilution series to 10$^{-8}$ dilution and 100 µl aliquots were plated onto MRS agar plates from dilution tubes. The plates were placed into an anaerobic jar with an oxygen remover catalyst. Plates were then placed into a 37° C. incubator and incubated for 48 hours.

Following each 545 µl aliquot removal, the bottle was replaced into the 37° C. water bath and allowed to continue to incubate. The pH probe was left in the bottle to monitor changes of the fermentation medium pH. As the pH of the medium approached 5.5, the bottle was removed from the water bath and culture optical density was measured, a 545 µl aliquot was taken and diluted and plated onto sodium lactate medium agar plates (per L: 10 g tryptone, 10 g yeast extract, 10 g sodium lactate, 0.25 K$_2$HPO$_4$, 15 g agar; pH 7.2). These steps were repeated until the culture optical density remained static (stationary phase) or dropped (death phase). FIG.

Figure 13:
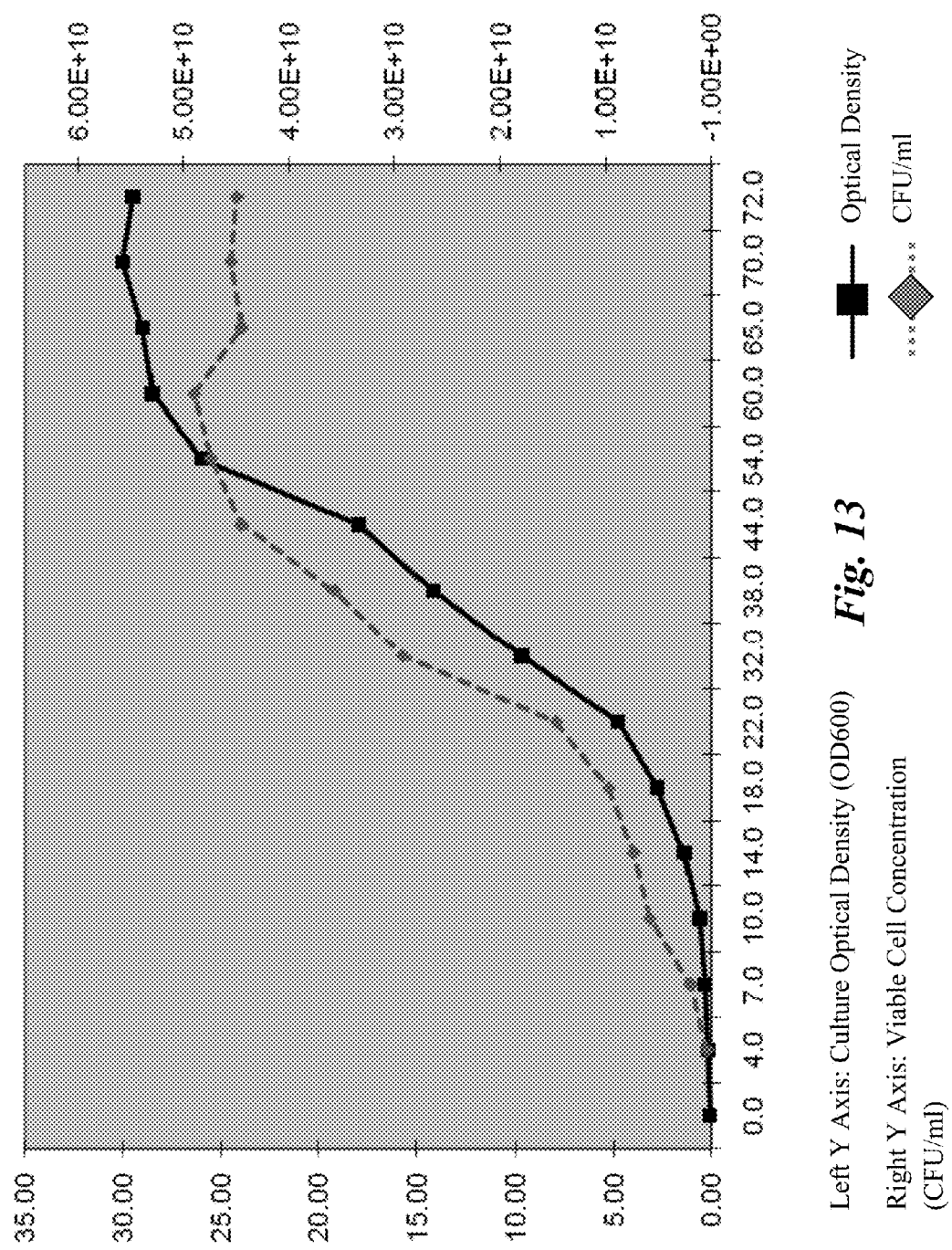
FIG. 13. Graph showing *P. acidipropionici* culture optical density and viable cell concentration under fermentation conditions.

The plates containing the aliquots of *Propionibacterium acidipropionici* were placed in an anaerobic incubator as described above and colonies were counted for colony forming units (CFU). FIG. 13 and Table 12.

TABLE 12

Growth Data from *P. acidipropionici* During Fermentation Conditions

| Time | 6:00 | 10:00 | 1:00 | 3:00 | 7:00 | 11:00 | 4:00 | 2:00 |
|---|---|---|---|---|---|---|---|---|
| Hours | 0.0 | 4.0 | 7.0 | 10.0 | 14.0 | 18.0 | 22.0 | 32.0 |
| OD | 0.09 | 0.18 | 0.36 | 0.61 | 1.39 | 2.75 | 4.76 | 9.70 |
| CFU/ml | | 5.00E+08 | 2.00E+09 | 5.84E+09 | 7.40E+09 | 9.80E+09 | 1.47E+10 | 2.92E+10 |
| CFU/OD | | 2.73E+09 | 5.60E+09 | 9.54E+09 | 5.32E+09 | 3.56E+09 | 3.09E+09 | 3.01E+09 |
| Cells Mass/350 ml | 17.4 | | | | | | | |

| Time | | 8:00 | 2:00 | 12:00 | 6:00 | 11:00 | 4:00 | 6:00 |
|---|---|---|---|---|---|---|---|---|
| Hours | | 38.0 | 44.0 | 54.0 | 60.0 | 65.0 | 70.0 | 72.0 |
| OD | | 14.20 | 18.00 | 26.00 | 28.50 | 29.00 | 30.00 | 29.50 |
| CFU/ml | | 3.57E+10 | 4.45E+10 | 4.74E+10 | 4.90E+10 | 4.45E+10 | 4.54E+10 | 4.49E+10 |
| CFU/OD | | 2.51E+09 | 2.47E+09 | 1.82E+09 | 1.72E+09 | 1.53E+09 | 1.51E+09 | 1.52E+09 |
| Cells Mass/350 ml | | | | | | | | |

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the methods described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

REFERENCES

The following references, to the extent that they provide exemplary procedural or other details supplementary to those set forth herein, are specifically incorporated herein by reference.

Agency Additional Correspondence Letter GRAS Notice No. GRN 000171, CFSAN/Office of Food Additive Safety, Sep. 13, 2006, available at www.fda.gov/Food/FoodIngredientsPackaging/GenerallyRecognizedasSafeGRAS/GRASListings/ucm154102.htm.

Agrawal, P., *Bioprocess Eng.*, 4: 183-190, 1989.

Baldwin and Allison, *Journal of Animal Science*, 57: (Suppl. 2) 461-477, 1993.

Bozoglu et al., *Enzyme Microb. Technol.* 9:531-537, 1987.

Brashears et al., *Journal of Food Protection*, 66(3):355-363, 2003.

Champagne and Gardner, *J. Ind. Microbiol. Biotechnol.* 28:291-296, 2002.

Corcoran et al., *J. Appl. Microbiol.* 96:1024-1039, 2004.

Difco™ & BBL™ Manual, 2nd Edition, Becton Dickinson.

Flint and Angert, *Journal of Microbiological Methods*, 61:235-243, 2005.

Fu and Etzel, *J. Food Sci.* 60:195-200, 1995.

Gibbs et al., *Int. J. Food Sci. Nutr.*, 50: 213-224, 1999.

Heilig et al., *Applied and Environmental Microbiology*, 68:114-123, 2002.

Jun. 6, 2005 GRAS Notification by Nutrition Physiology Corporation, available at www.accessdata.fda.gov/scripts/fcn/gras_notices/grn_171.pdf.

Kurokawa et al., *Biotechnol. Bioeng.*, 44: 95-103, 1994.

Linders et al., *Biotechnol. Prog.* 14:537-539, 1998.

Mary et al., *Soil Biol. and Biochem.* 18:179-184, 1986.

Mauriello et al., *J. Food Prot.*, 62: 773-777, 1999.

O'Riordan et al., *J. Appl. Microbiol.*, 91:1059-1066, 2001.

Roberfroid, M. B., *Am. J. of Clin. Nutr.* 71: 1682S-1687S, 2001.

Teixeira et al., *J. of Dairy Sci.* 78:1025-1031, 1995.

U.S. Pat. No. 3,897,307
U.S. Pat. No. 4,112,942
U.S. Pat. No. 4,749,125
U.S. Pat. No. 5,534,271
U.S. Pat. No. 5,529,793
U.S. Pat. No. 5,641,209
U.S. Pat. No. 5,652,194
U.S. Pat. No. 6,140,355
U.S. Pat. No. 6,258,374
U.S. Pat. No. 6,455,063
U.S. Pat. No. 6,455,271
U.S. Pat. No. 6,468,526
U.S. Pat. No. 6,558,043
U.S. Pat. No. 6,887,489
U.S. Pat. No. 7,063,836
U.S. Publ. Appl. 20070254353

We claim:

1. A method of manufacturing a composition comprising live M35 (ATCC PTA-5249) cells, the method comprising:
   inoculating a bacterial fermentation medium with live M35 (ATCC PTA-5249) cells in which the homology of the live M35 (ATCC PTA-5249) cells to L. *Amylovorus* is approximately 99 percent; and
   harvesting the live M35 (ATCC PTA-5249) cells between mid-log and late-log phase of growth when the live M35 (ATCC PTA-5249) cells are substantially round-shaped, wherein the live M35 (ATCC PTA-5249) cells are harvested during mid-log phase of growth when the live M35 (ATCC PTA-5249) cells are substantially round-shaped.

2. A method of manufacturing a composition comprising live M35 (ATCC PTA-5249) cells, the method comprising:
   inoculating a bacterial fermentation medium with live M35 (ATCC PTA-5249) cells in which the homology of the live M35 (ATCC PTA-5249) cells to L. *Amylovorus* is approximately 99 percent;
   harvesting the live M35 (ATCC PTA-5249) cells between mid-log and late-log phase of growth when the live M35 (ATCC PTA-5249) cells are substantially round-shaped;
   determining, prior to harvesting, that a cell count of the live M35 (ATCC PTA-5249) cells is at least $1\times10^6$ cells/ml; and
   concentrating the live M35 cells to a live cell count of at least $5\times10^9$ cells/ml.

3. The method as recited in claim 2, further comprising preserving the concentrated live M35 (ATCC PTA-5249) cells by lyophilization and after preservation the live cell count of M35 cells is at least $1\times10^{10}$ cells/g.

4. The method as recited in claim 2, further comprising preserving the concentrated live M35 (ATCC PTA-5249) cells by freezing and after preservation the live cell count of M35 cells is at least $5\times10^9$ cells/g.

5. The method as recited in claim 1, wherein the live M35 (ATCC PTA-5249) cells are substantially spherical when harvested between the mid-log and the late-log phase of growth.

6. The method as recited in claim 1, wherein the live M35 (ATCC PTA-5249) cells are harvested at a pre-elongation phase of growth.

7. A method of manufacturing a composition comprising live M35 (ATCC PTA-5249) cells, the method comprising:
inoculating a bacterial fermentation medium with live M35 (ATCC PTA-5249) cells; and
harvesting the live M35 (ATCC PTA-5249) cells during mid-log phase of growth.

8. A method of manufacturing a composition comprising live M35 (ATCC PTA-5249) cells, the method comprising:
inoculating a bacterial fermentation medium with live M35 (ATCC PTA-5249) cells in which the homology of the live M35 (ATCC PTA-5249) cells to L. *Amylovorus* is approximately 99 percent; and
harvesting the live M35 (ATCC PTA-5249) cells during mid-log phase of growth when the live M35 (ATCC PTA-5249) cells are substantially round-shaped.

9. A method of manufacturing a composition comprising live M35 (ATCC PTA-5249) cells, the method comprising:
inoculating a bacterial fermentation medium with live M35 (ATCC PTA-5249) cells in which the homology of the live M35 (ATCC PTA-5249) cells to L. *Amylovorus* is approximately 99 percent; and
harvesting the live M35 (ATCC PTA-5249) cells during mid-log phase of growth.

10. The method as recited in claim 9, further comprising: determining, prior to harvesting, that a cell count of the live M35 (ATCC PTA-5249) cells is at least $1 \times 10^6$ cells/ml.

11. The method as recited in claim 9, further comprising concentrating the live M35 cells to a live cell count of at least $5 \times 10^9$ cells/ml.

12. The method as recited in claim 9, further comprising preserving the live M35 (ATCC PTA-5249) cells by lyophilization and after preservation the live cell count of M35 cells is at least $1 \times 10^{10}$ cells/g.

13. The method as recited in claim 9, further comprising preserving the live M35 (ATCC PTA-5249) cells by freezing and after preservation the live cell count of M35 cells is at least $5 \times 10^9$ cells/g.

14. The method as recited in claim 9, wherein the live M35 (ATCC PTA-5249) cells are substantially spherical.

15. The method as recited in claim 9, wherein the live M35 (ATCC PTA-5249) cells are harvested at a pre-elongation phase of growth.

16. The method as recited in claim 9, further comprising concentrating the live M35 (ATCC PTA-5249) cells by centrifugation.

17. The method as recited in claim 9, further comprising concentrating the live M35 (ATCC PTA-5249) cells by ultrafiltration.

18. The method as recited in claim 9, further comprising concentrating the live M35 (ATCC PTA-5249) cells by sedimentation.

19. The method as recited in claim 9, further comprising preserving the live M35 (ATCC PTA-5249) cells by spray drying.

20. The method as recited in claim 9, further comprising preserving the live M35 (ATCC PTA-5249) cells by refrigeration.

21. The method as recited in claim 9, further comprising carbon pulsing the live M35 (ATCC PTA-5249) cells.

22. The method as recited in claim 9, further comprising adding a cryoprotective agent to the live M35 (ATCC PTA-5249) cells.

23. The method as recited in claim 9, further comprising adding a carrier to the live M35 (ATCC PTA-5249) cells.

24. The method as recited in claim 9, further comprising adding a preservation matrix to the live M35 (ATCC PTA-5249) cells.

25. The method as recited in claim 24, wherein the preservation matrix comprises at least one of: (1) a binding agent, (2) an antioxidant, (3) a polyol, (4) a carbohydrate, (5) maltodextrin beads and (6) a proteinaceous material.

26. A method of manufacturing a composition comprising live M35 (ATCC PTA-5249) cells, the method comprising:
inoculating a bacterial fermentation medium with live M35 (ATCC PTA-5249) cells in which the homology of the live M35 (ATCC PTA-5249) cells to L. *Amylovorus* is approximately 99 percent;
stressing the live M35 (ATCC PTA-5249) cells; and
harvesting the live M35 (ATCC PTA-5249) cells during mid-log phase of growth.

27. The method as recited in claim 26, wherein stressing the live M35 (ATCC PTA-5249) cells comprises exposing the live M35 (ATCC PTA-5249) cells to acid.

28. The method as recited in claim 26, wherein stressing the live M35 (ATCC PTA-5249) cells comprises exposing the live M35 (ATCC PTA-5249) cells to one of: (1) medium pH, (2) elevated temperature, (3) saline, and (4) nitrogen depletion.

29. A method of manufacturing a composition comprising live M35 (ATCC PTA-5249) cells, the method comprising:
inoculating a bacterial fermentation medium with live M35 (ATCC PTA-5249) cells in which the homology of the live M35 (ATCC PTA-5249) cells to L. *Amylovorus* is approximately 99 percent; and
harvesting the live M35 (ATCC PTA-5249) cells during mid-log phase of growth and wherein the live M35 (ATCC PTA-5249) cells are known as one of: (1) *Lactobacillus crispatus* M35 and (2) *Lactobacillus acidophilus* M35.

30. A method of manufacturing a composition comprising live M35 (ATCC PTA-5249) cells, the method comprising:
inoculating a bacterial fermentation medium with live M35 (ATCC PTA-5249) cells in which the homology of the live M35 (ATCC PTA-5249) cells to L. *Amylovorus* is approximately 99 percent; and
harvesting the live M35 (ATCC PTA-5249) cells during mid-log phase of growth and wherein the live M35 (ATCC PTA-5249) cells are known as NP35.

31. A method of manufacturing a composition comprising live M35 (ATCC PTA-5249) cells, the method comprising:
inoculating a bacterial fermentation medium with live M35 (ATCC PTA-5249) cells in which the homology of the live M35 (ATCC PTA-5249) cells to L. *Amylovorus* is approximately 99 percent; and
harvesting the live M35 (ATCC PTA-5249) cells during mid-log phase of growth and wherein the live M35 (ATCC PTA-5249) cells are known as NPC750.

32. A method of manufacturing a composition comprising live M35 (ATCC PTA-5249) cells, the method comprising:
inoculating a bacterial fermentation medium with live M35 (ATCC PTA-5249) cells in which the homology of the live M35 (ATCC PTA-5249) cells to L. *Amylovorus* is approximately 99 percent; and
harvesting the live M35 (ATCC PTA-5249) cells during mid-log phase of growth and wherein the live M35 (ATCC PTA-5249) cells are dividing at their maximum rate during at least a portion of the mid-log phase of growth.

* * * * *

SEQUENCE LISTING

<160> NUMBER OF SEQ ID NOS: 1

<210> SEQ ID NO 1
<211> LENGTH: 1478
<212> TYPE: DNA
<213> ORGANISM: Lactobacillus amylovorus
<220> FEATURE:
<221> NAME/KEY: misc_feature
<222> LOCATION: (34)..(34)
<223> OTHER INFORMATION: n is a, c, g, or t

<400> SEQUENCE: 1

```
cgacgctggc ggcgtgccta atacatgcaa gtcngagcga gcggaaccaa cagatttact      60
tcggtaatga cgttgggaaa gcgagcggcg gatgggtgag taacacgtgg ggaacctgcc     120
cctaagtctg ggataccatt tggaaacagg tgctaatacc ggataataaa gcagatcgca     180
tgatcagctt ttgaaaggcg gcgtaagctg tcgctaaggg atggccccgc ggtgcattag     240
ctagttggta aggtaacggc ttaccaaggc gacgatgcat agccgagttg agagactgat     300
cggccacatt gggactgaga cacggcccaa actcctacgg gaggcagcag tagggaatct     360
tccacaatgg acgcaagtct gatggagcaa cgccgcgtga gtgaagaagg ttttcggatc     420
gtaaagctct gttgttggtg aagaaggata gaggtagtaa ctggccttta tttgacggta     480
atcaaccaga aagtcacggc taactacgtg ccagcagccg cggtaatacg taggtggcaa     540
gcgttgtccg gatttattgg gcgtaaagcg agcgcaggcg gaaaaataag tctaatgtga     600
aagccctcgg cttaaccgag gaactgcatc ggaaactgtt tttcttgagt gcagaagagg     660
agagtggaac tccatgtgta gcggtggaat gcgtagatat atggaagaac accagtggcg     720
aaggcggctc tctggtctgc aactgacgct gaggctcgaa agcatgggta gcgaacagga     780
ttagataccc tggtagtcca tgccgtaaac gatgagtgct aagtgttggg aggtttccgc     840
ctctcagtgc tgcagctaac gcattaagca ctccgcctgg ggagtacgac cgcaaggttg     900
aaactcaaag gaattgacgg gggcccgcac aagcggtgga catgtggtt taattcgaag     960
caacgcgaag aaccttacca ggtcttgaca tctagtgcaa tctgtagaga tacggagttc    1020
ccttcgggga cgctaagaca ggtggtgcat ggctgtcgtc agctcgtgtc gtgagatgtt    1080
gggttaagtc ccgcaacgag cgcaacccct gttattagtt gccagcatta agttgggcac    1140
tctaatgaga ctgccggtga caaaccggag gaaggtgggg atgacgtcaa gtcatcatgc    1200
cccttatgac ctgggctaca cacgtgctac aatgggcagt acaacgagaa gcaagcctgc    1260
gaaggcaagc gaatctctga aagctgttct cagttcggac tgcagtctgc aactcgactg    1320
cacgaagctg gaatcgctag taatcgcgga tcagccgccg cggtgaatac gttcccgggc    1380
cttgtacaca ccgcccgtca caccatggga gtctgcaatg cccaaagccg gtggcctaac    1440
cttcgggaag aagccgtcta aggcagggca gatactgg                             1478
```